United States Patent
Wang et al.

(10) Patent No.: US 10,774,074 B2
(45) Date of Patent: Sep. 15, 2020

(54) 2-(1-HETEROARYLPIPERAZIN-4-YL)METHYL-1,4-BENZODIOXANE DERIVATIVES AS ALPHA2C ANTAGONISTS

(71) Applicant: ORION CORPORATION, Espoo (FI)

(72) Inventors: Shouming Wang, Espoo (FI); Esa Kumpulainen, Helsinki (FI); Jarmo Pystynen, Espoo (FI); Antti Pohjakallio, Espoo (FI); Anssi Haikarainen, Tuusula (FI)

(73) Assignee: ORION CORPORATION, Espoo (FI)

( * ) Notice: Subject to any disclaimer, the term of this patent is extended or adjusted under 35 U.S.C. 154(b) by 0 days.

(21) Appl. No.: 15/579,372

(22) PCT Filed: Jun. 3, 2016

(86) PCT No.: PCT/FI2016/050400
§ 371 (c)(1),
(2) Date: Dec. 4, 2017

(87) PCT Pub. No.: WO2016/193551
PCT Pub. Date: Dec. 8, 2016

(65) Prior Publication Data
US 2018/0215739 A1   Aug. 2, 2018
US 2019/0292170 A9   Sep. 26, 2019

(30) Foreign Application Priority Data
Jun. 5, 2015 (FI) ................................. 20150169

(51) Int. Cl.
| | | |
|---|---|---|
| *C07D 405/14* | (2006.01) | |
| *C07D 413/14* | (2006.01) | |
| *C07D 417/14* | (2006.01) | |
| *C07D 413/12* | (2006.01) | |
| *C07D 513/04* | (2006.01) | |
| *C07D 405/12* | (2006.01) | |
| *C07D 417/12* | (2006.01) | |
| *A61K 31/496* | (2006.01) | |
| *A61P 25/28* | (2006.01) | |
| *A61P 25/18* | (2006.01) | |
| *A61P 25/24* | (2006.01) | |
| *A61P 25/16* | (2006.01) | |

(52) U.S. Cl.
CPC .......... *C07D 405/14* (2013.01); *A61K 31/496* (2013.01); *A61P 25/16* (2018.01); *A61P 25/18* (2018.01); *A61P 25/24* (2018.01); *A61P 25/28* (2018.01); *C07D 405/12* (2013.01); *C07D 413/12* (2013.01); *C07D 413/14* (2013.01); *C07D 417/12* (2013.01); *C07D 417/14* (2013.01); *C07D 513/04* (2013.01)

(58) Field of Classification Search
CPC ... C07D 405/14; C07D 413/14; C07D 417/14
See application file for complete search history.

(56) References Cited

U.S. PATENT DOCUMENTS 3,898,230 A * 8/1975 Regnier ............... C07D 271/04
544/295
4,590,196 A   5/1986 Smith

FOREIGN PATENT DOCUMENTS

WO   WO 2010/058060 A1   5/2010

OTHER PUBLICATIONS

International Search Report issued by the European Patent Office, dated Jul. 25, 2016, 2 pages.

* cited by examiner

*Primary Examiner* — Brian E McDowell
(74) *Attorney, Agent, or Firm* — Finnegan, Henderson, Farabow, Garrett & Dunner, L.L.P.

(57) ABSTRACT

Compounds of formula I,

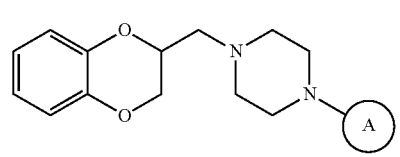

wherein A is an optionally substituted five-membered unsaturated heterocyclic ring containing 1, 2, or 3 N, O, or S ring heteroatom(s) exhibit alpha2C antagonistic activity and are thus useful for the treatment of diseases or conditions of the peripheric or central nervous system.

21 Claims, No Drawings

2-(1-HETEROARYLPIPERAZIN-4-YL)METHYL -1,4-BENZODIOXANE DERIVATIVES AS ALPHA2C ANTAGONISTS

This is a National Stage Application under 35 U.S.C. § 371 of International Patent Application No. PCT/FI2016/050400, filed Jun. 3, 2016, which claims the benefit of Finnish Patent Application No. 20150169, filed Jun. 5, 2015, both of which are incorporated herein by reference.

TECHNICAL FIELD

The present disclosure relates to pharmacologically active aryl piperazines, or pharmaceutically acceptable salts and esters thereof, as well as to pharmaceutical compositions comprising them and to their use as alpha2C antagonists.

BACKGROUND OF THE INVENTION

It is generally known and accepted in the art that compounds exhibiting alpha adrenergic activity may be used for the treatment of a wide variety of diseases and conditions of the peripheric system and the central nervous system (CNS).

The alpha adrenergic receptors can be divided on a pharmacological basis into alpha1 and alpha2 adrenoceptors, which can both be further divided into subtypes. Three genetically encoded subtypes, namely alpha2A, alpha2B, and alpha2C adrenoceptors, have been discovered in human. A fourth pharmacologically defined subtype, namely alpha2D adrenoceptor, is known in some other mammals and in rodents. It corresponds to the genetically defined alpha2A adrenoceptor.

The alpha2 adrenoceptor subtypes have distinct tissue distributions and functional roles. For instance, while alpha2A adrenoceptors are widely expressed in various tissues, alpha2C adrenoceptors are concentrated in the CNS and appear to play a role in the modulation of specific CNS mediated behavioral and physiological responses.

Some compounds that are non-specific for any of the above-mentioned alpha2 subtypes and some compounds that are specific for certain alpha2 subtypes are known in the art. For example, atipamezole disclosed in EP 183 492 is a non-specific alpha2 antagonist. Compounds that are selective antagonists for the alpha2C subtype and are thus useful for the treatment of diseases of the central nervous system, are described, for example in WO 2009/013390 and WO 2010/058060.

In order to be able to reduce the risk of adverse events during treatment, an enhanced selectivity of the alpha2 antagonists would be desirable. For example, the use of non-selective alpha2 antagonists is attributed with side effects, such as increases in blood pressure, heart rate, salivary secretion, gastrointestinal secretion, and anxiety. Also an enhanced potency of the alpha2C antagonists would be desirable, in order to be able to reduce the dose needed.

DE 2241991 B2 discloses certain piperazinyl sydnonimide derivatives possessing hypotensive, vasodilatory and antianginous properties.

SUMMARY OF THE INVENTION

An object of the present disclosure is to provide novel alpha2C antagonists that can be used for the treatment of diseases or conditions of the peripheric or central nervous system wherein alpha2C antagonists are indicated to be useful. Accordingly, an object of the present disclosure is to provide further compounds to be used as alpha2C antagonists in the treatment of mammals. Furthermore, pharmaceutical compositions comprising the presently disclosed compounds are also provided.

The alpha2 antagonists of the present disclosure have an improved selectivity for the alpha2C adrenoceptor subtype, an enhanced potency, improved metabolic stability, and/or improved solubility, moreover, more desirable pharmacokinetic and pharmacodynamics.

DETAILED DESCRIPTION OF THE INVENTION

The present disclosure relates to novel compounds having the general formula I,

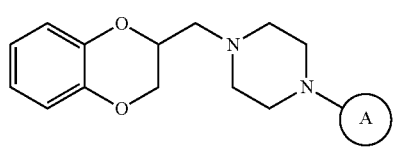

I wherein

A is a five membered unsaturated heterocyclic ring containing 1, 2 or 3 ring heteroatom(s) each independently selected from N, O and S, wherein said heterocyclic ring is unsubstituted, or said heterocyclic ring is substituted with 1 substituent $R_1$, or said heterocyclic ring is substituted with 2 substituents $R_1$ and $R_2$, or said heterocyclic ring is substituted with 3 substituents $R_1$, $R_2$, and $R_3$, or said heterocyclic ring is substituted with 4 substituents $R_1$, $R_2$, $R_3$, and $R_4$;

$R_1$ is $(C_1-C_6)$alkyl, $(C_1-C_6)$alkoxy, hydroxy$(C_1-C_6)$alkyl, $(C_1-C_6)$alkoxy$(C_1-C_6)$alkyl, $(C_1-C_6)$alkoxy-(C=O)—, CN, $(C_1-C_6)$alkyl-(C=O)—, $R_5R_6N$—, $R_5R_6N$—(C=O)—, $R_6(C=O)$—$R_5N$—, heterocyclyl, heterocyclyl-N—, or phenyl-N—, wherein said heterocyclyl or phenyl is optionally substituted with 1, 2, 3, or 4 substituent(s) each independently being $(C_1-C_6)$alkyl, $(C_1-C_6)$alkoxy, oxo, or phenyl $(C_1-C_6)$alkoxy;

$R_2$ is $(C_1-C_6)$alkyl, $(C_1-C_6)$alkoxy, or $(C_1-C_6)$alkoxy$(C_1-C_6)$alkyl;

$R_3$ is $(C_1-C_6)$alkyl, $(C_1-C_6)$alkoxy, or $(C_1-C_6)$alkoxy$(C_1-C_6)$alkyl;

$R_4$ is $(C_1-C_6)$alkyl;

$R_5$ is H, or $(C_1-C_6)$alkyl; and $R_6$ is H, or $(C_1-C_6)$alkyl;

or $R_1$ and $R_2$ form, together with the ring atoms to which they are attached, a condensed 6 membered unsaturated heterocyclic ring, containing 1 or 2 heteroatom(s) being N; or a pharmaceutically acceptable salt or ester thereof;

with the proviso that A is not 1,2,3-oxadiazol-3-ium-3-yl.

In one embodiment the present disclosure relates to compounds of formula I, wherein the compound is a compound of formula Ia,

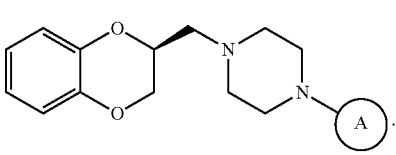

Ia

In one embodiment the present disclosure relates to compounds of formula I, wherein ring A is any one of the following groups (1) 

(2) 

(3) 

(4) 

(5) 

(6) 

(7) 

(8) 

(9) 

(10) 

(11) 

(12) 

(13) 

(14) 

-continued

(15) 

(16) 

(17) 

(18) 

(19) 

(20) 

(21) 

(22) 

wherein
Z is N, O or S; and
atom marked with * is bonded to the parent molecular moiety.

In one embodiment the present disclosure relates to compounds of formula I, wherein $R_1$ is $(C_1-C_6)$alkyl, $(C_1-C_6)$alkoxy, hydroxy$(C_1-C_6)$alkyl, $(C_1-C_6)$alkoxy$(C_1-C_6)$alkyl, $(C_1-C_6)$alkoxy-(C=O)—, CN, $(C_1-C_6)$alkyl-(C=O)—, $R_5R_6N$—, $R_5R_6N$—(C=O)—, $R_6(C=O)$—$R_5N$—, phenyl-N—, or any one of the following groups (1') 

(2') 

(3') 

(4') 

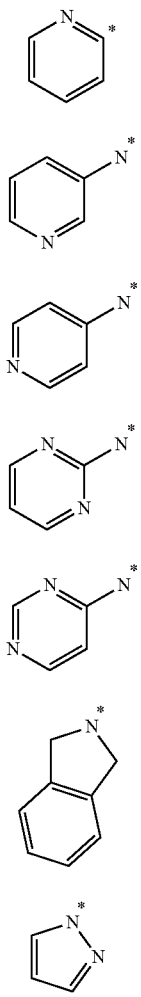

wherein
atom marked with * is bonded to the parent molecular moiety; and
group (1') to (11') is optionally substituted with 1, 2, 3, or 4 substituent(s) each independently being $(C_1-C_6)$alkyl, $(C_1-C_6)$alkoxy, oxo, or phenyl$(C_1-C_6)$alkoxy.

In one embodiment the present disclosure relates to compounds of formula I, wherein ring A is any one of the groups (1), (2), (3), (4), (5), (6), (7), (8), (9), (10), (11), (12), (13), (14), (15), (16), (17), (18), (19), (20), (21), or (22), wherein group (1), (2), (3), (4), (5), (6), (7), (8), (9), (10), (11), (12), (13), (14), (15), (16), (17), (18), (19), (20), (21), or (22) is unsubstituted, or group (1), (2), (3), (4), (5), (6), (7), (8), (9), (10), (11), (12), (13), (14), (15), (16), (17), (18), (19), (20), (21), or (22) is substituted with 1 substituent $R_1$, or group (1), (2), (3), (4), (5), (6), (7), (8), (9), (10), (11), (12), (13), (14), (15), (16), (17), (18), (19), (20), (21), or (22) is substituted with 2 substituents $R_1$ and $R_2$, or group (1), (2), (3), (4), (5), (6), (7), (8), (9), (10), (11), (12), (13), (14), (15), (16), (17), (18), (19), (20), (21), or (22) is substituted with 3 substituents $R_1$, $R_2$, and $R_3$, or group (1), (2), (3), (4), (5), (6), (7), (8), (9), (10), (11), (12), (13), (14), (15), (16), (17), (18), (19), (20), (21), or (22) is substituted with 4 substituents $R_1$, $R_2$, $R_3$, and $R_4$;
$R_1$ is $(C_1-C_6)$alkyl, $(C_1-C_6)$alkoxy, hydroxy$(C_1-C_6)$alkyl, $(C_1-C_6)$alkoxy$(C_1-C_6)$alkyl, $(C_1-C_6)$alkoxy-(C=O)—, CN, $(C_1-C_6)$alkyl-(C=O)—, $R_5R_6N$—, $R_5R_6N$—(C=O)—, $R_6$(C=O)—$R_5N$—, phenyl-N—, or any one of the groups (1'), (2'), (3'), (4'), (5'), (6'), (7'), (8'), (9'), (10'), or (11'), wherein said phenyl or group (1'), (2'), (3'), (4'), (5'), (6'), (7'), (8'), (9'), (10'), or (11') is optionally substituted with 1, 2, 3, or 4 substituent(s) each independently being $(C_1-C_6)$alkyl, $(C_1-C_6)$alkoxy, oxo, or phenyl$(C_1-C_6)$alkoxy;
$R_2$ is $(C_1-C_6)$alkyl, $(C_1-C_6)$alkoxy, or $(C_1-C_6)$alkoxy$(C_1-C_6)$alkyl;
$R_3$ is $(C_1-C_6)$alkyl, $(C_1-C_6)$alkoxy, or $(C_1-C_6)$alkoxy$(C_1-C_6)$alkyl;
$R_4$ is $(C_1-C_6)$alkyl;
$R_5$ is H, or $(C_1-C_6)$alkyl; and
$R_6$ is H, or $(C_1-C_6)$alkyl;
or $R_1$ and $R_2$ form, together with the ring atoms to which they are attached, a condensed 6 membered unsaturated heterocyclic ring, containing 1 or 2 heteroatom(s) being N.

In one embodiment the present disclosure relates to compounds of formula I, wherein ring A is any one of the groups (1), (2), (3), (4), (5), (6), (7), (8), (9), or (10) wherein group (1), (2), (3), (4), (5), (6), (7), (8), (9), or (10) is unsubstituted, or group (1), (2), (3), (4), (5), (6), (7), (8), (9), or (10) is substituted with 1 substituent $R_1$, or group (1), (2), (3), (4), (5), (6), (7), (8), (9), or (10) is substituted with 2 substituents $R_1$ and $R_2$, or group (1), (2), (3), (4), (5), (6), (7), (8), (9), or (10) is substituted with 3 substituents $R_1$, $R_2$, and $R_3$;
$R_1$ is hydroxy$(C_1-C_6)$alkyl, $(C_1-C_6)$alkoxy$(C_1-C_6)$alkyl, $(C_1-C_6)$alkoxy-(C=O)—, CN, $(C_1-C_6)$alkyl-(C=O)—, $R_5R_6N$—(C=O)—, $R_6$(C=O)—$R_5N$—, or any one of the groups (1'), (2'), (3'), (4'), (5'), (6'), (7'), (8'), (9'), or (10'), wherein group (1'), (2'), (3'), (4'), (5'), (6'), (7'), (8'), (9'), or (10'), is optionally substituted with 1, 2, 3, or 4 substituent(s) each independently being $(C_1-C_6)$alkyl, $(C_1-C_6)$alkoxy, oxo, or phenyl$(C_1-C_6)$alkoxy;
$R_2$ is $(C_1-C_6)$alkyl;
$R_3$ is $(C_1-C_6)$alkyl;
$R_5$ is H, or $(C_1-C_6)$alkyl; and
$R_6$ is H, or $(C_1-C_6)$alkyl;
or $R_1$ and $R_2$ form, together with the ring atoms to which they are attached, a condensed 6 membered unsaturated heterocyclic ring, containing 1 heteroatom being N.

In one embodiment the present disclosure relates to compounds of formula I, wherein ring A is any one of the groups (1), (2), (4), (7), (8), (9), or (10), wherein group (1), (2), (4), (7), (8), (9), or (10) is substituted with 1 substituent $R_1$, or group (1), (2), (4), (7), (8), (9), or (10) is substituted with 2 substituents $R_1$ and $R_2$, or group (1), (2), (4), (7), (8), (9), or (10) is substituted with 3 substituents $R_1$, $R_2$, and $R_3$;
$R_1$ is $(C_1-C_6)$alkoxy$(C_1-C_6)$alkyl, $R_5R_6N$—(C=O)—, or any one of the groups (2'), (4'), (5'), or (9'), wherein group (2'), (4'), (5'), or (9') is optionally substituted with 1, 2, 3, or 4 substituent(s) each independently being $(C_1-C_6)$alkyl or oxo;
$R_2$ is $(C_1-C_6)$alkyl;
$R_3$ is $(C_1-C_6)$alkyl;
$R_5$ is $(C_1-C_6)$alkyl; and
$R_6$ is $(C_1-C_6)$alkyl.

In one embodiment the present disclosure relates to compounds of formula I, wherein ring A is any one of the following groups

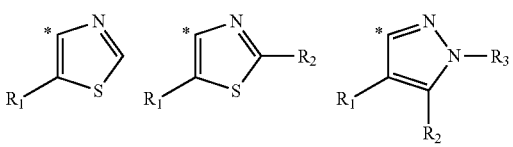

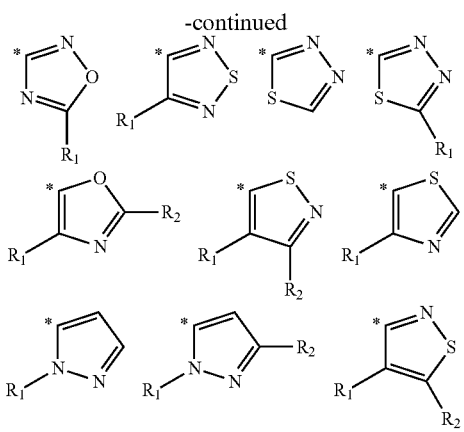

R$_1$ is hydroxy(C$_1$-C$_6$)alkyl, (C$_1$-C$_6$)alkoxy(C$_1$-C$_6$)alkyl, (C$_1$-C$_6$)alkoxy-(C=O)—, CN, (C$_1$-C$_6$)alkyl-(C=O)—, R$_5$R$_6$N—(C=O)—, R$_6$(C=O)—R$_5$N—, or any one of the groups (1'), (2'), (3'), (4'), (5'), (6'), (7'), (8'), (9'), or (10'), wherein group (1'), (2'), (3'), (4'), (5'), (6'), (7'), (8'), (9'), or (10'), is optionally substituted with 1, 2, 3, or 4 substituent(s) each independently being (C$_1$-C$_6$)alkyl, (C$_1$-C$_6$)alkoxy, oxo, or phenyl(C$_1$-C$_6$)alkoxy;

R$_2$ is (C$_1$-C$_6$)alkyl;
R$_3$ is (C$_1$-C$_6$)alkyl;
R$_5$ is H, or (C$_1$-C$_6$)alkyl; and
R$_6$ is H, or (C$_1$-C$_6$)alkyl;

or R$_1$ and R$_2$ form, together with the ring atoms to which they are attached, a condensed 6 membered unsaturated heterocyclic ring, containing 1 heteroatom being N.

In one embodiment the present disclosure relates to compounds of formula I, wherein ring A is any one of the following groups

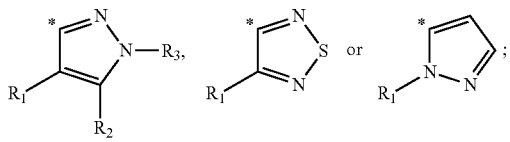

R$_1$ is R$_5$R$_6$N—(C=O)— or any one of groups (2'), (4'), (5'), or (9'), wherein group (2'), (4'), (5'), or (9') is optionally substituted with 1, 2, or 3 substituent(s) each independently being (C$_1$-C$_3$)alkyl or oxo;

R$_2$ is (C$_1$-C$_3$)alkyl;
R$_3$ is (C$_1$-C$_3$)alkyl;
R$_5$ is (C$_1$-C$_3$)alkyl; and
R$_6$ is (C$_1$-C$_3$)alkyl.

In one embodiment the present disclosure relates to compounds of formula I, wherein the compound is (S)-1-(3-(4-((2,3-dihydrobenzo[b][1,4]dioxin-2-yl)methyl)piperazin-1-yl)-1,5-dimethyl-1H-pyrazol-4-yl)-3,3-dimethylpyrrolidine-2,5-dione, (S)-2-(3-(4-((2,3-dihydrobenzo-[b][1,4]dioxin-2-yl)methyl)piperazin-1-yl)-1,5-dimethyl-1H-pyrazol-4-yl)isoindoline-1,3-dione, (S)-5-(4-((2,3-dihydrobenzo[b][1,4]dioxin-2-yl)methyl)piperazin-1-yl)-2-methyloxazole-4-carbonitrile, (S)-1-(3-(4-((2,3-dihydrobenzo[b][1,4]dioxin-2-yl)methyl)piperazin-1-yl)-1,5-dimethyl-1H-pyrazol-4-yl)azetidin-2-one, (S)-3-(4-((2,3-dihydrobenzo[b][1,4]dioxin-2-yl)methyl)piperazin-1-yl)-1,5-dimethyl-1H-pyrazol-4-yl)oxazolidin-2-one, (S)-1-(3-(4-((2,3-dihydrobenzo[b][1,4]dioxin-2-yl)methyl)piperazin-1-yl)-1,5-dimethyl-1H-pyrazol-4-yl)-4,4-dimethylimidazolidin-2-one, (S)-1-(3-(4-((2,3-dihydrobenzo[b][1,4]dioxin-2-yl)methyl)piperazin-1-yl)-1,5-dimethyl-1H-pyrazol-4-yl)-3,4,4-trimethylimidazolidin-2-one, (S)-4-(4-((2,3-dihydrobenzo[b][1,4]dioxin-2-yl)methyl)piperazin-1-yl)-5-(methoxymethyl)thiazole, (S)-1-(3-(4-((2,3-dihydrobenzo[b][1,4]dioxin-2-yl)methyl)piperazin-1-yl)-1,5-dimethyl-1H-pyrazol-4-yl)imidazolidin-2-one, (S)-1-((2,3-dihydrobenzo[b][1,4]dioxin-2-yl)methyl)-4-(1-(pyridin-2-yl)-1H-pyrazol-5-yl)piperazine, (S)-1-((2,3-dihydrobenzo[b][1,4]dioxin-2-yl)methyl)-4-(4-(methoxymethyl)-1,5-dimethyl-1H-pyrazol-3-yl)piperazine, (S)-ethyl 3-(4-((2,3-dihydrobenzo-[b][1,4]dioxin-2-yl)methyl)piperazin-1-yl)-1,5-dimethyl-1H-pyrazole-4-carboxylate, (S)-2-(3-(4-((2,3-dihydrobenzo[b][1,4]dioxin-2-yl)methyl)piperazin-1-yl)-1,5-dimethyl-1H-pyrazol-4-yl)propan-2-ol, (S)-1-(3-(4-((2,3-dihydrobenzo[b][1,4]dioxin-2-yl)methyl)piperazin-1-yl)-1,5-dimethyl-1H-pyrazol-4-yl)pyrrolidin-2-one, (S)-1-(3-(4-((2,3-dihydrobenzo[b][1,4]dioxin-2-yl)methyl)piperazin-1-yl)-1,5-dimethyl-1H-pyrazol-4-yl)-3-methylimidazolidin-2-one, (S)—N-(4-(4-((2,3-dihydrobenzo[b][1,4]dioxin-2-yl)methyl)piperazin-1-yl)-1,2,5-thiadiazol-3-yl)acetamide, (S)-1-(4-(4-((2,3-dihydrobenzo[b][1,4]dioxin-2-yl)methyl)piperazin-1-yl)-1,2,5-thiadiazol-3-yl)-3,3-dimethylpyrrolidin-2-one, (S)-4-(4-((2,3-dihydrobenzo[b][1,4]dioxin-2-yl)methyl)piperazin-1-yl)-N-(pyrimidin-2-yl)-1,2,5-thiadiazol-3-amine, (S)-4-(4-((2,3-dihydrobenzo[b][1,4]dioxin-2-yl)methyl)piperazin-1-yl)-N-(pyrimidin-4-yl)-1,2,5-thiadiazol-3-amine, (S)-1-(5-(4-((2,3-dihydrobenzo[b][1,4]dioxin-2-yl)methyl)piperazin-1-yl)thiazol-4-yl)pyrrolidin-2-one, 1-(4-(4-(((S)-2,3-dihydrobenzo[b][1,4]dioxin-2-yl)methyl)piperazin-1-yl)-1,2,5-thiadiazol-3-yl)-3-methylpyrrolidin-2-one, (S)-2-(4-((2,3-dihydrobenzo[b][1,4]dioxin-2-yl)methyl)piperazin-1-yl)-1,3,4-thiadiazole, (S)-3-(4-((2,3-dihydrobenzo[b][1,4]dioxin-2-yl)methyl)piperazin-1-yl)-5-(methoxymethyl)-1,2,4-oxadiazole, (S)-1-(4-(4-((2,3-dihydrobenzo[b][1,4]dioxin-2-yl)methyl)-piperazin-1-yl)-1,2,5-thiadiazol-3-yl)pyrrolidin-2-one, (S)-1-(5-(4-((2,3-dihydrobenzo[b][1,4]-dioxin-2-yl)methyl)piperazin-1-yl)-1,3,4-thiadiazol-2-yl)imidazolidin-2-one, (S)-3-(4-(4-((2,3-dihydrobenzo[b][1,4]dioxin-2-yl)methyl)piperazin-1-yl)-1,2,5-thiadiazol-3-yl)oxazolidin-2-one, (S)-4-(4-((2,3-dihydrobenzo[b][1,4]dioxin-2-yl)methyl)piperazin-1-yl)-1,2,5-thiadiazole-3-carboxamide, (S)-1-(4-(4-((2,3-dihydrobenzo[b][1,4]dioxin-2-yl)methyl)piperazin-1-yl)-1,2,5-thiadiazol-3-yl)-3-methylimidazolidin-2-one, (S)-4-(4-((2,3-dihydrobenzo[b][1,4]dioxin-2-yl)methyl)piperazin-1-yl)-N-methyl-1,2,5-thiadiazole-3-carboxamide hydrochloride, (S)-1-(4-(4-((2,3-dihydrobenzo[b][1,4]dioxin-2-yl)methyl)piperazin-1-yl)-1,2,5-thiadiazol-3-yl)imidazolidin-2-one, (S)-1-(5-(4-((2,3-dihydrobenzo[b][1,4]dioxin-2-yl)methyl)piperazin-1-yl)-3-methyl-isothiazol-4-yl)pyrrolidin-2-one, (S)-1-(4-(4-((2,3-dihydrobenzo[b][1,4]dioxin-2-yl)methyl)-piperazin-1-yl)-2-methylthiazol-5-yl)-3,3-dimethylpyrrolidine-2,5-dione hydrochloride, (S)-1-(4-(4-((2,3-dihydrobenzo[b][1,4]dioxin-2-yl)methyl)piperazin-1-yl)-1,2,5-thiadiazol-3-yl)ethanone, (S)-4-(4-((2,3-dihydrobenzo[b][1,4]dioxin-2-yl)methyl)piperazin-1-yl)-N,N-dimethyl-1,2,5-thiadiazole-3-carboxamide, (S)-4-(4-((2,3-dihydrobenzo[b][1,4]dioxin-2-yl)methyl)piperazin-1-yl)-N-(pyridin-4-yl)-1,2,5-thiadiazol-3-amine dihydrochloride, (S)-3-(4-((2,3-dihydrobenzo-[b][1,4]dioxin-2-yl)methyl)piperazin-1-yl)isothiazolo[4,5-b]pyridine hydrochloride, (S)—N-(2-(benzyloxy)pyridin-3-yl)-4-(4-((2,3-dihydrobenzo[b][1,4]-dioxin-2-yl)methyl)piperazin-1-yl)-1,2,5-thiadiazol-3-amine hydrochloride, (S)-1-((2,3-dihydrobenzo

[b][1,4]dioxin-2-yl)methyl)-4-(3-methyl-1-(pyridin-2-yl)-1H-pyrazol-5-yl)piperazine, (S)-1-((2,3-dihydrobenzo[b][1,4]dioxin-2-yl)methyl)-4-(1-(6-methoxypyridin-2-yl)-3-methyl-1H-pyrazol-5-yl)piperazine, or (S)-1-((2,3-dihydrobenzo[b][1,4]dioxin-2-yl)methyl)-4-(3-methyl-1-(6-methylpyridin-2-yl)-1H-pyrazol-5-yl)piperazine.

In one embodiment the present disclosure relates to compounds of formula I, wherein the compound is

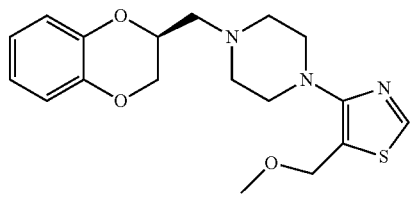 [SMILES: COCc1scnc1N1CCN(C[C@H]2COc3ccccc3O2)CC1]

or a pharmaceutically acceptable salt thereof.

In one embodiment the present disclosure relates to compounds of formula I, wherein the compound is

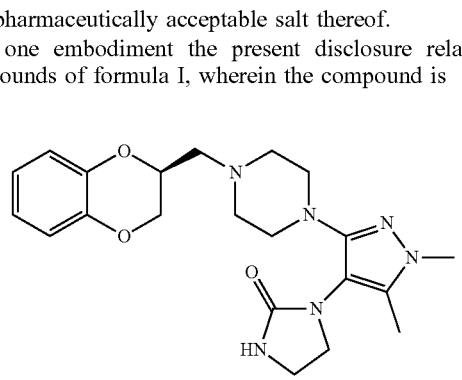

or a pharmaceutically acceptable salt thereof.

In one embodiment the present disclosure relates to compounds of formula I, wherein the compound is

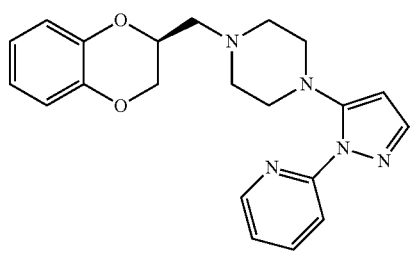 [SMILES: c1ccc(-n2nccc2N2CCN(C[C@H]3COc4ccccc4O3)CC2)nc1]

or a pharmaceutically acceptable salt thereof.

In one embodiment the present disclosure relates to compounds of formula I, wherein the compound is

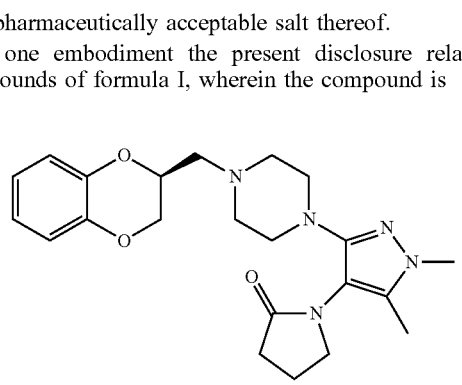

or a pharmaceutically acceptable salt thereof.

In one embodiment the present disclosure relates to compounds of formula I, wherein the compound is

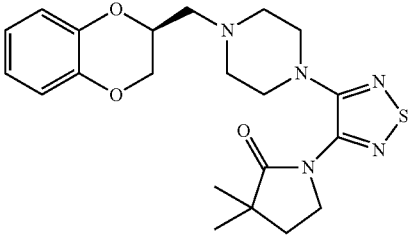 [SMILES: CC1(C)CCN(c2nsnc2N2CCN(C[C@H]3COc4ccccc4O3)CC2)C1=O]

or a pharmaceutically acceptable salt thereof.

In one embodiment the present disclosure relates to compounds of formula I, wherein the compound is

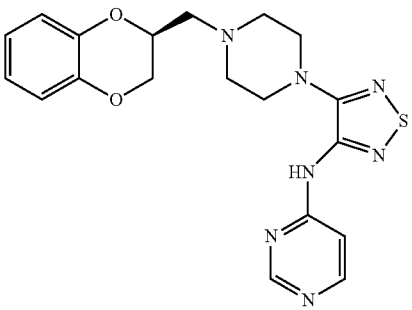 [SMILES: c1ccc2c(c1)OC[C@H](CN1CCN(c3nsnc3Nc3ccncn3)CC1)O2]

or a pharmaceutically acceptable salt thereof.

In one embodiment the present disclosure relates to compounds of formula I, wherein the compound is

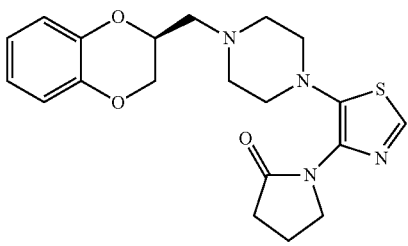 [SMILES: O=C1CCCN1c1ncsc1N1CCN(C[C@H]2COc3ccccc3O2)CC1]

or a pharmaceutically acceptable salt thereof.

In one embodiment the present disclosure relates to compounds of formula I, wherein the compound is

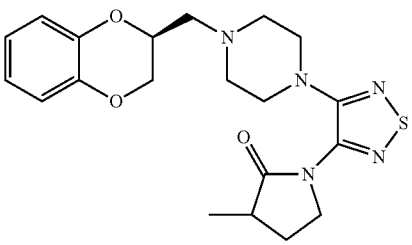 [SMILES: CC1CCN(c2nsnc2N2CCN(C[C@H]3COc4ccccc4O3)CC2)C1=O]

or a pharmaceutically acceptable salt thereof.

In one embodiment the present disclosure relates to compounds of formula I, wherein the compound is

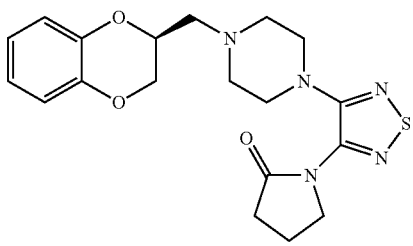 [SMILES: O=C1CCCN1c1nsnc1N1CCN(C[C@H]2COc3ccccc3O2)CC1]

or a pharmaceutically acceptable salt thereof.

In one embodiment the present disclosure relates to compounds of formula I, wherein the compound is

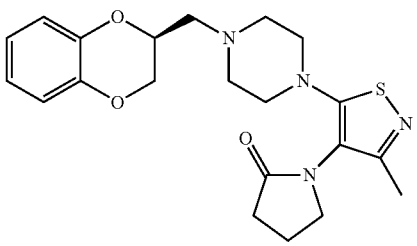 [SMILES: Cc1nsc(N2CCN(C[C@H]3COc4ccccc4O3)CC2)c1N1CCCC1=O]

or a pharmaceutically acceptable salt thereof.

In one embodiment the present disclosure relates to compounds of formula I wherein the compound is

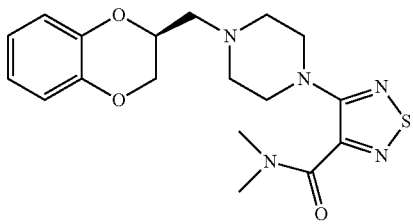 [SMILES: CN(C)C(=O)c1nsnc1N1CCN(C[C@H]2COc3ccccc3O2)CC1]

or a pharmaceutically acceptable salt thereof

The terms employed herein have the meanings indicated below.

The term "at least one" employed in the meanings below refers to one or several, such as one.

The term "hydroxy", as employed herein as such or as part of another group, refers to a —OH group.

The term "oxo", as employed herein as such or as part of another group, refers to a =O group attached as a substituent.

The term "$(C_1$-$C_6)$alkyl", as employed herein as such or as part of another group, refers to a saturated hydrocarbon group having a straight or branched moiety, containing 1, 2, 3, 4, 5 or 6 carbon atom(s). Representative examples of $(C_1$-$C_6)$alkyl include, but are not limited to, methyl, ethyl, n-propyl, iso-propyl, n-butyl, iso-butyl, sec-butyl, tert-butyl, n-pentyl, iso-pentyl, and n-hexyl.

The term "$(C_1$-$C_3)$alkyl", as employed herein as such or as part of another group, refers to a saturated hydrocarbon group having a straight or branched moiety, containing 1, 2, or 3 carbon atom(s). Representative examples of $(C_1$-$C_3)$ alkyl include, but are not limited to, methyl, ethyl, n-propyl, and iso-propyl.

The term "$(C_1$-$C_6)$alkoxy", as employed herein as such or as part of another group, refers to an $(C_1$-$C_6)$alkyl group, as defined herein, bonded to an oxygen atom. Representative examples of $(C_1$-$C_6)$alkoxy include, but are not limited to, methoxy, ethoxy, n-propoxy, n-butoxy, iso-butoxy, sec-butoxy, tert-butoxy, 2,2-dimethylpropoxy, 3-methylbutoxy, and n-hexoxy.

The term "hydroxy$(C_1$-$C_6)$alkyl", as employed herein as such or as part of another group, refers to at least one hydroxy group, as defined herein, bonded to a $(C_1$-$C_6)$alkyl group, as defined herein. Representative examples of hydroxy$(C_1$-$C_6)$alkyl include, but are not limited to, hydroxymethyl, 1-hydroxyethyl, 2-hydroxyethyl, 2,2-dihydroxyethyl, 1-hydroxypropyl, 3-hydroxypropyl, 1-hydroxy-1-methylethyl, and 1-hydroxy-1-methylpropyl.

The term "$(C_1$-$C_6)$alkoxy$(C_1$-$C_6)$alkyl", as employed herein as such or as part of another group, refers to at least one $(C_1$-$C_6)$alkoxy group, as defined herein, bonded to an $(C_1$-$C_6)$alkyl group, as defined herein. When there are several $(C_1$-$C_6)$alkoxy groups, the $(C_1$-$C_6)$alkoxy groups can be identical or different. Representative examples of $(C_1$-$C_6)$ alkoxy$(C_1$-$C_6)$alkyl include, but are not limited to, methoxymethyl, ethoxymethyl, propoxymethyl, 2-methoxyethyl, 2-ethoxyethyl, 2,2-dimethoxyethyl, 1-methyl-2-propoxyethyl, 1-methoxy-1-methylethyl, and 4-methoxybutyl.

The term "$(C_1$-$C_6)$alkyl-(C=O)", as employed herein as such or as part of another group, refers to a $(C_1$-$C_6)$alkyl group, as defined herein, bonded to a carbonyl group. Representative examples of $(C_1$-$C_6)$alkyl-(C=O) include, but are not limited to, acetyl, ethylcarbonyl, propylcarbonyl, and isopropylcarbonyl.

The term "$(C_1$-$C_6)$alkoxy-(C=O)", as employed herein as such or as part of another group, refers to a $(C_1$-$C_6)$alkoxy group, as defined herein, bonded to a carbonyl group. Representative examples of $(C_1$-$C_6)$alkoxy-(C=O) include, but are not limited to, methoxycarbonyl, ethoxycarbonyl, propoxycarbonyl, and isopropoxycarbonyl.

The term "phenyl$(C_1$-$C_6)$alkoxy", as employed herein as such or as part of another group, refers to a phenyl group, bonded to a $(C_1$-$C_6)$alkoxy group, as defined herein. Representative examples of phenyl$(C_1$-$C_6)$alkoxy include, but are not limited to, phenylmethoxy, 2-phenylethoxy, and 3-phenylpropoxy.

The term "heterocyclyl", as employed herein as such or as part of another group, refers to a 4, 5 or 6 membered saturated or unsaturated monocyclic group containing 1 or 2 ring heteroatom(s) each independently selected from N and O, or to a 9 or 10 membered saturated or unsaturated bicyclic group containing 1 or 2 ring heteroatom(s) each independently selected from N and O. Representative examples of heterocyclyl include, but are not limited to azetidin-1-yl, pyrrolidin-1-yl, oxazolidin-3-yl, imidazolidin-1-yl, piperidin-1-yl, morpholin-4-yl, pyrazol-1-yl, isoindolin-2-yl, pyridin-2-yl, pyridin-3-yl, pyridin-4-yl, pyrimidin-2-yl, and pyrimidin-4-yl.

The expression "compounds of the present disclosure" as employed herein refers to the compounds of formula I.

The "pharmaceutically acceptable salts" according to the present disclosure include therapeutically active, non-toxic, base and acid salt forms, which the compounds of formula I are able to form with both organic and inorganic bases and acids. Representative examples of pharmaceutically acceptable base addition salt forms, for example, metal or amine salts, include, but are not limited to, ammonium salts, lithium, sodium, potassium, calcium, magnesium, aluminum and zinc salts, salts with organic bases, such as N-methyl-D-glucamine, hydrabamine salts and salts with amino acids, such as arginine, lysine, and the like. Representative examples of pharmaceutically acceptable acid addition salts include, but are not limited to, chlorides, bromides, sulfates, nitrates, phosphates, sulfonates, methane sulfonates, formates, tartrates, maleates, citrates, benzoates, salicylates, ascorbates, acetates and oxalates, fumarates, and succinates.

Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols. Representative examples of pharmaceutically acceptable esters include, but are not limited to, methyl, ethyl, n-propyl, iso-propyl, n-butyl, iso-butyl, sec-butyl, tert-butyl, and benzyl esters.

The present disclosure includes all the possible geometric isomers, for example cis and trans isomers, of the compounds of formula I, as well as all the possible optical isomers, such as diastereomers and enantiomers, of the compound of formula I. Furthermore, the present disclosure includes all the individual isomers and any mixtures thereof, such as racemic mixture. The individual isomers may be obtained using the corresponding isomeric forms of the starting materials or they may be separated after the preparation of the end compound according to conventional separation methods. For the separation of optical isomers, such as enantiomers, from the mixture thereof, conventional resolution methods, for example fractional crystallization or preparative chiral chromatography, may be used.

Compounds of the invention can be prepared by a variety of synthetic routes analogously or according to the methods known in the literature using suitable starting materials. The starting materials used in the processes herein are either commercially available or can be prepared via synthetic routes known in the literature.

In general, compounds of formula I can be prepared analogously or according to the following scheme 1:

Scheme 1

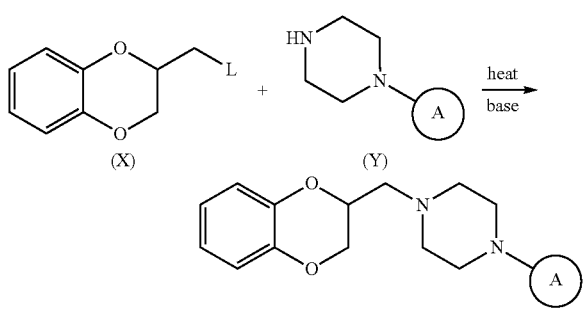

For example, suitable starting materials containing the benzodioxane moiety are compounds of formula X:

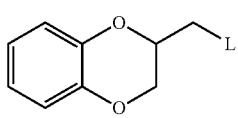

wherein L is a leaving group, e.g. halogen. Compounds of formula X can be prepared according to known methods.

The other half in formula I, i.e. piperazine ring containing compounds of formula Y, can be prepared, for example, using the methods illustrated in Schemes 2, 3, 4 and 5.

Scheme 2

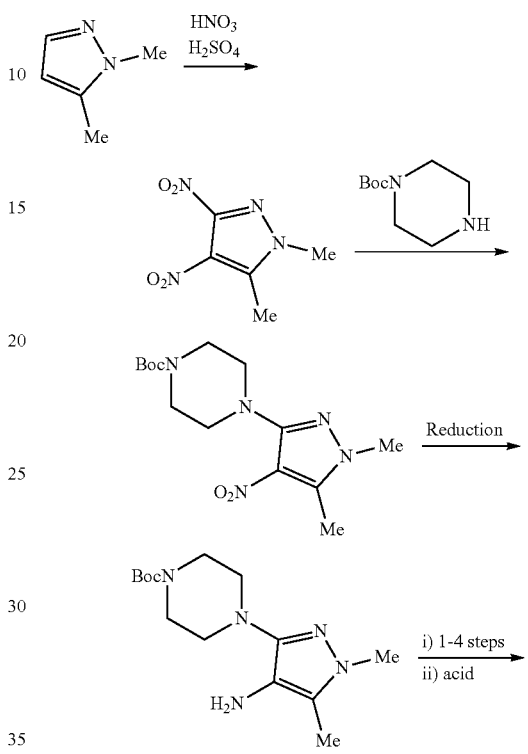

J. Gen. Chem. USSR (Engl. Transl.) 1980, 50, 1705-1708.

In scheme 2, $R_1$ is, for example, one of groups (1'), (2'), (3'), (4'), or (10').

Scheme 3

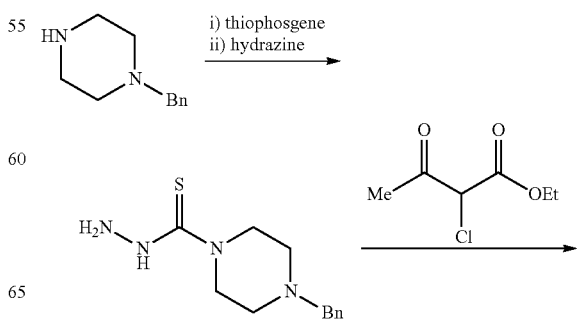

-continued
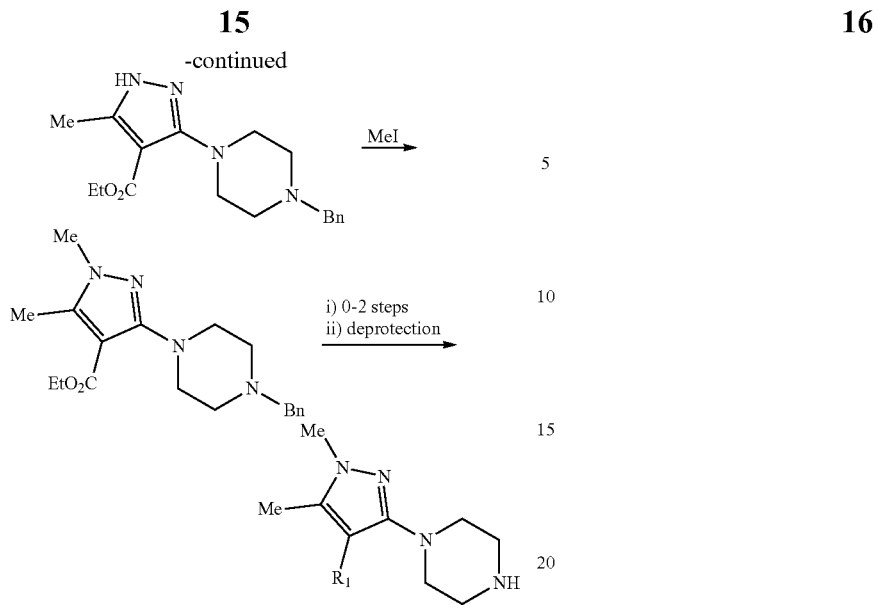
In scheme 3, $R_1$ is some noncyclic moiety, such as alkoxy($C_1$-$C_6$)alkyl, hydroxy($C_1$-$C_6$)-alkyl, or ($C_1$-$C_6$)alkoxy-(C=O)—.
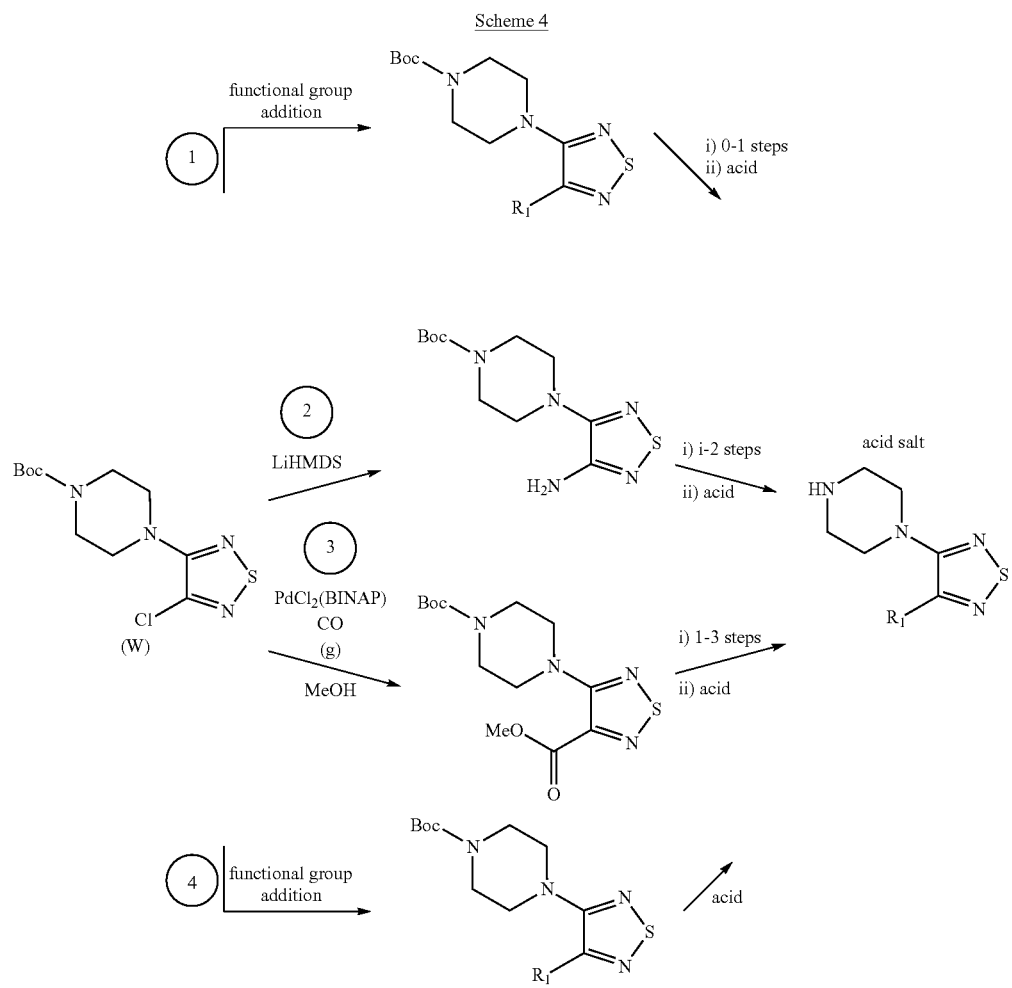

In scheme 4, the starting material W can be prepared, for example, as described in WO 2004/083235. In route 1, $R_1$ is one of groups (2'), (3'), or (4'). In route 2, $R_1$ is $R_6(C=O)-R_5N-$ or group (2'). In route 3, $R_1$ is $(C_1-C_6)$alkyl-$(C=O)-$ or $R_5R_6N-(C=O)-$. In route 4, $R_1$ is one of groups (6'), (7'), (8'), or (9').

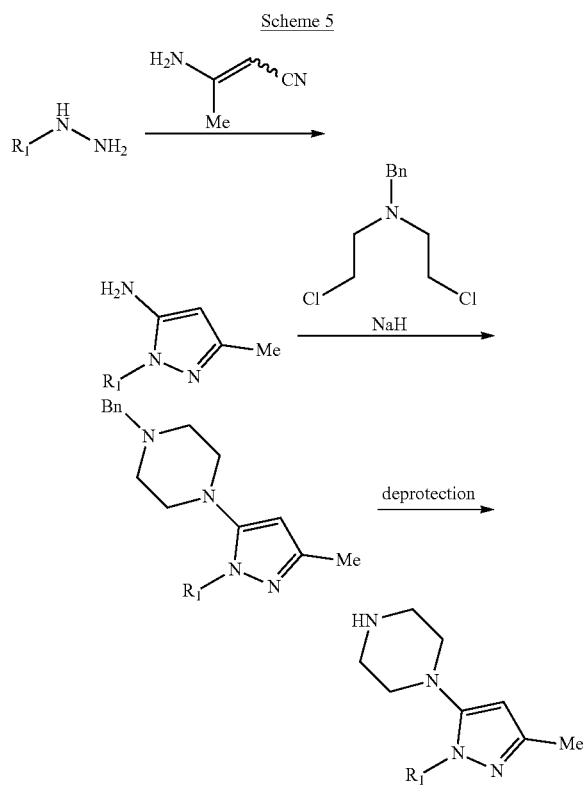

In scheme 5, $R_1$ is group (6'). In schemes 2-5 groups (2'), (3'), (4'), (6'), (7'), (8'), (9'), (10'), $R_5$ and $R_6$ are as defined above.

A person skilled in the art realizes that any starting material or intermediate in the reactions described above can be protected, if necessary, in a manner known in the art. Any protected functionality can subsequently be deprotected in a manner known in the art.

The synthetic routes described above are meant to illustrate the preparation of the compounds of formula I and the preparation is by no means limited thereto, that is, there are also other possible synthetic methods which are within the general knowledge of a person skilled in the art.

The compounds of formula I may be converted, if desired, into their pharmaceutically acceptable salt or ester form using methods known in the art.

The present disclosure will be explained in more detail by the following examples. The examples are meant for illustrating purposes only and do not limit the scope of the invention defined in the claims.

Normal phase and reverse phase flash chromatography was performed using CombiFlash instruments together with disposable Redisep columns (Teledyne ISCO). Preparative HPLC purifications were performed with a Waters preparative HPLC/MS autopurification system equipped with an XBridge Prep C18 (5 μm, 30×150 mm) column. Typically, a gradient of water/acetonitrile with 0.1% formic acid was used as eluent. Microwave heating was performed using microwave reactors from Biotage. The structures of the products were confirmed by $^1$H NMR. The spectra were measured with a Bruker Avance 400 instrument. LC-MS analyses were performed using a Waters Acquity UPLC/MS/MS with an TQ detector. For the chiral HPLC analysis, Agilent 1100-series HPLC instrument equipped with diode array detector was used.

The following general abbreviations are used: EtOAc=ethyl acetate, TFA=trifluoroacetic acid, ACN=acetonitrile, EtOH=ethanol, AcOH=acetic acid, IPA=isopropyl alcohol, DMSO-$d_6$=deuterated dimethyl sulfoxide, CDCl$_3$=deuterated chloroform, DIPEA=N,N-diisopropylethylamine, DCM=dichloromethane, DMF=N,N-dimethylformamide, MeOH=methanol, THF=tetrahydrofuran, TBAF=tetrabutylammonium fluoride, TBDMS-Cl=tert-butyldimethylsilyl chloride, HCl=hydrochloric acid, PCC=pyridinium chloro-chromate, MTBE=methyl tert-butyl ether, Pd/C=palladium on carbon, Pd$_2$(dba)$_3$=tris-(dibenzylideneacetone)dipalladium(0), RuPhos=2-dicyclohexylphosphino-2',6'-diisopropoxybiphenyl, LiHMDS=lithium hexamethyldisilazide, DMAP=4-dimethyl-aminopyridine, (Boc)$_2$O=di-tert-butyl dicarbonate, NMP=N-methyl-2-pyrrolidone, TEA=triethylamine, EDC HCl=1-ethyl-3-(3-dimethylaminopropyl)carbodiimide hydrochloride, LAH=lithium aluminum hydride, RT=room temperature, MW=microwave, LC-MS=liquid chromatography-mass spectrometry, HPLC=high performance liquid chromatography.

Preparation of the Compounds of the Present Disclosure

General Procedure A1

Piperazin-1-yl derivative (1 eq.) was dissolved in ACN. DIPEA (1 eqv) was added, followed by addition of K$_2$CO$_3$ (1.5 eqv) and (2R)-2-(bromomethyl)-2,3-dihydro-1,4-benzodioxin (1-1.4 eqv). The vial was flushed with nitrogen and sealed. The reaction mixture was heated in the microwave at 120° C. for 4 hours. The solvents were removed under reduced pressure. The procedure could be performed with only DIPEA or K$_2$CO$_3$ as a base.

General Procedure A2

Piperazin-1-yl derivative (1 eq.) was dissolved in DMF under nitrogen. (2R)-2-(bromomethyl)-2,3-dihydro-1,4-benzodioxin or (1-1.4 eq.) and Na$_2$CO$_3$ or K$_2$CO$_3$ (1.5-2.5 eq.) were added and the reaction mixture was heated at 100-120° C. for 3-4 h. The reaction mixture was allowed to cool down to RT and 1 M HCl-solution was added. The mixture was extracted with MTBE. The pH of the water phase was adjusted to 10 with Na$_2$CO$_3$ and then extracted with EtOAc. The EtOAc phase was washed with brine and concentrated under reduced pressure.

EXAMPLE 1: (S)-1-(3-(4-((2,3-Dihydrobenzo[b][1,4]dioxin-2-yl)methyl)piperazin-1-yl)-1,5-dimethyl-1H-pyrazol-4-yl)-3,3-dimethylpyrrolidine-2,5-dione Step 1: 1,5-Dimethyl-3,4-dinitro-1H-pyrazole To a solution of 100% H$_2$SO$_4$ (30 ml) was added Fuming HNO$_3$ (30 ml) at 0° C., and then stirred at 0° C. for 15 min. 1,5-Dimethyl-1H-pyrazole (10.0 g, 104.02 mmol) was added at 0° C. during 30 min. The resulting reaction mixture was warmed to RT and heated to 100° C. for 6 h. The reaction mixture was cooled down and poured into ice and the resulting mixture was stirred overnight. The precipitate (7.0 g) was filtered, washed with water and dried in vacuum. The crude product was used for next step without further purification.

Step 2: tert-Butyl 4-(1,5-dimethyl-4-nitro-1H-pyrazol-3-yl)piperazine-1-carboxylate To a solution of 1,5-dimethyl-3,4-dinitro-1H-pyrazole (7.0 g, 37.6 mmol) in isopropanol (150 ml) was added 1-Boc piperazine (21.0 g, 112.88 mmoL) at RT and the resulting reaction mixture was heated to 140° C. for 48 h. The reaction mixture was concentrated under reduced pressure. The product was purified by flash column using 2% MeOH/DCM as eluent to afford 3.3 g of pale yellow solid. LC-MS (ES+) [M+1]: 326.2

Step 3: tert-Butyl 4-(4-amino-1,5-dimethyl-1H-pyrazol-3-yl)piperazine-1-carboxylate To a solution of tert-butyl 4-(1,5-dimethyl-4-nitro-1H-pyrazol-3-yl)piperazine-1-carboxylate (3.0 g, 9.23 mmol) in THF: MeOH (1:1) (25 ml) was added $H_2O$ (5 ml), Fe (3.1 g, 55.38 mmol) and $NH_4Cl$ (2.96 g, 55.38 mmol) at RT, and the resulting reaction mixture was stirred at 70° C. for 4 h. The reaction mixture was filtered and filtrate was concentrated under reduced pressure. The product was purified by flash column using 3% MeOH/DCM as eluent to afford 2.0 g of as pale brown solid. LC-MS (ES+) [M+1]: 296.2

Step 4: tert-Butyl 4-(4-(3,3-dimethyl-2,5-dioxopyrrolidin-1-yl)-1,5-dimethyl-1H-pyrazol-3-yl)piperazine-1-carboxylate To a solution of tert-butyl 4-(4-amino-1,5-dimethyl-1H-pyrazol-3-yl)piperazine-1-carboxylate (1.0 g, 3.38 mmol) in toluene (30 ml) was added $Et_3N$ (0.71 ml, 5.01 mmol) and 3,3-dimethyldihydrofuran-2,5-dione (0.52 g, 4.06 mmol) at RT. The resulting reaction mixture was heated at 100° C. for 4 h. The reaction mixture was concentrated and water water was added. It was then extracted with EtOAc. The combined organic layers were dried over sodium sulfate and concentrated under reduced pressure to obtain crude product. The product was purified by Combi flash using 3% MeOH/DCM as eluent to afford 0.7 g of pale yellow solid. LC-MS (ES+) [M+1]: 406.3

Step 5: 1-(1,5-Dimethyl-3-(piperazin-1-yl)-1H-pyrazol-4-yl)-3,3-dimethylpyrrolidine-2,5-dione hydrochloride To a solution of tert-butyl 4-(4-(3,3-dioxopyrrolidin-1-yl)-1,5-dimethyl-1H-pyrazol-3-yl)piperazine-1-carboxylate (0.7 g, 1.73 mmol) in 1,4-Dioxane (5 ml) was added 1,4-Dioxane-HCl (4 M, 30 ml) at 0° C. and stirred at RT for 4 h. The reaction mixture was concentrated under reduced pressure. The product was purified by trituration with n-pentane and diethyl ether to afford 0.43 g of yellow solid.
LC-MS (ES+) [M+1]: 306.0

Step 6: (S)-1-(3-(4-((2,3-Dihydrobenzo[b][1,4]dioxin-2-yl)methyl)piperazin-1-yl)-1,5-dimethyl-1H-pyrazol-4-yl)-3,3-dimethylpyrrolidine-2,5-dione (S)-1-(3-(4-((2,3-Dihydrobenzo[b][1,4]dioxin-2-yl)methyl)piperazin-1-yl)-1,5-dimethyl-1H-pyrazol-4-yl)-3,3-dimethylpyrrolidine-2,5-dione was prepared according to the general procedure A1 using 1-(1,5-dimethyl-3-(piperazin-1-yl)-1H-pyrazol-4-yl)-3,3-dimethylpyrrolidine-2,5-dione, HCl (100 mg, 0.293 mmol), DIPEA (0.051 ml, 0.293 mmol), $K_2CO_3$ (60.6 mg, 0.439 mmol), (2R)-2-(bromomethyl)-2,3-dihydro-1,4-benzodioxin (67.0 mg, 0.293 mmol) and ACN (1.4 ml). The product was purified by flash chromatography using 2% MeOH in DCM as eluent to afford 51 mg of oil. LC-MS (ES+) [M+1]: 454.2,
$^1$H NMR (400 MHz, $CDCl_3$) δ ppm 1.36-1.49 (m, 6H) 1.92-2.04 (m, 3H) 2.51-2.68 (m, 6H) 2.69-2.73 (m, 2H) 2.97-3.16 (m, 4H) 3.62-3.73 (m, 3H) 3.90-4.06 (m, 1H) 4.21-4.37 (m, 2H) 6.75-6.96 (m, 4H).

EXAMPLE 2: (S)-2-(3-(4-((2,3-Dihydrobenzo[b][1,4]dioxin-2-yl)methyl)piperazin-1-yl)-1,5-dimethyl-1H-pyrazol-4-yl)isoindoline-1,3-dione

Step 1: tert-Butyl 4-(4-(1,3-dioxoisoindolin-2-yl)-1,5-dimethyl-1H-pyrazol-3-yl)piperazine-1-carboxylate tert-Butyl 4-(4-(1,3-dioxoisoindolin-2-yl)-1,5-dimethyl-1H-pyrazol-3-yl)piperazine-1-carboxylate was prepared as in intermediate example 1 step 4 using tert-butyl 4-(4-amino-1,5-dimethyl-1H-pyrazol-3-yl)piperazine-1-carboxylate (1.5 g, 5.08 mmol), Phallic anhydride (0.9 g, 6.09 mmol), $Et_3N$ (1.06 ml, 7.62 mmol) and toluene (40 ml). The product was purified by Combi flash using 3% MeOH in DCM as eluent to afford 800 mg of pale yellow solid. LC-MS (ES+) [M+1]: 426.2

Step 2: 2-(1,5-Dimethyl-3-(piperazin-1-yl)-1H-pyrazol-4-yl)isoindoline-1,3-dione hydrochloride 2-(1,5-Dimethyl-3-(piperazin-1-yl)-1H-pyrazol-4-yl)isoindoline-1,3-dione hydrochloride was prepared as in intermediate example 1 step 5 using tert-butyl 4-(4-(1,3-dioxoisoindolin-2-yl)-1,5-dimethyl-1H-pyrazol-3-yl)piperazine-1-carboxylate (0.8 g, 1.88 mmol), 1,4-dioxane-HCl (4 M, 30 ml) and 1,4-dioxane (5 ml). The product was purified by trituration with n-pentane and diethyl ether to afford 0.45 g of pale yellow solid. LC-MS (ES+) [M+1]: 326.0

Step 3: (S)-2-(3-(4-((2,3-Dihydrobenzo[b][1,4]dioxin-2-yl)methyl)piperazin-1-yl)-1,5-dimethyl-1H-pyrazol-4-yl)isoindoline-1,3-dione (S)-2-(3-(4-((2,3-Dihydrobenzo[b][1,4]dioxin-2-yl)methyl)piperazin-1-yl)-1,5-dimethyl-1H-pyrazol-4-yl)isoindoline-1,3-dione was prepared according to the general procedure A1 using 2-(1,5-dimethyl-3-(piperazin-1-yl)-1H-pyrazol-4-yl)isoindoline-1,3-dione, HCl (100 mg, 0.276 mmol), (2R)-2-(bromomethyl)-2,3-dihydro-1,4-benzodioxin (63.3 mg, 0.276 mmol), DIPEA (0.048 ml, 0.276 mmol), $K_2CO_3$ (57.3 mg, 0.415 mmol) and ACN (1.4 ml). The product was purified by flash chromatography using 2% MeOH in DCM as eluent to afford 64 mg of yellowish oil. LC-MS (ES+) [M+1]: 474.2,
$^1$H NMR (400 MHz, $CDCl_3$) δ ppm 1.96-2.09 (m, 3H) 2.43-2.72 (m, 6H) 3.11 (t, 4H) 3.70 (s, 3H) 3.86-4.01 (m, 1H) 4.17-4.35 (m, 2H) 6.73-6.92 (m, 4H) 7.74-7.88 (m, 2H) 7.89-8.02 (m, 2H).

EXAMPLE 3: (S)-5-(4-((2,3-Dihydrobenzo[b][1,4]dioxin-2-yl)methyl)piperazin-1-yl)-2-methyloxazole-4-carbonitrile

Step 1: 2-Amino-3,3-dichloroacrylonitrile

To an ice cold stirred solution of 2,2-dichloroacetonitrile (5.0 g, 45.47 mmol) and acetone cyanohydrin (4.56 ml, 50.03 mol) in a mixture of Et$_2$O and ACN (25 ml, 1:4) was added KCN (60 mg, 0.909 mmol) and stirred at 0° C. for 10 h. Solvent was evaporated under reduced pressure. Et$_2$O (15 ml) and activated charcoal (300 mg) was added and the mixture was stirred for 10 mins, filtered through a pad of celite and washed with Et$_2$O (5 ml). The filtrate was concentrated under reduced pressure to obtain 4.1 g of brown solid.

Step 2: N-(2,2-dichloro-1-cyanovinyl)acetamide

A solution of 2-amino-3,3-dichloroacrylonitrile (4.0 g, 29.20 mmol) in a mixture of acetic anhydride (5.51 ml, 58.41 mmol) and acetic acid (0.08 ml, 1.46 mmol) was allowed to stir at RT for 16 h. Reaction mixture was diluted with DCM (200 ml) and washed with water (2×100 ml). The organic layer was dried over anhydrous Na$_2$SO$_4$ and under reduced pressure. The product was purified by triturating with cold Et$_2$O to obtain 3.6 g of light brown solid.

Step 3: tert-Butyl 4-(4-cyano-2-methyloxazol-5-yl)piperazine-1-carboxylate

To an ice cold stirred solution of N-(2,2-dichloro-1-cyanovinyl)acetamide (4.5 g, 25.14 mmol) in ACN (100 ml) was added Et$_3$N (7.0 ml, 50.28 mmol) and tert-butyl piperazine-1-carboxylate (5.6 g, 30.17 mmol) and stirred at RT for 16 h. Solvent was evaporated under reduced pressure. The residue was diluted with EtOAc (400 ml) and washed with 10% aqueous NaHCO$_3$ solution (2×100 ml). The organic layer was dried over anhydrous Na$_2$SO$_4$ and concentrated under reduced pressure. The product was purified by column chromatography on silica gel 100-200 mesh and eluted with 40% EtOAc in pet ether to obtain 2.1 g of off-white solid. LC-MS (ES+) [M+1]: 293.2

Step 4: 2-Methyl-5-(piperazin-1-yl)oxazole-4-carbonitrile hydrochloride

To a solution of tert-butyl 4-(4-cyano-2-methyloxazol-5-yl)piperazine-1-carboxylate (0.549 g, 1.88 mmol) in EtOAc (10 ml) was added 1,4-dioxane-HCl (4 M, 2.3 ml) and the reaction mixture was stirred overnight. The solvents were evaporated under reduced pressure and the product was purified by trituration with MTBE to afford 340 mg of white solid. LC-MS (ES+) [M+1]: 193.1

Step 5: (S)-5-(4-((2,3-Dihydrobenzo[b][1,4]dioxin-2-yl)methyl)piperazin-1-yl)-2-methyloxazole-4-carbonitrile (S)-5-(4-((2,3-Dihydrobenzo[b][1,4]dioxin-2-yl)methyl)piperazin-1-yl)-2-methyloxazole-4-carbonitrile was prepared according to the general procedure A1 using 2-methyl-5-(piperazin-1-yl)oxazole-4-carbonitrile, HCl (150 mg, 0.655 mmol), (2R)-2-(bromomethyl)-2,3-dihydro-1,4-benzodioxin (150 mg, 0.655 mmol), DIPEA (0.114 ml, 0.655 mmol), K$_2$CO$_3$ (136 mg, 0.982 mmol) and ACN (1.4 ml). The product was purified by flash chromatography using 10-70% gradient of EtOAc in heptane to afford 82 mg of colourless oil. LC-MS (ES+) [M+1]: 342.2, $^1$H NMR (400 MHz, CDCl$_3$) δ ppm 2.34 (s, 3H) 2.58-2.84 (m, 6H) 3.50-3.63 (m, 4H) 3.97-4.09 (m, 1H) 4.25-4.39 (m, 2H) 6.77-6.96 (m, 4H).

EXAMPLE 4: (S)-1-(3-(4-((2,3-Dihydrobenzo[b][1,4]dioxin-2-yl)methyl)piperazin-1-yl)-1,5-dimethyl-1H-pyrazol-4-yl)azetidin-2-one Step 1: Ethyl 3-oxopropanoate To a stirred solution of ethyl 3,3-diethoxypropanoate (2.0 g, 10.51 mmol) in THF (5.0 ml) was added 4.0 M HCl (20.0 ml) at 0° C. After the addition, the reaction mixture was warmed to RT and stirred for 8 h. The reaction mixture was diluted with diethyl ether and organic layer was dried over Na$_2$SO$_4$, concentrated under reduced pressure to obtain 0.3 g of colourless oil. The crude product was used for next step without further purification.

Step 2: tert-Butyl 4-(4-((3-ethoxy-3-oxopropyl)amino)-1,5-dimethyl-1H-pyrazol-3-yl)piperazine-1-carboxylate tert-Butyl 4-(4-((3-ethoxy-3-oxopropyl)amino)-1,5-dimethyl-1H-pyrazol-3-yl)piperazine-1-carboxylate was prepared as in intermediate example 3 step 3 using tert-butyl 4-(4-amino-1,5-dimethyl-1H-pyrazol-3-yl)piperazine-1-carboxylate (3.0 g, 10.17 mmol) ethyl 3-oxopropanoate (1.18 g, 10.17 mmol), NaCNBH$_3$ (0.96 g, 15.25 mmol) and 1,2-dichloro ethane (100 ml). The product was purified by column chromatography using 100-200 mesh silica gel and eluted on 2% MeOH/DCM. to afford 1.2 g of brown liquid. LC-MS (ES+) [M+1]: 396.3

Step 3: tert-Butyl 4-(1,5-dimethyl-4-(2-oxoazetidin-1-yl)-1H-pyrazol-3-yl)piperazine-1-carboxylate To a solution of tert-butyl 4-(4-((3-ethoxy-3-oxopropyl)amino)-1,5-dimethyl-1H-pyrazol-3-yl)piperazine-1-carboxylate (1.5 g, 3.79 mmol) in dry THF (25.0 ml) was added MeMgBr (3.0 M in diethylether (1.9 ml) at 0° C. The reaction mixture was stirred at RT for 8 h. The reaction mixture was quenched with NH$_4$C$_1$, then extracted with EtOAc. The combined organic layers were dried over sodium sulfate and concentrated under reduced pressure. The product was purified by column chromatography using 100-200 mesh silica gel and eluted on 2% MeOH/DCM to afford 0.13 g of brown solid. LC-MS (ES+) [M+1]: 350.3

Step 4: 1-(1,5-Dimethyl-3-(piperazin-1-yl)-1H-pyrazol-4-yl)azetidin-2-one TFA

To a solution of tert-butyl 4-(1,5-dimethyl-4-(2-oxoazetidin-1-yl)-1H-pyrazol-3-yl)piperazine-1-carboxylate (0.37 g, 1.06 mmol) in DCM (5.0 ml) was added TFA (0.35 ml) at 0° C. and allowed to stir at RT for 16 h. The reaction mixture was concentrated under reduced pressure. The product was purified by trituration with n-pentane to afford 0.360 g of pale brown liquid. LC-MS (ES+) [M+1]: 250.1

Step 5: (S)-1-(3-(4-((2,3-Dihydrobenzo[b][1,4]dioxin-2-yl)methyl)piperazin-1-yl)-1,5-dimethyl-1H-pyrazol-4-yl)azetidin-2-one (S)-1-(3-(4-((2,3-Dihydrobenzo[b][1,4]dioxin-2-yl)methyl)piperazin-1-yl)-1,5-dimethyl-1H-pyrazol-4-yl)azetidin-2-one was prepared according to the general procedure A1 using 1-(1,5-dimethyl-3-(piperazin-1-yl)-1H-pyrazol-4-yl)azetidin-2-one, TFA (200 mg, 0.700 mmol), (2R)-2-(bromomethyl)-2,3-dihydro-1,4-benzodioxin (160 mg, 0.700 mmol), DIPEA (0.122 ml, 0.700 mmol), K$_2$CO$_3$ (145 mg, 1.050 mmol) and ACN (4 ml). The product was purified by flash chromatography using 2-4% gradient of MeOH in DCM as eluent to afford 71 mg of oil. LC-MS (ES+) [M+1]: 396.2, $^1$H NMR (400 MHz, CDCl$_3$) δ ppm 2.15 (s, 3H) 2.54-2.77 (m, 6H) 3.01-3.24 (m, 6H) 3.44-3.54 (m, 2H) 3.59 (s, 3H) 3.95-4.13 (m, 1H) 4.23-4.42 (m, 2H) 6.76-6.97 (m, 4H).

EXAMPLE 5: (S)-3-(3-(4-((2,3-Dihydrobenzo[b][1,4]dioxin-2-yl)methyl)piperazin-1-yl)-1,5-dimethyl-1H-pyrazol-4-yl)oxazolidin-2-one Step 1: (Allyloxy)(tert-butyl)dimethylsilane To an ice cold stirred solution of prop-2-en-1-ol (10 g, 172.41 mmol) in DMF (100 ml) were added imidazole (23.4 g, 344.82 mmol) and TBDMS-Cl (31.1 g, 206.89 mmol). The reaction mixture was stirred at RT for 16 h. The reaction mixture was quenched with water (600 ml) and extracted with diethyl ether (2×300 ml). The combined organic layer was washed with water and brine. The organic layer was dried over anhydrous Na$_2$SO$_4$ and concentrated under reduced pressure to obtain 15.0 g of oil. The crude product was used for next step without further purification.

Step 2: 2-((tert-Butyldimethylsilyl)oxy)acetaldehyde

To a solution of (allyloxy)(tert-butyl)dimethylsilane (1.0 g, 172.31 mmol) in diethyl ether and t-BuOH was added NaIO$_4$ in water at room temperature followed by OsO$_4$ (0.02 M in water) at 0° C. The resulting reaction mixture was stirred at room temperature for 3 h. The reaction mixture was quenched with Na$_2$SO$_3$ at 0° C. and extracted with diethyl ether (2×20 ml). The combined organic extracts were washed with water and brine. The organic layer was dried over anhydrous Na$_2$SO$_4$ and concentrated under reduced pressure to obtain 1.0 g of crude product as liquid. The crude product was used for next step without further purification.

Step 3: tert-Butyl 4-(4-((2-((tert-butyldimethylsilyl)oxy)ethyl)amino)-1,5-dimethyl-1H-pyrazol-3-yl)piperazine-1-carboxylate To an ice cold stirred solution of tert-butyl 4-(4-amino-1,5-dimethyl-1H-pyrazol-3-yl)piperazine-1-carboxylate (100 mg, 0.338 mmol) in 1, 2-dichloro ethane (5.0 ml) was added 2-((tert-butyldimethylsilyl)oxy)acetaldehyde (58 mg, 3.389 mmol) and stirred for 10 min. NaBH(OAc)$_3$ (143 mg, 0.677 mmol) was added to reaction mixture in portions and reaction was stirred at room temperature for 16 h The reaction mixture was diluted with DCM, washed with water and brine. The organic layer was dried over anhydrous Na$_2$SO$_4$ and concentrated under reduced pressure. The product was purified by flash column using ethyl acetate in pet ether as eluent to obtain 50 mg of the desired product. LC-MS (ES+) [M+1]: 454.4

Step 4: tert-Butyl 4-(4-((2-hydroxyethyl)amino)-1,5-dimethyl-1H-pyrazol-3-yl)piperazine-1-carboxylate To an ice cold stirred solution of tert-butyl 4-(4-((2-((tert-butyldimethylsilyl)oxy)ethyl)-amino)-1,5-dimethyl-1H-pyrazol-3-yl)piperazine-1-carboxylate (0.87 g, 1.92 mmol) in THF (10 ml) was added TBAF (2.88 ml, 2.88 mmol) and stirred at 0° C.→RT for 2 h. The reaction mixture was diluted with EtOAc, washed with water and brine. The organic layer was dried over anhydrous Na$_2$SO$_4$ and concentrated under reduced pressure. The product was purified by flash column using ethyl acetate in pet ether as eluent to obtain 520 mg of the desired product. LC-MS (ES+) [M+1]: 340.3

Step 5: tert-Butyl 4-(1,5-dimethyl-4-(2-oxooxazolidin-3-yl)-1H-pyrazol-3-yl)piperazine-1-carboxylate To a solution of tert-butyl 4-(4-((2-hydroxyethyl)amino)-1,5-dimethyl-1H-pyrazol-3-yl)piperazine-1-carboxylate (1.0 g, 2.949 mmol) in dry DMF (10 ml) were added DIPEA (2.11 ml, 11.799 mmol) and CDI (1.43 g, 8.849 mmol) at RT in a seal tube. The reaction mixture was heated to 100° C. for 16 h. The reaction mixture was quenched with water (80 ml) and extracted with EtOAc (2×60 ml). The combined organic extracts were washed with water, brine. The organic layer was dried over anhydrous Na$_2$SO$_4$ and concentrated under reduced pressure. The product was purified by combi-flash using ammonium acetate in water and MeOH as eluent to obtain 440 mg of solid. LC-MS (ES+) [M+1]: 366.2

Step 6: 3-(1,5-Dimethyl-3-(piperazin-1-yl)-1H-pyrazol-4-yl)oxazolidin-2-one hydrochloride 3-(1,5-Dimethyl-3-(piperazin-1-yl)-1H-pyrazol-4-yl)oxazolidin-2-one hydrochloride was prepared as in intermediate example 1 step 5 using tert-butyl 4-(1,5-dimethyl-4-(2-oxooxazolidin-3-yl)-1H-pyrazol-3-yl)piperazine-1-carboxylate (400 mg, 1.095 mmol) and 1,4-dioxane-HCl (4 M, 20 ml). The product was purified by trituration with n-pentane to afford 330 mg of yellow solid. LC-MS (ES+) [M+1]: 266.3

Step 7: (S)-3-(3-(4-((2,3-Dihydrobenzo[b][1,4]dioxin-2-yl)methyl)piperazin-1-yl)-1,5-dimethyl-1H-pyrazol-4-yl)oxazolidin-2-one (S)-3-(3-(4-((2,3-Dihydrobenzo[b][1,4]dioxin-2-yl)methyl)piperazin-1-yl)-1,5-dimethyl-1H-pyrazol-4-yl)oxazolidin-2-one was prepared according to the general procedure A2 using 3-(1,5-dimethyl-3-(piperazin-1-yl)-1H-pyrazol-4-yl)oxazolidin-2-one, HCl (132 mg, 0.437 mmol), (2R)-2-(bromomethyl)-2,3-dihydro-1,4-benzodioxin (100 mg, 0.437 mmol), Na$_2$CO$_3$ (69.4 mg, 0.655 mmol) and DMF (2 ml). The product was purified by reversed phase flash chromatography using 0.1% HCOOH/ACN as eluent to afford 53.4 mg of white solid. LC-MS (ES+) [M+1]: 414.2, $^1$H NMR (400 MHz, CDCl$_3$) δ ppm 2.13 (s, 3H) 2.50-2.85 (m, 6H) 3.06-3.30 (m, 4H) 3.63 (s, 3H) 3.78-3.91 (m, 2H) 4.02 (dd, 1H) 4.25-4.42 (m, 2H) 4.43-4.54 (m, 2H) 6.78-6.94 (m, 4H).

EXAMPLE 6: (S)-1-(3-(4-((2,3-Dihydrobenzo[b][1,4]dioxin-2-yl)methyl)piperazin-1-yl)-1,5-dimethyl-1H-pyrazol-4-yl)-4,4-dimethylimidazolidin-2-one Step 1: Benzyl (1-hydroxy-2-methylpropan-2-yl)carbamate To a stirred solution of 2-amino-2-methylpropan-1-ol (3.0 g, 33.65 mmol) in DCM (200 ml) was added aqueous NaHCO$_3$ (8.4 g, 100.95 mmol in 100 ml water) at 0° C. and 50% wt-CbzCl in toluene (11.4 g, 33.65 mmol) was added drop wise over 15 min. After the addition, the reaction mixture was warmed to RT and stirred for 16 h. The reaction mixture was diluted with DCM and organic layer was dried over Na$_2$SO$_4$, concentrated under reduced pressure. The product was purified by flash column using 20% ethyl acetate in pet ether as eluent to afford 4.2 g of colorless oil. LC-MS (ES+) [M+1]: 224.2

Step 2: Benzyl (2-methyl-1-oxopropan-2-yl)carbamate

To a stirred solution of benzyl (1-hydroxy-2-methylpropan-2-yl)carbamate (4.0 g, 17.91 mmol) in DCM (40.0 ml) was added PCC (7.72 g, 35.83 mmol) and silica gel (10.0 g) at 0° C. and then stirred at RT for 16 h. The reaction mixture was diluted with DCM and filtered through Celite pad; the filtrate was concentrated under reduced pressure. The product was purified by flash column using 20% ethyl acetate in pet ether as eluent to afford 2.1 g of pale yellow liquid. LC-MS (ES+) [M+1]: 222.2

Step 3: tert-Butyl 4-(4-((2-(((benzyloxy)carbonyl)amino)-2-methylpropyl)amino)-1,5-dimethyl-1H-pyrazol-3-yl)piperazine-1-carboxylate tert-Butyl 4-(4-((2-(((benzyloxy)carbonyl)amino)-2-methylpropyl)amino)-1,5-dimethyl-1H-pyrazol-3-yl)piperazine-1-carboxylate was prepared as in intermediate example 3 step 3 using tert-butyl 4-(4-amino-1,5-dimethyl-1H-pyrazol-3-yl)piperazine-1-carboxylate (1.5 g, 5.08 mmol), benzyl (2-methyl-1-oxopropan-2-yl)carbamate (1.12 g, 5.08 mmol) NaBH(OAC)$_3$ (2.15 g, 10.17 mmol) and 1, 2-dichloro ethane (50 ml). The product was purified by column chromatography using 100-200 mesh silica gel and eluted on 40% EtOAc in pet ether to afford 2.2 g of brown liquid. LC-MS (ES+) [M+1]: 501.4

Step 4: tert-Butyl 4-(4-((2-amino-2-methylpropyl)amino)-1,5-dimethyl-1H-pyrazol-3-yl)piperazine-1-carboxylate To solution of tert-Butyl 4-(4-((2-(((benzyloxy)carbonyl)amino)-2-methylpropyl)amino)-1,5-dimethyl-1H-pyrazol-3-yl)piperazine-1-carboxylate (2.0 g, 4.00 mmol) in EtOAc (60 ml) was added 10% Pd—C (1.0 g) at RT and the reaction mixture was hydrogenated with H$_2$ gas under balloon pressure stirring for 18 h. The reaction mixture was filtered and the filtrate was concentrated under reduced pressure. The product was purified by trituration with n-pentane and diethyl ether to afford 0.7 g of brown solid.

Step 5: tert-Butyl 4-(4-(3,3-dimethyl-5-oxopyrazolidin-1-yl)-1,5-dimethyl-1H-pyrazol-3-yl)piperazine-1-carboxylate To a solution of tert-butyl 4-(4-((2-amino-2-methylpropyl)amino)-1,5-dimethyl-1H-pyrazol-3-yl)piperazine-1-carboxylate (0.6 g, 1.63 mmol) in DCM (30 ml) was added Et$_3$N (0.46 ml, 3.27 mmol) at 0° C., followed by triphosgene (0.16 g, 0.54 mmol) and stirred at RT for 2 h. The reaction mixture was quenched with aq.NaHCO$_3$ and diluted with DCM, combined organic layer was washed with water and dried over sodium sulfate, and then concentrated under reduced pressure. The product was purified by washing with Ether/pentane to afford 0.2 g of off white solid. LC-MS (ES+) [M+1]: 393.3

Step 6: 1-(1,5-Dimethyl-3-(piperazin-1-yl)-1H-pyrazol-4-yl)-4,4-dimethylimidazolidin-2-one hydrochloride 1-(1,5-Dimethyl-3-(piperazin-1-yl)-1H-pyrazol-4-yl)-4,4-dimethylimidazolidin-2-one hydrochloride was prepared as in intermediate example 1 step 5 using tert-butyl 4-(4-(3,3-dimethyl-5-oxopyrazolidin-1-yl)-1,5-dimethyl-1H-pyrazol-3-yl)piperazine-1-carboxylate (0.5 g, 1.27 mmol), 1,4-dioxane-HCl (4 M, 30 ml) and dioxane (5 ml). The product was purified by trituration with n-pentane and diethyl ether to afford 390 mg of off-white solid. LC-MS (ES+) [M+1]: 293.1

Step 7: (S)-1-(3-(4-((2,3-Dihydrobenzo[b][1,4]dioxin-2-yl)methyl)piperazin-1-yl)-1,5-dimethyl-1H-pyrazol-4-yl)-4,4-dimethylimidazolidin-2-one (S)-1-(3-(4-((2,3-Dihydrobenzo[b][1,4]dioxin-2-yl)methyl)piperazin-1-yl)-1,5-dimethyl-1H-pyrazol-4-yl)-4,4-dimethylimidazolidin-2-one was prepared according to the general procedure A2 using 1-(1,5-dimethyl-3-(piperazin-1-yl)-1H-pyrazol-4-yl)-4,4-dimethyl-imidazolidin-2-one, HCl (137 mg, 0.417 mmol), (2R)-2-(bromomethyl)-2,3-dihydro-1,4-benzodioxin (100 mg, 0.437 mmol), Na$_2$CO$_3$ (69.4 mg, 0.655 mmol) and DMF (2 ml). The product was purified reversed phase flash chromatography using 0.1% HCOOH/W ACN as eluent to afford 36.6 mg of white solid. LC-MS (ES+) [M+1]: 441.3, $^1$H NMR (400 MHz, CDCl$_3$) δ ppm 1.38 (s, 6H) 2.12 (s, 3H) 2.49-2.82 (m, 6H) 3.07-3.29 (m, 4H) 3.44 (s, 2H) 3.61 (s, 3H) 4.00 (dd, 1H) 4.25-4.39 (m, 2H) 4.48 (s, 1H) 6.72-7.00 (m, 4H).

EXAMPLE 7: (S)-1-(3-(4-((2,3-Dihydrobenzo[b][1,4]dioxin-2-yl)methyl)piperazin-1-yl)-1,5-dimethyl-1H-pyrazol-4-yl)-3,4,4-trimethylimidazolidin-2-one Step 1: tert-Butyl 4-(1,5-dimethyl-4-(3,4,4-trimethyl-2-oxoimidazolidin-1-yl)-1H-pyrazol-3-yl)piperazine-1-carboxylate To a solution of tert-butyl 4-(4-(4,4-dimethyl-2-oxoimidazolidin-1-yl)-1,5-dimethyl-1H-pyrazol-3-yl)piperazine-1-carboxylate (0.7 g, 1.78 mmol) in DMF (20 ml) was added 60% NaH (0.43 g, 17.85 mmol) at 0° C., and allowed stir at same temperature for 15 min and was added MeI (0.11 ml, 1.78 mmol). The reaction mixture was gradually warmed to RT and stirred for 2 h. The reaction mixture was concentrated under reduced pressure. Evaporation residue was diluted with EtOAc and washed with water. The organic layer was dried over sodium sulfate and concentrated under reduced pressure. The product was purified by flash column using 2% MeOH in DCM as eluent to afford 0.3 g of viscous liquid. LC-MS (ES+) [M+1]: 407.3

Step 2: 1-(1,5-Dimethyl-3-(piperazin-1-yl)-1H-pyrazol-4-yl)-3,4,4-trimethyl-imidazolidin-2-one hydrochloride 1-(1,5-Dimethyl-3-(piperazin-1-yl)-1H-pyrazol-4-yl)-3,4,4-trimethylimidazolidin-2-one hydrochloride was prepared as in intermediate example 1 step 5 using tert-butyl 4-(1,5-dimethyl-4-(3,4,4-trimethyl-2-oxoimidazolidin-1-yl)-1H-pyrazol-3-yl)piperazine-1-carboxylate (0.3 g, 0.74 mmol), 1,4-dioxane-HCl (4 M, 30 ml) and dioxane (5 ml). The product was purified by trituration with n-pentane and diethyl ether to afford 180 mg of off-white solid. LC-MS (ES+) [M+1]: 307.3

Step 3: (S)-1-(3-(4-((2,3-Dihydrobenzo[b][1,4]dioxin-2-yl)methyl)piperazin-1-yl)-1,5-dimethyl-1H-pyrazol-4-yl)-3,4,4-trimethylimidazolidin-2-one (S)-1-(3-(4-((2,3-Dihydrobenzo[b][1,4]dioxin-2-yl)methyl)piperazin-1-yl)-1,5-dimethyl-1H-pyrazol-4-yl)-3,4, 4-trimethylimidazolidin-2-one was prepared according to the general procedure A2 using 1-(1,5-dimethyl-3-(piperazin-1-yl)-1H-pyrazol-4-yl)-3,4,4-trimethylimidazolidin-2-one, HCl (150 mg, 0.437 mmol), (2R)-2-(bromomethyl)-2,3-dihydro-1,4-benzodioxin (100 mg, 0.437 mmol), Na$_2$CO$_3$ (69.4 mg, 0.655 mmol) and DMF (2 ml). The product was purified reversed phase flash chromatography using 0.1% HCOOH/ACN as eluent to afford 36.6 mg of white solid. LC-MS (ES+) [M+1]: 455.3, $^1$H NMR (400 MHz, CDCl$_3$) δ ppm 1.31 (s, 6H) 2.05-2.11 (m, 3H) 2.53-2.75 (m, 6H) 2.77 (s, 3H) 3.15 (t, 4H) 3.34 (s, 2H) 3.61 (s, 3H) 4.00 (dd, 1H) 4.27-4.37 (m, 2H) 6.78-6.92 (m, 4H).

EXAMPLE 8: (S)-4-(4-((2,3-Dihydrobenzo[b][1,4]dioxin-2-yl)methyl)piperazin-1-yl)-5-(methoxymethyl)thiazole Step 1: 2,4-Dibromothiazole-5-carbaldehyde A mixture of thiazolidine-2,4-dione (15.0 g, 128 mmol), POBr$_3$ (183.6 g, 640 mmol) and DMF (10.8 ml, 140.9 mmol) was heated to 75° C. for 1 h and then at 100° C. for 5 h. The reaction mixture was cooled to room temperature, diluted with CH$_2$Cl$_2$ and washed with saturated NaHCO$_3$ solution, filtered and concentrated. Trituration of the evaporation residue with petroleum ether afforded 8.0 g of 2,4-dibromothiazole-5-carbaldehyde 8.0 g as black solid.

Step 2: (2,4-Dibromothiazol-5-yl)methanol

To a solution of 2,4-dibromothiazole-5-carbaldehyde (8.0 g, 29.5 mmol) in methanol was added NaBH$_4$ (1.16 g, 29.5 mmol) at 0° C. and the reaction was stirred for 16 at room temperature. The reaction mixture was concentrated, quenched with saturated NH$_4$Cl solution, basified with 0.1N NaOH solution and extracted with ethyl acetate. The combined organic layers were dried (Na$_2$SO$_4$), concentrated. Purification of the evaporation residue by column chromatography (30% EtOAc in petroleum ether) afforded 6.0 g of (2,4-dibromothiazol-5-yl)methanol as yellow solid.

Step 3: (4-Bromothiazol-5-yl)methanol

To a solution of (2,4-dibromothiazol-5-yl)methanol (15.0 g, 54.9 mmol) in methanol (400 mL) was added 10% Pd/C (1.12 g) followed by Na$_2$CO$_3$ (13.0 g) at RT. The reaction mixture was hydrogenated at 60 psi for 2 days at room temperature. The reaction mixture was filtered, washed with ethyl acetate and concentrated. Purification of the evaporation residue by column chromatography (30% EtOAc in petroleum ether) afforded 9.3 g of (4-bromothiazol-5-yl)methanol as yellow liquid.

Step 4: 4-Bromo-5-(methoxymethyl)thiazole

Sodium hydride (1.67 g, 69.97 mmol, 60%) was washed with dry n-pentane and dried under vacuum. Dry THF (300 mL) was added and the mixture was cooled in ice/water bath. A solution of (4-bromothiazol-5-yl)methanol (9.0 g, 46.7 mmol) in THF (100 mL) was added drop wise and the reaction mixture was stirred for 30 minutes. Methyl iodide (7.9 g, 56.0 mmol) was added at 0° C. and reaction mixture was stirred for 4 h at room temperature. Ice cold water was added and the mixture was extracted with EtOAc. Combined organic layers were dried (Na$_2$SO$_4$) and concentrated. The evaporation residue containing 4-bromo-5-(methoxymethyl) thiazole was directly taken for next step without further purification. Brown liquid. 8.0 g Step 5: 5-(Methoxymethyl)-4-(piperazin-1-yl)thiazole A mixture of 4-bromo-5-(methoxymethyl)thiazole (3.5 g, 16.8 mmol) and piperazine (1.74 g, 20.2 mmol) in toluene was degassed with argon for 20 min. To the mixture was added t-BuONa (3.23 g, 33.6 mmol) followed by Pd$_2$(dba)$_3$ (0.77 g, 0.84 mmol), RuPhos (0.78 g, 1.68 mmol) at room temperature and the reaction mixture was heated to reflux for 12 h The reaction mixture was filtered, and concentrated. Purification of the evaporation residue by column chromatography (20% MeOH/CH$_2$Cl$_2$) afforded 0.4 g of 5-(methoxymethyl)-4-(piperazin-1-yl)thiazole as brown solid. m/z [M+1]: 214.1.

Step 6: (S)-4-(4-((2,3-Dihydrobenzo[b][1,4]-dioxin-2-yl)methyl)piperazin-1-yl)-5-(methoxymethyl)thiazole (S)-4-(4-((2,3-dihydrobenzo[b][1,4]dioxin-2-yl)methyl)piperazin-1-yl)-5-(methoxymethyl)thiazole was prepared according to the general procedure A1 using 5-(methoxymethyl)-4-(piperazin-1-yl)thiazole (0.10 g, 0.47 mmol), K$_2$CO$_3$ (0.097 g, 0.70 mmol), (2R)-2-(bromomethyl)-2,3-dihydro-1,4-benzodioxin (0.107 g, 0.47 mmol) and acetonitrile (1.25 ml). After the general procedure work-up, the evaporation residue was taken in mixture of EtOAc and water. Organic layer was separated and the water layer was extracted with EtOAc. Combined organic phases were washed with water and brine, dried and concentrated. The evaporation residue was purified by flash chromatography using 20-80% EtOAc in heptane as eluent to afford 0.080 g of (S)-4-(4-((2,3-dihydrobenzo[b][1,4]dioxin-2-yl)methyl)piperazin-1-yl)-5-(methoxymethyl)thiazole as semi-solid.
$^1$H NMR (400 MHz, CDCl$_3$) δ ppm 2.62-2.70 (3H, m), 2.71-2.79 (3H, m), 3.22-3.29 (4H, m), 3.39 (3H, s), 4.03 (1H, dd), 4.31-4.38 (2H, m), 4.55 (2H, s), 6.81-6.91 (4H, m), 8.55 (1H, s).

EXAMPLE 9: (S)-1-(3-(4-((2,3-Dihydrobenzo[b][1,4]dioxin-2-yl)methyl)piperazin-1-yl)-1,5-dimethyl-1H-pyrazol-4-yl)imidazolidin-2-one Step 1: tert-Butyl 4-(1,5-dimethyl-4-nitro-1H-pyrazol-3-yl)piperazine-1-carboxylate To a suspension of 1,5-dimethyl-3,4-dinitro-1H-pyrazole (0.30 g, 1.6 mmol) in isopropanol (12 ml) was added tert-butyl 1-piperazinecarboxylate (0.85 g, 4.8 mmol) and the mixture was heated in microwave reactor at 140° C. for 16 hours. Solvents were evaporated. Purification of evaporation residue by flash chromatography (20-50% EtOAc in heptane) afforded 0.29 g of tert-butyl 4-(1,5-dimethyl-4-nitro-1H-pyrazol-3-yl)piperazine-1-carboxylate as an yellow oil. LC-MS (ES+) [M+1]: 326.4.

Step 2: tert-Butyl 4-(4-amino-1,5-dimethyl-1H-pyrazol-3-yl)piperazine-1-carboxylate To a solution of tert-butyl 4-(1,5-dimethyl-4-nitro-1H-pyrazol-3-yl)piperazine-1-carboxylate (1.26 g, 3.87 mmol) in a mixture of THF (14 ml), MeOH (16 ml) and water (8 ml) was added NH$_4$Cl (2.07 g, 38.7 mmol) and the mixture was cooled with an ice bath. Zinc powder (2.53 g, 38.7 mmol)

was added and the mixture was stirred at room temperature. After 15 minutes the reaction mixture was diluted with EtOAc (50 ml) and filtered. Precipitate was washed with EtOAc and the filtrate was washed with brine, dried ($Na_2SO_4$) and concentrated. The evaporation residue was taken in dichloromethane, filtered and the solution was concentrated. Redissolution into dichloromethane-heptane and successive evaporation of solvents afforded 1.04 g tert-butyl 4-(4-amino-1,5-dimethyl-1H-pyrazol-3-yl)piperazine-1-carboxylate as grey solid. LC-MS (ES+) [M+1]: 296.6.

Step 3: tert-Butyl 4-(1,5-dimethyl-4-(2-oxoimidazolidin-1-yl)-1H-pyrazol-3-yl)piperazine-1-carboxylate To a solution of tert-butyl 4-(4-amino-1,5-dimethyl-1H-pyrazol-3-yl)piperazine-1-carboxylate (0.21 g, 0.71 mmol) in THF (7 ml) was added 2-chloroethyl isocyanate (0.073 ml, 0.85 mol). After 3 h potassium tert-butoxide (0.16 g, 1.42 mmol) was added and the resulting mixture was stirred at room temperature for 3.5 hours. Saturated solution of $NH_4Cl$ (5 ml) was added to the reaction mixture and THF was evaporated. The residue was partitioned between dichloromethane (10 ml) and water (10 ml) and the water layer was extracted with dichloromethane. Combined organic layers were washed with water, dried ($Na_2SO_4$) and concentrated to afford 0.25 g of tert-butyl 4-(1,5-dimethyl-4-(2-oxoimidazolidin-1-yl)-1H-pyrazol-3-yl)piperazine-1-carboxylate as an oil. LC-MS (ES+) [M+1]: 365.3.

Step 4: 1-(1,5-Dimethyl-3-(piperazin-1-yl)-1H-pyrazol-4-yl)imidazolidin-2-one tert-Butyl 4-(1,5-dimethyl-4-(2-oxoimidazolidin-1-yl)-1H-pyrazol-3-yl)piperazine-1-carboxylate (0.24 g, 0.67 mmol) was mixed with trifluoroacetic acid (3.5 ml) and the resulting solution was stirred at room temperature for 3 hours. Evaporation of trifluoroacetic acid afforded 0.44 g of the bis-trifluoroacetic acid salt of 1-(1,5-dimethyl-3-(piperazin-1-yl)-1H-pyrazol-4-yl)imidazolidin-2-one as an oil. LC-MS (ES+) [M+1]: 265.5.

Step 5: (S)-1-(3-(4-((2,3-dihydrobenzo[b][1,4]dioxin-2-yl)methyl)piperazin-1-yl)-1,5-dimethyl-1H-pyrazol-4-yl)imidazolidin-2-one (S)-1-(3-(4-((2,3-dihydrobenzo[b][1,4]dioxin-2-yl)methyl)piperazin-1-yl)-1,5-dimethyl-1H-pyrazol-4-yl)imidazolidin-2-one was prepared according to the general procedure A1 using bis-trifluoroacetic acid salt of 1-(1,5-dimethyl-3-(piperazin-1-yl)-1H-pyrazol-4-yl)imidazolidin-2-one 0.10 g, 0.20 mmol), di-isopropylethylamine (0.035 ml, 0.20 mmol), $K_2CO_3$ (0.056 g, 0.41 mmol), (2R)-2-(bromomethyl)-2,3-dihydro-1,4-benzodioxin (0.047 g, 0.20 mmol) and acetonitrile (1 ml). The product was purified by flash chromatography (0-10% MeOH in dichloromethane) to afford 0.060 g of (S)-1-(3-(4-((2,3-dihydrobenzo[b][1,4]dioxin-2-yl)methyl)piperazin-1-yl)-1,5-dimethyl-1H-pyrazol-4-yl)imidazolidin-2-one as a yellowish solid.

$^1$H NMR (400 MHz, DMSO-$d_6$) δ ppm 1.99 (3H, s), 2.53-2.64 (5H, m), 3.96-3.06 (4H, m), 3.34-3.39 (2H, m), 3.48-3.56 (2H, m), 3.54 (3H, obs.s), 3.96 (1H, dd), 4.27-4.32 (1H, m), 4.36 (1H, br s), 6.44 (1H, s), 6.78-6.89 (4H, m).

EXAMPLE 10: (S)-1-((2,3-Dihydrobenzo[b][1,4]dioxin-2-yl)methyl)-4-(1-(pyridin-2-yl)-1H-pyrazol-5-yl)piperazine Step 1: 1-(4-Benzylpiperazin-1-yl)-3,3-diethoxypropan-1-one To a suspension of sodium 3,3-diethoxypropanoate (6.41 g, 34.8 mmol, prepared as described in EP1426366 A1) in dimethylformamide (70 ml) was added 1-(3-dimethylaminopropyl)-3-ethylcarbodiimide hydrochloride (8.0 g, 41.8 mmol), 1-hydroxybenzoltriazole (6.35 g, 47.0 mmol) and 1-benzylpiperazine (4.0 ml, 34.8 mmol). After 3 days DMF was evaporated in vacuo and water was (50 ml) was added to the residue. Mixture was extracted with EtOAc. The combined organic layers were washed with saturated $NaHCO_3$ and brine, dried ($Na_2SO_4$) and concentrated. Purification of the orange oily evaporation residue by flash chromatography (10-100% EtOAc-heptane) afforded 4.71 g of 1-(4-benzylpiperazin-1-yl)-3,3-diethoxypropan-1-one as yellow oil. LC-MS (ES+) [M+1]: 321.6.

Step 2: 1-Benzyl-4-(1-(pyridin-2-yl)-1H-pyrazol-5-yl)piperazine

To a solution of 1-(4-benzylpiperazin-1-yl)-3,3-diethoxypropan-1-one (4.7 g, 14.7 mmol) in chloroform (40 ml) at 0° C. was added a mixture of trifluoroacetic acid (14 ml) and water (14 ml) and the mixture was stirred vigorously. After 24 hours chloroform (40 ml) was added and pH of the solution was adjusted to 6-7 by adding 5M NaOH. Phases were separated and water phase was extracted with dichloromethane (50 ml). Combined organic phases were dried ($Na_2SO_4$) and concentrated to dryness—The resulting yellow oily evaporation residue was dissolved in EtOH (70 ml) and to the solution were added methanesulfonic acid (0.095 ml, 1.47 mmol) and 2-hydrazinopyridine (1.60 g, 14.7 mmol). After 17 hours pyridine (1.4 ml) was added and the mixture was evaporated to dryness. The evaporation residue was taken into pyridine (70 ml) and phosphorus oxychloride (2.70 ml, 29.0 mmol) was added. After 19 hours the reaction mixture was concentrated to dryness. To the resulting brown glue was added EtOAc (60 ml) and water (25 ml) and after stirring for a while the phases were separated. The water layer was made clearly basic by addition of 5M NaOH and solution was extracted with EtOAc. Organic phases were combined, washed with brine, dried ($Na_2SO_4$) and solvents were evaporated. Purification of the evaporation residue by flash chromatography (MeOH-dichloromethane) afforded 0.23 g of 1-benzyl-4-(1-(pyridin-2-yl)-1H-pyrazol-5-yl)piperazine as brown oil. LC-MS (ES+) [M+1]: 320.2.

Step 3: 1-(1-(Pyridin-2-yl)-1H-pyrazol-5-yl)piperazine

A solution of 1-benzyl-4-(1-(pyridin-2-yl)-1H-pyrazol-5-yl)piperazine (0.23 g, 0.72 mmol) in acetic acid (14 ml) was hydrogenated in flow reactor (ThalesNano H-Cube, Pd/C-column, flow rate 1 ml/min, 80° C., 80 bar $H_2$-pressure) repeating the run twice with fresh Pd/C-column. Solvents were evaporated and the resulting yellow oil was taken into mixture of $NaHCO_3$ and dichloromethane. Phases were separated and the aqueous phase was extracted first with dichloromethane and then with 20% isopropanol-EtOAc-mixture. The combined organic phases were dried ($Na_2SO_4$) and concentrated. Purification of the evaporation residue by flash chromatography (1-15% MeOH in dichloromethane+

2% triethylamine) afforded 0.049 g of 1-(1-(pyridin-2-yl)-1H-pyrazol-5-yl)piperazine as brown oil. LC-MS (ES+) [M+1]: 230.1.

Step 4: (S)-1-((2,3-dihydrobenzo[b][1,4]dioxin-2-yl)methyl)-4-(1-(pyridin-2-yl)-1H-pyrazol-5-yl)piperazine (S)-1-((2,3-Dihydrobenzo[b][1,4]dioxin-2-yl)methyl)-4-(1-(pyridin-2-yl)-1H-pyrazol-5-yl)piperazine was prepared according to the general procedure A1 using 1-(1-(pyridin-2-yl)-1H-pyrazol-5-yl)piperazine (0.047 g, 0.21 mmol), diisopropylethylamine (0.036 ml, 0.21 mmol), $K_2CO_3$ (0.028 g, 0.21 mmol), (2R)-2-(bromomethyl)-2,3-dihydro-1,4-benzodioxin (0.047 g, 0.21 mmol) and acetonitrile (0.9 ml). The product was purified by flash chromatography (0-10% MeOH in dichloromethane+2% triethylamine) to afford 0.006 g of (S)-1-((2,3-dihydrobenzo[b][1,4]dioxin-2-yl)methyl)-4-(1-(pyridin-2-yl)-1H-pyrazol-5-yl)piperazine as a yellow oil $^1$H NMR (400 MHz, CDCl$_3$) δ ppm 2.60-2.67 (3H, m), 2.67-2.77 (3H, m), 2.95-2.96-3.06 (4H, m), 4.00 (1H, dd), 4.27-4.34 (2H, m), 5.88 (1H, d), 6.80-6.90 (4H, m), 7.20-7.24 (1H, m), 7.57 (1H, d), 7.77-7.87 (2H, m), 8.55 (1H, ddd).

EXAMPLE 11: (S)-1-((2,3-Dihydrobenzo[b][1,4]dioxin-2-yl)methyl)-4-(4-(methoxymethyl)-1,5-dimethyl-1H-pyrazol-3-yl)piperazine Step 1: 4-Benzylpiperazine-1-carbothioyl hydrochloride To a solution of thiophosgene (4.4 ml, 57 mmol) in THF (40 ml) at 0° C. was added a solution of 1-benzylpiperazine (9.7 ml, 57 mmol) in THF (35 ml) over 35 minutes, keeping the reaction temperature below 5° C. during addition. The reaction mixture was stirred at 0° C. After 1.5 hours the reaction mixture was filtered and the precipitate was washed with cold diethyl ether (2×10 ml). Drying the precipitate afforded 17 g of crude 4-benzylpiperazine-1-carbothioyl hydrochloride as yellowish solid.

Step 2: Ethyl 5-(4-benzylpiperazin-1-yl)-3-methyl-1H-pyrazole-4-carboxylate

To a solution of crude 4-benzylpiperazine-1-carbothioyl hydrochloride (2.0 g, 6.9 mmol) in ethanol (8 ml) was added triethylamine (0.96 ml, 6.9 mmol) and solution was cooled to 0° C. Hydrazine monohydrate (0.67 ml, 13.7 mmol) was added in a manner that kept the reaction temperature below 4° C. The reaction mixture was let to warm up spontaneously on an ice bath. After 24 hours HCl-ethanol solution, prepared by addition of thionyl chloride (2.5 ml, 34.3 mmol) to ethanol (10 ml) at 0° C., was added to the reaction mixture while cooling the reaction vessel with an ice bath. After 10 minutes ethyl-2-chloroacetoacetate (1.9 ml, 13.7 mmol) was added and the reaction mixture was stirred at room temperature for 3 days. Solvents were evaporated and 1M HCl (20 ml) was added along with some water to dissolve other material than elemental sulphur. The sulphuric precipitate was washed with water and combined water layers were washed with EtOAc (70 ml). The pH of the water phase was adjusted to 10 using saturated NaHCO$_3$ and 5M NaOH solution. The basic water solution was extracted with EtOAc (3×). Combined organic phases were washed with brine and solvents were evaporated. The oily evaporation residue was dissolved in dichloromethane-heptane mixture. Evaporation of the solvents afforded 1.75 g of crude ethyl 5-(4-benzylpiperazin-1-yl)-3-methyl-1H-pyrazole-4-carboxylate as a brown solid. LC-MS (ES+) [M+1]: 330.3.

Step 3: Ethyl 3-(4-benzylpiperazin-1-yl)-1,5-dimethyl-1H-pyrazole-4-carboxylate

To a solution of ethyl 5-(4-benzylpiperazin-1-yl)-3-methyl-1H-pyrazole-4-carboxylate (1.3 g, 4.0 mmol) in DMF (13 ml) at 0° C. was added sodium hydride (0.22 g, 5.54 mmol, 60 m-% dispersion in mineral oil). After 20 minutes, iodomethane (0.30 ml, 4.8 mmol) was added and the cooling bath was removed. After 4 hours water (40 ml) was added and the mixture was extracted with EtOAc (3×30 ml). Combined organic phases were washed with brine, dried (Na$_2$SO$_4$) and concentrated to dryness. Purification of the oily evaporation residue by flash chromatography (MeOH-dichloromethane) afforded 0.4 g of ethyl 3-(4-benzylpiperazin-1-yl)-1,5-dimethyl-1H-pyrazole-4-carboxylate as yellowish solid. LC-MS (ES+) [M+1]: 343.8.

Step 4: (3-(4-Benzylpiperazin-1-yl)-1,5-dimethyl-1H-pyrazol-4-yl)methanol

To a solution of ethyl 3-(4-benzylpiperazin-1-yl)-1,5-dimethyl-1H-pyrazole-4-carboxylate (0.4 g, 1.17 mmol) in THF (4 ml) at 0° C. was added lithium aluminum hydride (0.044 g, 1.17 mmol) and the reaction mixture was stirred at 0° C. After 2 hours the mixture was brought to room temperature and after further 5 hours lithium aluminum hydride (0.022 g, 0.59 mmol) was added. Mixture was stirred at room temperature overnight. To the reaction mixture was added water (70 μl), 15% NaOH (70 μl) and water (0.2 ml). After 1 h precipitate was filtered and washed with EtOAc. The filtrate was washed with water and brine and dried (Na$_2$SO$_4$). Evaporation of the solvents afforded 0.26 g of (3-(4-benzylpiperazin-1-yl)-1,5-dimethyl-1H-pyrazol-4-yl)methanol as off white solid which was used without further purification. LC-MS (ES+) [M+1]: 301.3.

Step 5: 1-Benzyl-4-(4-(methoxymethyl)-1,5-dimethyl-1H-pyrazol-3-yl)piperazine

To a solution of (3-(4-benzylpiperazin-1-yl)-1,5-dimethyl-1H-pyrazol-4-yl)methanol (0.26 g, 0.87 mmol) in DMF (3 ml) at 0° C. was added sodium hydride (0.045 g, 1.13 mmol, 60 m-% dispersion in mineral oil). After 20 minutes, iodomethane (0.054 ml, 0.87 mmol) was added. The cooling bath was removed after 1.5 hours. After 6 hours sodium hydride (0.030 g, 0.75 mmol) and iodomethane (0.010 ml, 0.16 mmol) were added and the reaction mixture was stirred at room temperature overnight. Saturated solution of NH$_4$Cl was added and mixture was extracted with EtOAc. Combined organic phases were washed with brine and dried (Na$_2$SO$_4$). Evaporation of the solvents afforded 0.22 g of oil containing a mixture of starting material and methylated product.

To the crude product in DMF (2.4 ml) at 0° C. was added sodium hydride (0.029 g, 0.73 mmol). After 10 minutes, iodomethane (0.046 ml, 0.73 mmol) was added and the mixture was stirred at 0° C. for 1 h and then at room temperature for 2 hours. Water was added and the precipitate was filtered, washed (water) and dried in vacuum oven (30° C.) Yield 0.088 g of 1-benzyl-4-(4-(methoxymethyl)-1,5-dimethyl-1H-pyrazol-3-yl)piperazine as white solid. LC-MS (ES+) [M+1]: 315.2.

Step 6: 1-(4-(Methoxymethyl)-1,5-dimethyl-1H-pyrazol-3-yl)piperazine

To a solution of 1-benzyl-4-(4-(methoxymethyl)-1,5-dimethyl-1H-pyrazol-3-yl)piperazine (0.087 g, 0.28 mmol) and formic acid (0.021 ml, 0.55 mmol) in methanol (1.4 ml) was added ammonium formate (0.174 g, 2.77 mmol) and 10% Pd/C (0.059 g, 0.055 mmol). The mixture was heated in reflux. After 2.5 hours the reaction mixture was cooled and filtered through a pad of celite. The filter cake was washed with a mixture of MeOH and formic acid. Filtrate was concentrated to dryness and the evaporation residue was taken into a mixture of dichloromethane and sat. NaHCO$_3$. Phases were separated and aqueous phase was extracted with dichloromethane. Combined organic phases were washed with brine and dried (Na$_2$SO$_4$). Evaporation of the solvents afforded 0.018 g of 1-(4-(methoxymethyl)-1,5-dimethyl-1H-pyrazol-3-yl)piperazine as cloudy oil that was used as such in the next step.

LC-MS (ES+) [M+1]: 224.9.

Step 7: (S)-1-((2,3-Dihydrobenzo[b][1,4]dioxin-2-yl)methyl)-4-(4-(methoxymethyl)-1,5-dimethyl-1H-pyrazol-3-yl)piperazine (S)-1-((2,3-Dihydrobenzo[b][1,4]dioxin-2-yl)methyl)-4-(4-(methoxymethyl)-1,5-dimethyl-1H-pyrazol-3-yl)piperazine was prepared according to the general procedure A1 using 1-(4-(methoxymethyl)-1,5-dimethyl-1H-pyrazol-3-yl)piperazine (0.017 g, 0.076 mmol), di-isopropylethylamine (0.016 ml, 0.091 mmol), K$_2$CO$_3$ (0.016 g, 0.114 mmol), (2R)-2-(bromomethyl)-2,3-dihydro-1,4-benzodioxin (0.017 g, 0.076 mmol) and acetonitrile (0.4 ml). The product was purified by reverse phase flash chromatography (0.1% NH$_4$OH-acetonitrile) to afford 0.0047 g of (S)-1-((2,3-dihydrobenzo[b][1,4]dioxin-2-yl)methyl)-4-(4-(methoxymethyl)-1,5-dimethyl-1H-pyrazol-3-yl)piperazine as brown oil.

$^1$H NMR (400 MHz, CDCl$_3$) δ ppm 2.19 (3H, s), 2.60-2.68 (3H, m), 2.68-2.79 (3H, m), 3.14-3.25 (4H, m), 3.32 (3H, s), 3.64 (3H, s), 4.01 (1H, dd), 4.19 (2H, s), 4.29-4.38 (2H, m), 6.79-6.92 (4H, m).

EXAMPLE 12: (S)-Ethyl 3-(4-((2,3-dihydrobenzo[b][1,4]dioxin-2-yl)methyl)piperazin-1-yl)-1,5-dimethyl-1H-pyrazole-4-carboxylate

Step 1: Ethyl 1,5-dimethyl-3-(piperazin-1-yl)-1H-pyrazole-4-carboxylate

To a solution of ethyl 3-(4-benzylpiperazin-1-yl)-1,5-dimethyl-1H-pyrazole-4-carboxylate (0.40 g, 1.17 mmol) (obtained as described in Example 11 Step 1-2) and formic acid (0.088 ml, 2.33 mmol) in MeOH (6 ml) was added ammonium formate (0.74 g, 11.7 mmol) and 10% Pd/C (0.250 g, 0.23 mmol). The reaction mixture was stirred at 45° C. After 2.5 hours the reaction mixture was cooled and filtered through a pad of celite. The filter cake was washed with a mixture of MeOH and formic acid. Filtrate was concentrated to dryness and the evaporation residue was taken into mixture of dichloromethane and sat. NaHCO$_3$. Phases were separated and aqueous phase was extracted with dichloromethane and EtOAc. Combined organic phases were washed with brine and dried (Na$_2$SO$_4$). Evaporation of the solvents afforded 0.22 g of ethyl 1,5-dimethyl-3-(piper-azin-1-yl)-1H-pyrazole-4-carboxylate as brown solidifying oil that was used as such in the next step. LC-MS (ES+) [M+1]: 253.1.

Step 2: (S)-Ethyl 3-(4-((2,3-dihydrobenzo[b][1,4]dioxin-2-yl)methyl)piperazin-1-yl)-1,5-dimethyl-1H-pyrazole-4-carboxylate (S)-Ethyl 3-(4-((2,3-dihydrobenzo[b][1,4]dioxin-2-yl)methyl)piperazin-1-yl)-1,5-dimethyl-1H-pyrazole-4-carboxylate was prepared according to the general procedure A1 using ethyl 1,5-dimethyl-3-(piperazin-1-yl)-1H-pyrazole-4-carboxylate (0.22 g, 0.87 mmol), di-isopropylethylamine (0.18 ml, 1.05 mmol), K$_2$CO$_3$ (0.180 g, 1.31 mmol), (2R)-2-(bromomethyl)-2,3-dihydro-1,4-benzodioxin (0.20 g, 0.87 mmol) and acetonitrile (2.9 ml). The product was purified by reverse phase flash chromatography (0.1% HCOOH-acetonitrile) to afford 0.11 g of (S)-ethyl 3-(4-((2,3-dihydrobenzo[b][1,4]dioxin-2-yl)methyl)piperazin-1-yl)-1,5-dimethyl-1H-pyrazole-4-carboxylate as yellowish oil.

$^1$H NMR (400 MHz, CDCl$_3$) δ ppm 1.35 (3H, t), 2.46 (3H, s), 2.59-2.81 (6H, m), 3.20-3.30 (4H, m), 3.67 (3H, s), 4.01 (1H, dd), 4.28 (2H, q), 4.31-4.37 (2H, m), 6.79-6.91 (4H, m).

EXAMPLE 13: (S)-2-(3-(4-((2,3-Dihydrobenzo[b][1,4]dioxin-2-yl)methyl)piperazin-1-yl)-1,5-dimethyl-1H-pyrazol-4-yl)propan-2-ol To a solution of (S)-ethyl 3-(4-((2,3-dihydrobenzo[b][1,4]dioxin-2-yl)methyl)piperazin-1-yl)-1,5-dimethyl-1H-pyrazole-4-carboxylate (0.1 g, 0.25 mmol) (obtained as in Example 12) in THF (1 ml) was added a solution containing methylmagnesium bromide (0.83 ml, 2.50 mmol, 3M solution in diethyl ether) in THF (1.5 ml). After 3.5 hours methylmagnesium bromide (0.83 ml, 2.50 mmol, 3M solution in diethyl ether) was added. Reaction mixture was stirred at room temperature overnight. A mixture of sat. NH$_4$Cl (10 ml) and ice was added and phases were separated. Aqueous phase was extracted with EtOAc. Combined organic phases were washed with brine, dried (Na$_2$SO$_4$) and evaporated. Purification of the evaporation residue by reverse phase column chromatography (0.1% NH$_4$OH—acetonitrile) afforded 0.093 g of (S)-2-(3-(4-((2,3-dihydrobenzo[b][1,4]dioxin-2-yl)methyl)piperazin-1-yl)-1,5-dimethyl-1H-pyrazol-4-yl)propan-2-ol as a white solid.

$^1$H NMR (400 MHz, CDCl$_3$) δ ppm 1.48 (6H, s), 2.23 (3H, s), 2.59-2.68 (3H, m), 2.68-2.77 (3H, m), 3.03-3.15 (4H, m), 3.69 (3H, s), 4.02 (1H, dd), 4.26-4.36 (2H, m), 6.80-6.89 (4H, m), 7.78 (1H, br s)

EXAMPLE 14: (S)-1-(3-(4-((2,3-Dihydrobenzo[b][1,4]dioxin-2-yl)methyl)piperazin-1-yl)-1,5-dimethyl-1H-pyrazol-4-yl)pyrrolidin-2-one

Step 1: tert-Butyl 4-(1,5-dimethyl-4-(2-oxopyrrolidin-1-yl)-1H-pyrazol-3-yl)piperazine-1-carboxylate To a solution of tert-butyl 4-(4-amino-1,5-dimethyl-1H-pyrazol-3-yl)piperazine-1-carboxylate (0.2 g, 0.68 mmol) (obtained as in Example 9 step 1-2) and triethylamine (0.11 ml, 0.81 mmol) in dichloromethane (2.5 ml) at 0° C. was added 4-chlorobutyryl chloride (0.083 ml, 0.75 mmol) dropwise. Mixture was stirred at room temperature. After 30 minutes dichloromethane (15 ml) was added and the mixture was washed with sat. NaHCO$_3$. Aqueous phase was back extracted with dichloromethane. Combined organic phases were dried (Na$_2$SO$_4$) and solvents were evaporated. The residual reddish foam was dissolved in THF (7 ml) and sodium hydride (0.035 g, 0.88 mmol, 60 m-% dispersion in mineral oil) was added. The mixture was stirred at room temperature overnight. To the reaction mixture was added sat. NH$_4$Cl (10 ml) and phases were separated. Aqueous phase was extracted with EtOAc. Combined organic phases were washed with brine and dried (Na$_2$SO$_4$). Evaporation of solvents afforded 0.25 g of tert-butyl 4-(1,5-dimethyl-4-(2-oxopyrrolidin-1-yl)-1H-pyrazol-3-yl)piperazine-1-carboxylate as oil that was used as such in the next step. LC-MS (ES+) [M+1]: 364.4.

Step 2: 1-(1,5-Dimethyl-3-(piperazin-1-yl)-1H-pyrazol-4-yl)pyrrolidin-2-one tert-Butyl 4-(1,5-dimethyl-4-(2-oxopyrrolidin-1-yl)-1H-pyrazol-3-yl)piperazine-1-carboxylate (0.25 g, 0.68 mmol) was mixed with trifluoroacetic acid (4 ml) and the resulting solution was stirred at room temperature for 1 hour. Trifluoroacetic acid was evaporated. The evaporation residue was made basic by addition of ammonia solution. The aqueous phase was extracted with dichloromethane and separately with 10-20% isopropanol-EtOAc-mixture. All the organic phases were combined and dried (Na$_2$SO$_4$). Evaporation of the solvents afforded 0.15 g of 1-(1,5-dimethyl-3-(piperazin-1-yl)-1H-pyrazol-4-yl)pyrrolidin-2-one as red solid. LC-MS (ES+) [M+1]: 264.6.

Step 3: (S)-1-(3-(4-((2,3-Dihydrobenzo[b][1,4]dioxin-2-yl)methyl)piperazin-1-yl)-1,5-dimethyl-1H-pyrazol-4-yl)pyrrolidin-2-one (S)-1-(3-(4-((2,3-Dihydrobenzo[b][1,4]dioxin-2-yl)methyl)piperazin-1-yl)-1,5-dimethyl-1H-pyrazol-4-yl)pyrrolidin-2-one was prepared according to the general procedure A1 using 1-(1,5-dimethyl-3-(piperazin-1-yl)-1H-pyrazol-4-yl)pyrrolidin-2-one (0.14 g, 0.54 mmol), di-isopropylethylamine (0.095 ml, 0.55 mmol), K$_2$CO$_3$ (0.15 g, 1.09 mmol), (2R)-2-(bromomethyl)-2,3-dihydro-1,4-benzodioxin (0.125 g, 0.55 mmol) and acetonitrile (1.4 ml). After evaporation of the solvents inorganic material was removed by dissolution to dichloromethane and washing with sat. NaHCO$_3$. The evaporation residue was purified by reverse phase flash chromatography (0.1% NH$_4$OH-acetonitrile) to afford 0.15 g of (S)-1-(3-(4-((2,3-Dihydrobenzo[b][1,4]dioxin-2-yl)methyl)piperazin-1-yl)-1,5-dimethyl-1H-pyrazol-4-yl)pyrrolidin-2-one as white solid.
$^1$H NMR (400 MHz, CDCl$_3$) δ ppm 2.07 (3H, s), 2.10-2.21 (2H, m), 2.51 (2H, t), 2.57-2.66 (3H, m), 2.66-2.76 (3H, m), 3.04-3.18 (4H, m), 3.60-3.68 (5H, m), 4.00 (1H, dd), 4.28-4.38 (2H, m), 6.80-6.90 (4H, m).

EXAMPLE 15: (S)-1-(3-(4-((2,3-Dihydrobenzo[b][1,4]dioxin-2-yl)methyl)piperazin-1-yl)-1,5-dimethyl-1H-pyrazol-4-yl)-3-methylimidazolidin-2-one To a solution of (S)-1-(3-(4-((2,3-dihydrobenzo[b][1,4]dioxin-2-yl)methyl)piperazin-1-yl)-1,5-dimethyl-1H-pyrazol-4-yl)imidazolidin-2-one (0.1 g, 0.24 mmol) (obtained as reported in Example 9 steps 1-5) in DMF (1 ml) at 0° C. was added sodium hydride (0.015 g, 0.36 mmol, 60 m-% dispersion in mineral oil). After 1 h iodomethane (0.030 ml, 0.49 mmol) was added. After 1.5 h sat. NH$_4$Cl (4 ml) and water (1 ml) were added and the resulting mixture was extracted with EtOAc. Combined organic phases were washed with brine and dried (Na$_2$SO$_4$) and solvents were evaporated. Purification of the evaporation residue by reverse phase column chromatography (NH$_4$OH—acetonitrile) afforded 0.032 g of (S)-1-(3-(4-((2,3-dihydrobenzo[b][1,4]dioxin-2-yl)methyl)piperazin-1-yl)-1,5-dimethyl-1H-pyrazol-4-yl)-3-methylimidazolidin-2-one as white powder.
$^1$H NMR (400 MHz, CDCl$_3$) δ ppm 2.09 (3H, s), 2.55-2.65 (3H, m), 2.65-2.75 (3H, m), 2.86 (3H, s), 3.09-3.20 (4H, m), 3.38-3.46 (2H, m), 3.55-3.64 (5H, m), 4.00 (1H, dd), 4.27-4.37 (2H, m), 6.79-6.91 (4H, m)

EXAMPLE 16: (S)—N-(4-(4-((2,3-Dihydrobenzo[b][1,4]dioxin-2-yl)methyl)piperazin-1-yl)-1,2,5-thiadiazol-3-yl)acetamide

Step 1: tert-Butyl 4-(4-chloro-1,2,5-thiadiazol-3-yl)piperazine-1-carboxylate To a solution of tert-butyl piperazine-1-carboxylate (4.8 g, 25.8 mmol) and di-isopropylamine (4.5 ml, 25.8 mmol) in DMF (20 mL) was added 3,4-dichloro-1,2,5-thiadiazole (2.0 g, 12.9 mmol) at room temperature. The resulting reaction mixture was heated to 100° C. for 16 h. The reaction mixture was quenched with water (100 ml) and extracted with EtOAc (3×20 ml). The combined organic layers were washed with water and brine, dried (Na$_2$SO$_4$) and concentrated. Purification of the evaporation residue by flash chromatography (EtOAc and petroleum ether) afforded 2.7 g of tert-butyl 4-(4-chloro-1,2,5-thiadiazol-3-yl)piperazine-1-carboxylate as white solid.

Step 2: tert-Butyl 4-(4-amino-1,2,5-thiadiazol-3-yl)piperazine-1-carboxylate To a stirred solution of tert-butyl 4-(4-chloro-1,2,5-thiadiazol-3-yl)piperazine-1-carboxylate (4.0 g, 13.15 mmol) in dry THF (24 ml) was added LiHMDS (1 M in THF) (13.8 ml, 13.807 mmol) at 0° C. The reaction mixture stirred at room temperature for 2 h. The reaction mixture was quenched with NH$_4$Cl solution (20 ml) and extracted with EtOAc (3×30 ml). The combined organic layers were washed with water, brine, dried (Na$_2$SO$_4$), filtered and concentrated under reduced pressure. The evaporation residue was dissolved in MeOH and NEt$_3$ and heated to reflux for 16 h. The reaction mixture was concentrated under reduced pressure. Purification of the evaporation residue by flash chromatography (EtOAc/petroleum ether) afforded 1.5 g of tert-butyl 4-(4-amino-1,2,5-thiadiazol-3-yl)piperazine-1-carboxylate as pale yellow solid.

Step 3: tert-Butyl 4-(4-acetamido-1,2,5-thiadiazol-3-yl)piperazine-1-carboxylate To a stirred solution of tert-butyl 4-(4-amino-1,2,5-thiadiazol-3-yl)piperazine-1-carboxylate (1.2 g, 4.22 mmol) in pyridine were added DMAP (103 mg, 0.85 mmol) and Ac$_2$O (0.62 ml, 6.33 mmol) at room temperature. The reaction mixture was heated to 80° C. for 16 h. The reaction mixture was concentrated under reduced pressure and the evaporation residue was dissolved in EtOAc. The solution was washed with water and brine, dried (Na$_2$SO$_4$) and concentrated. Purification of the evaporation residue by flash chromatography (EtOAc/Petroleum ether) afforded 0.58 g of tert-butyl 4-(4-acetamido-1,2,5-thiadiazol-3-yl)piperazine-1-carboxylate as pale yellow solid.

Step 4: Trifluoroacetic acid salt of N-(4-(piperazin-1-yl)-1,2,5-thiadiazol-3-yl)acetamide To an ice-cold solution of tert-butyl 4-(4-acetamido-1,2,5-thiadiazol-3-yl)piperazine-1-carboxylate (420 mg, 1.284 mmol) in CH₂Cl₂ was added TFA (0.4 ml, 5.136 mmol) and the mixture was stirred at room temperature for 6 h. The reaction mixture was concentrated under reduced pressure. Trituration of the evaporation residue with n-pentane afforded 0.51 g of trifluoroacetic acid salt of N-(4-(piperazin-1-yl)-1,2,5-thiadiazol-3-yl)acetamide as pale yellow solid m/z 228.1 [(M-TFA)+H]⁺

Step 5: (S)—N-(4-(4-((2,3-dihydrobenzo[b][1,4]dioxin-2-yl)methyl)piperazin-1-yl)-1,2,5-thiadiazol-3-yl)acetamide (S)—N-(4-(4-((2,3-dihydrobenzo[b][1,4]dioxin-2-yl)methyl)piperazin-1-yl)-1,2,5-thiadiazol-3-yl)acetamide was prepared according to the general procedure A2 using trifluoroacetic acid salt of N-(4-(piperazin-1-yl)-1,2,5-thiadiazol-3-yl)acetamide (0.10 g, 0.29 mmol), Na₂CO₃ (0.078 g, 0.73 mmol), (2R)-2-(bromomethyl)-2,3-dihydro-1,4-benzodioxin (0.074 g, 0.32 mmol) and DMF (1.5 ml). The evaporation residue was purified by reverse phase column chromatography (0.1% NH₄OH-acetonitrile) to afford 0.037 g of (S)—N-(4-(4-((2,3-dihydrobenzo[b][1,4]dioxin-2-yl)methyl)piperazin-1-yl)-1,2,5-thiadiazol-3-yl)acetamide as white solid.

¹H NMR (400 MHz, CDCl₃) δ ppm 2.43 (3H, br s), 2.64-2.83 (6H, m), 3.20-3.30 (4H, m), 4.00-4.07 (1H, m), 4.28-4.38 (2H, m), 6.80-6.93 (4H, m), 7.51 (1H, br s)

EXAMPLE 17: (S)-1-(4-(4-((2,3-Dihydrobenzo[b][1,4]dioxin-2-yl)methyl)piperazin-1-yl)-1,2,5-thiadiazol-3-yl)-3,3-dimethylpyrrolidin-2-one Step 1: tert-Butyl 2-oxopyrrolidine-1-carboxylate To a solution of pyrrolidone (20.0 g, 235.0 mmol) in CH₃CN (200 mL) were added (Boc)₂O (54.4 mL, 244.4 mmol) and DMAP (2.86 g, 23.5 mmol) at 0° C. The reaction mixture was stirred at room temperature for 16 h. The reaction mixture was concentrated under reduced pressure. Purification of the evaporation residue by flash chromatography (EtOAc/petroleum ether) afforded 25 g of tert-butyl 2-oxopyrrolidine-1-carboxylate as yellow oil.

Step 2: tert-Butyl 3,3-dimethyl-2-oxopyrrolidine-1-carboxylate

To a stirred solution of tert-butyl 2-oxopyrrolidine-1-carboxylate (2.0 g, 10.8 mmol) in dry THF (24.0 mL) was added LiHMDS (1 M in THF) (13.8 mL, 32.4 mmol) at −78° C. The reaction mixture was stirred at −78° C. for 1 h followed by addition of MeI (4.0 mL, 64.8 mmol) in dry THF at −78° C. The reaction mixture was stirred at −78° C. for 1 h and then stirred at room temperature for 16 h. The reaction mixture was quenched with NH₄Cl solution (20.0 mL) and extracted with EtOAc (3×30 mL). The combined organic layers were washed with water (2×20 mL), brine, dried (Na₂SO₄) and concentrated under reduced pressure. Purification of the evaporation residue by flash chromatography (EtOAc/Petroleum ether) afforded 1.0 g of tert-butyl 3,3-dimethyl-2-oxopyrrolidine-1-carboxylate as off white sticky solid.

Step 3: 3,3-dimethylpyrrolidin-2-one

To an ice cold stirred solution of tert-butyl 3,3-dimethyl-2-oxopyrrolidine-1-carboxylate (2.0 g, 9.378 mmol) in dioxane (25.0 mL) was added solution of HCl in dioxane (25.0 mL) and the mixture was stirred at room temperature for 2 h. The reaction mixture was concentrated under reduced pressure. Trituration of the evaporation residue with n-pentane afforded 2.0 g of 3,3-dimethylpyrrolidin-2-one as brown gummy solid. Used as such without further purification.

Step 4: tert-Butyl 4-(4-(3,3-dimethyl-2-oxopyrrolidin-1-yl)-1,2,5-thiadiazol-3-yl)piperazine-1-carboxylate To a solution of 3,3-dimethylpyrrolidin-2-one (1.96 g, 17.3 mmol) in dioxane was added K₃PO₄ (8.37 g, 39.5 mmol) and stirred for 30 min. Then tert-butyl 4-(4-chloro-1,2,5-thiadiazol-3-yl)piperazine-1-carboxylate (4.0 g, 13.2 mmol) (prepared as in step 1 of Example 16) CuI (2.5 g, 13.2 mmol) and N¹,N²-Dimethylethylene-1,2-diamine (0.4 mL, 3.9 mmol) were added to the reaction mixture at room temperature. The reaction mixture was heated in sealed tube at 100° C. for 16 h. The reaction mixture was filtered through a celite pad, washed with EtOAc (40.0 mL) and the filtrate was concentrated under reduced pressure. Purification of the evaporation residue by flash chromatography (EtOAc in petroleum ether) afforded 0.15 g of tert-butyl 4-(4-(3,3-dimethyl-2-oxopyrrolidin-1-yl)-1,2,5-thiadiazol-3-yl)piperazine-1-carboxylate as off white solid.

Step 5: 3,3-Dimethyl-1-(4-(piperazin-1-yl)-1,2,5-thiadiazol-3-yl)pyrrolidin-2-one hydrochloride A solution of tert-butyl 4-(4-(3,3-dimethyl-2-oxopyrrolidin-1-yl)-1,2,5-thiadiazol-3-yl)piperazine-1-carboxylate (150 mg, 0.393 mmol) in HCl-dioxane (25.0 mL) was stirred at 0° C.→RT for 3 h. The reaction mixture was concentrated under reduced pressure. Trituration of the evaporation residue with n-pentane afforded 0.12 g of 3,3-dimethyl-1-(4-(piperazin-1-yl)-1,2,5-thiadiazol-3-yl)pyrrolidin-2-one hydrochloride as off white solid m/z [M+1]: 282.2

Step 6: (S)-1-(4-(4-((2,3-dihydrobenzo[b][1,4]dioxin-2-yl)methyl)piperazin-1-yl)-1,2,5-thiadiazol-3-yl)-3,3-dimethylpyrrolidin-2-one (S)-1-(4-(4-((2,3-Dihydrobenzo[b][1,4]dioxin-2-yl)methyl)piperazin-1-yl)-1,2,5-thiadiazol-3-yl)-3,3-dimethylpyrrolidin-2-one was prepared according to the general procedure A2 using 3,3-dimethyl-1-(4-(piperazin-1-yl)-1,2,5-thiadiazol-3-yl)pyrrolidin-2-one (0.074 g, 0.26 mmol), Na₂CO₃ (0.042 g, 0.39 mmol), (2R)-2-(bromomethyl)-2,3-dihydro-1,4-benzodioxin (0.066 g, 0.29 mmol) and DMF (1 ml). The evaporation residue was purified by reverse phase column chromatography (0.1% NH₄OH-acetonitrile) to afford 0.039 g of (5)-1-(4-(4-((2,3-dihydrobenzo[b][1,4]dioxin-2-yl)methyl)piperazin-1-yl)-1,2,5-thiadiazol-3-yl)-3,3-dimethylpyrrolidin-2-one as white solid.

¹H NMR (400 MHz, CDCl₃) δ ppm 1.26 (6H, s), 2.07 (2H, t), 2.59-2.69 (3H, m), 2.69-2.77 (3H, m), 3.31-3.41 (4H, m), 3.78 (2H, t), 4.02 (1H, dd), 4.29-4.36 (2H, m), 6.81-6.91 (4H, m)

EXAMPLE 18: (S)-4-(4-((2,3-Dihydrobenzo[b][1,4]dioxin-2-yl)methyl)piperazin-1-yl)-N-(pyrimidin-2-yl)-1,2,5-thiadiazol-3-amine Step 1: tert-Butyl 4-(4-(pyrimidin-2-ylamino)-1,2,5-thiadiazol-3-yl)piperazine-1-carboxylate To a solution of tert-butyl 4-(4-chloro-1,2,5-thiadiazol-3-yl)piperazine-1-carboxylate (4.0 g, 13.1 mmol)) (prepared as in step 1 of Example 16) in toluene were added 2-amino pyrimidine (1.5 g, 15.7 mmol) and NaOtBu (1.89 g, 19.7 mmol) at room temperature. The solution was degassed with argon for 30 min. Pd$_2$(dba)$_3$ (0.602 g, 0.65 mmol) and Ruphos (0.61 g, 1.3 mmol) were added to the reaction mixture. The reaction mixture was heated at 100° C. in a sealed tube for 16 h. The reaction mixture was cooled to room temperature, filtered through Celite pad followed by a wash with EtOAc. Filtrate was concentrated under reduced pressure. Purification of the evaporation residue by flash chromatography (EtOAc in petroleum ether) afforded 0.6 g of tert-butyl 4-(4-(pyrimidin-2-ylamino)-1,2,5-thiadiazol-3-yl)piperazine-1-carboxylate as pale yellow solid. m/z [M+1]: 364.2

Step 2: Hydrochloride Salt of 4-(piperazin-1-yl)-N-(pyrimidin-2-yl)-1,2,5-thiadiazol-3-amine An ice cold stirred solution of tert-butyl 4-(4-(pyrimidin-2-ylamino)-1,2,5-thiadiazol-3-yl)piperazine-1-carboxylate (0.4 g, 1.1 mmol) in HCl-dioxane (20.0 mL) was allowed to warm up towards room temperature for 3 h. The reaction mixture was concentrated under reduced pressure Trituration of the evaporation residue with n-pentane afforded 0.40 g of hydrochloride salt of 4-(piperazin-1-yl)-N-(pyrimidin-2-yl)-1,2,5-thiadiazol-3-amine as off white solid. m/z [M+1]: 264.1

Step 3: (S)-4-(4-((2,3-Dihydrobenzo[b][1,4]dioxin-2-yl)methyl)piperazin-1-yl)-N-(pyrimidin-2-yl)-1,2,5-thiadiazol-3-amine (S)-4-(4-((2,3-Dihydrobenzo[b][1,4]dioxin-2-yl)methyl) piperazin-1-yl)-N-(pyrimidin-2-yl)-1,2,5-thiadiazol-3-amine was prepared according to the general procedure A2 using hydrochloride salt of 4-(piperazin-1-yl)-N-(pyrimidin-2-yl)-1,2,5-thiadiazol-3-amine (0.130 g, 0.43 mmol), Na$_2$CO$_3$ (0.115 g, 1.08 mmol), (2R)-2-(bromomethyl)-2,3-dihydro-1,4-benzodioxin (0.109 g, 0.48 mmol) and DMF (1.5 ml). The product was isolated by cooling and filtering the reaction mixture. Washing the precipitate with water and subsequent drying in vacuum oven (30° C.) afforded 0.090 g of (S)-4-(4-((2,3-dihydrobenzo[b][1,4]dioxin-2-yl) methyl)piperazin-1-yl)-N-(pyrimidin-2-yl)-1,2,5-thiadiazol-3-amine as yellowish solid.
$^1$H NMR (400 MHz, CDCl$_3$) δ ppm 2.64-2.86 (6H, m), 3.26-3.33 (4H, m), 4.00-4.08 (1H, m), 4.30-4.38 (2H, m), 6.82-6.91 (4H, m), 6.94 (1H, t), 7.63 (1H, br s), 8.61 (2H, d)

EXAMPLE 19: (S)-4-(4-((2,3-Dihydrobenzo[b][1,4] dioxin-2-yl)methyl)piperazin-1-yl)-N-(pyrimidin-4-yl)-1,2,5-thiadiazol-3-amine Step 1: tert-Butyl 4-(4-(pyrimidin-4-ylamino)-1,2,5-thiadiazol-3-yl)piperazine-1-carboxylate To a solution of tert-butyl 4-(4-chloro-1,2,5-thiadiazol-3-yl)piperazine-1-carboxylate (3.0 g, 9.868 mmol) (prepared as in step 1 of Example 16) in toluene were added pyrimidin-4-amine (0.935 g, 9.868 mmol) and NaOtBu (1.47 g, 14.802 mmol) at room temperature. Solution was degassed with argon for 30 min. Pd$_2$(dba)$_3$ (451 mg, 0.493 mmol) followed by RuPhos (460 mg, 0.986 mmol) were added at room temperature and the reaction mixture was heated at 100° C. in a sealed tube for 16 h. The reaction mixture was cooled to room temperature, filtered through Celite pad followed by a wash with EtOAc. Filtrate was concentrated under reduced pressure. Purification of the evaporation residue by flash chromatography (EtOAc in petroleum ether) afforded 0.70 g of tert-butyl 4-(4-(pyrimidin-4-ylamino)-1,2,5-thiadiazol-3-yl)piperazine-1-carboxylate as pale yellow solid.

Step 2: Hydrochloride Salt of 4-(piperazin-1-yl)-N-(pyrimidin-4-yl)-1,2,5-thiadiazol-3-amine An ice cold stirred solution of tert-butyl 4-(4-(pyrimidin-4-ylamino)-1,2,5-thiadiazol-3-yl)piperazine-1-carboxylate (0.7 g, 1.92 mmol) in HCl-dioxane (20.0 mL) was allowed to warm up towards room temperature for 3 h. The reaction mixture was concentrated under reduced pressure. Trituration of the evaporation residue with n-pentane afforded 0.50 g of hydrochloride salt of 4-(piperazin-1-yl)-N-(pyrimidin-4-yl)-1,2,5-thiadiazol-3-amine as pale yellow solid. m/z [M+1]: 264.1

Step 3: (S)-4-(4-((2,3-Dihydrobenzo[b][1,4]dioxin-2-yl)methyl)piperazin-1-yl)-N-(pyrimidin-4-yl)-1,2,5-thiadiazol-3-amine (S)-4-(4-((2,3-Dihydrobenzo[b][1,4]dioxin-2-yl)methyl) piperazin-1-yl)-N-(pyrimidin-4-yl)-1,2,5-thiadiazol-3-amine was prepared according to the general procedure A2 using hydrochloride salt of 4-(piperazin-1-yl)-N-(pyrimidin-4-yl)-1,2,5-thiadiazol-3-amine (0.20 g, 0.67 mmol), Na$_2$CO$_3$ (0.177 g, 1.67 mmol), (2R)-2-(bromomethyl)-2,3-dihydro-1,4-benzodioxin (0.168 g, 0.73 mmol) and DMF (2 ml). The evaporation residue was purified by reverse phase column chromatography (0.1% NH$_4$OH-acetonitrile) to afford 0.023 g of (S)-4-(4-((2,3-dihydrobenzo[b][1,4]dioxin-2-yl) methyl)piperazin-1l-yl)-1,2,5-thiadiazol-3-amine as white solid.
$^1$H NMR (400 MHz, CDCl$_3$) δ ppm 2.66-2.88 (6H, m), 3.24-3.32 (4H, m), 4.00-4.09 (1H, m), 4.29-4.41 (2H, m), 6.82-6.92 (4H, m), 7.62 (1H, m), 8.19 (1H, dd), 8.60 (1H, d), 8.83 (1H, d).

EXAMPLE 20: (S)-1-(5-(4-((2,3-Dihydrobenzo[b] [1,4]dioxin-2-yl)methyl)piperazin-1-yl)thiazol-4-yl) pyrrolidin-2-one Step 1: 1-(Thiazol-4-yl)pyrrolidin-2-one To a solution of 4-bromothiazole (10.0 g, 60.97 mmol) in 1,4-Dioxane was added pyrrolidone (4.63 mL, 60.97 mmol), N$^1$,N$^2$-dimethyl ethylene diamine (1.98 mL, 18.29 mmol), CuI (11.61 g, 60.97 mmol) and K$_3$PO$_4$ (25.88 g, 121.95 mmol) at RT and the mixture was heated to 100° C. for 16 h. The reaction mixture was filtered and concentrated. Purification of the evaporation residue by column chromatography (15% EtOAc in petroleum ether) afforded 4.5 g of 1-(thiazol-4-yl)pyrrolidin-2-one as brown solid. m/z [M+1]: 169.1

Step 2: 1-(5-Bromothiazol-4-yl)pyrrolidin-2-one

To a solution of 1-(thiazol-4-yl)pyrrolidin-2-one (6.5 g, 168.0 mmol) in 1, 2-dichloroetane (150 mL) was added N-bromosuccinimide (8.16 g, 46.4 mmol) at 0° C. and the resulting reaction mixture was stirred for 1 h. The reaction mixture was quenched with water and the mixture was extracted with dichloromethane. The combined organic layers were dried (Na$_2$SO$_4$) and concentrated under reduced pressure. Purification of the evaporation residue by flash chromatography (20% EtOAc in petroleum ether) afforded 6.0 g of 1-(5-bromothiazol-4-yl)pyrrolidin-2-one as brown solid. m/z [M+1]:247.0

Step 3: tert-Butyl 4-(4-(2-oxopyrrolidin-1-yl)thiazol-5-yl)piperazine-1-carboxylate Pd(OAc)$_2$ (0.054 g, 0.02 mmol), RuPhos (0.340 g, 0.06 mmol) and Cs$_2$CO$_3$ (5.14 g, 15.78 mmol) were added to degassed t-BuOH (60 ml) under N$_2$. To the resulting mixture were added 1-(5-bromothiazol-4-yl)pyrrolidin-2-one (3.0 g, 12.14 mmol) and 1-Boc piperazine (2.71 g, 14.57 mmol). The mixture was refluxed under N$_2$ for 16 h. The reaction mixture was cooled to room temperature and diluted with MTBE. The mixture was filtered through a Celite pad and the filtrate was evaporated to dryness. Purification of the evaporation residue by column chromatography (2% MeOH in CH$_2$C$_{12}$) afforded 2.0 g of tert-butyl 4-(4-(2-oxopyrrolidin-1-yl)thiazol-5-yl)piperazine-1-carboxylate as pale yellow solid. m/z [M+1]:353.2.

Step 4: 1-(5-(Piperazin-1-yl)thiazol-4-yl)pyrrolidin-2-one hydrochloride

To a solution of tert-butyl 4-(4-(2-oxopyrrolidin-1-yl)thiazol-5-yl)piperazine-1-carboxylate (0.60 g, 1.70 mmol) in 1,4-Dioxane (5 ml) was added solution of HCl in-1,4-Dioxane (20 ml) at 0° C. and the mixture was stirred at room temperature for 4 h. The reaction mixture was concentrated under reduced pressure. Trituration of the evaporation residue with n-pentane and diethyl ether afforded 0.45 g of 1-(5-(piperazin-1-yl)thiazol-4-yl)pyrrolidin-2-one hydrochloride as off white solid. m/z [M+1]: 253.1.

Step 5: (S)-1-(5-(4-((2,3-Dihydrobenzo[b][1,4]dioxin-2-yl)methyl)piperazin-1-yl)thiazol-4-yl)pyrrolidin-2-one (S)-1-(5-(4-((2,3-Dihydrobenzo[b][1,4]dioxin-2-yl)methyl)piperazin-1-yl)thiazol-4-yl)pyrrolidin-2-one was prepared according to the general procedure A2 using 1-(5-(piperazin-1-yl)thiazol-4-yl)pyrrolidin-2-one hydrochloride (0.150 g, 0.52 mmol), Na$_2$CO$_3$ (0.138 g, 1.30 mmol), (2R)-2-(bromomethyl)-2,3-dihydro-1,4-benzodioxin (0.131 g, 0.57 mmol) and DMF (1.7 ml). The evaporation residue was purified by reverse phase column chromatography (0.1% NH$_4$OH-acetonitrile) to afford 0.125 g of (S)-1-(5-(4-((2,3-dihydrobenzo[b][1,4]dioxin-2-yl)methyl)piperazin-1-yl)thiazol-4-yl)pyrrolidin-2-one.
$^1$H NMR (400 MHz, CDCl$_3$) δ ppm 2.16-2.25 (2H, m), 2.51-2.57 (2H, m), 2.61-2.77 (6H, m), 2.96-3.05 (4H, m), 3.81 (2H, t), 3.98-4.05 (1H, m), 4.27-4.35 (2H, m), 6.81-6.91 (4H, m), 8.39 (1H, s).

EXAMPLE 21: 1-(4-(4-(((S)-2,3-Dihydrobenzo[b][1,4]dioxin-2-yl)methyl)piperazin-1-yl)-1,2,5-thiadiazol-3-yl)-3-methylpyrrolidin-2-one Step 1: tert-Butyl 4-(4-(2-oxopyrrolidin-1-yl)-1,2,5-thiadiazol-3-yl)piperazine-1-carboxylate To an ice cold stirred solution of tert-butyl 4-(4-amino-1,2,5-thiadiazol-3-yl)piperazine-1-carboxylate (10.0 g, 35.08 mmol) (prepared as in Example 16 step 1-2) in dry THF (100 mL) was added NaH (60%) (3.50 g, 87.7 mmol) and stirred for 15 minutes. To the reaction mixture was added 4-bromo butyryl chloride (4.90 ml, 42.1 mmol) drop wise and the mixture was stirred at RT for 16 h. The reaction mixture was quenched with cold water, extracted with EtOAc (3×150 ml) and washed with water (2×100 ml). The organic layer was dried (Na$_2$SO$_4$) and concentrated under reduced pressure. Purification of the evaporation residue by flash chromatography (50% EtOAc in petroleum ether) afforded 8.0 g of tert-butyl 4-(4-(2-oxopyrrolidin-1-yl)-1,2,5-thiadiazol-3-yl)piperazine-1-carboxylate as pale yellow solid. m/z [M+1]:354.2.

Step 2: tert-Butyl 4-(4-(3-methyl-2-oxopyrrolidin-1-yl)-1,2,5-thiadiazol-3-yl)piperazine-1-carboxylate To a stirred solution of tert-butyl 4-(4-(2-oxopyrrolidin-1-yl)-1,2,5-thiadiazol-3-yl)piperazine-1-carboxylate (500 mg, 1.42 mmol) in dry THF (10 mL) was added lithium di-isopropylamide (2 M in THF) (0.9 mL, 1.70 mmol) at −78° C. The reaction mixture was stirred at −78° C. for 1 h. MeI (0.14 mL, 2.12 mmol) was added and the stirring was continued at −78° C. for 3 h. The reaction mixture was quenched with NH$_4$Cl solution (40 mL) and extracted with EtOAc (3×30 mL). The combined organic layers were washed with water, brine then dried (Na$_2$SO$_4$) and concentrated under reduced pressure. Purification of the evaporation residue by flash chromatography (EtOAc/petroleum ether) afforded 0.15 g of tert-butyl 4-(4-(3-methyl-2-oxopyrrolidin-1-yl)-1,2,5-thiadiazol-3-yl)piperazine-1-carboxylate as a sticky semi solid. m/z [M+1]:368.2

Step 3: 3-Methyl-1-(4-(piperazin-1-yl)-1,2,5-thiadiazol-3-yl)pyrrolidin-2-one hydrochloride A stirred solution of tert-butyl 4-(4-(3-methyl-2-oxopyrrolidin-1-yl)-1,2,5-thiadiazol-3-yl)piperazine-1-carboxylate (150 mg, 0.41 mmol) HCl-dioxane (10.0 mL) was stirred at 0° C.→RT for 3 h. The reaction mixture was concentrated under reduced pressure. Trituration of the evaporation residue with n-pentane afforded 0.115 g of 3-methyl-1-(4-(piperazin-1-yl)-1,2,5-thiadiazol-3-yl)pyrrolidin-2-one hydrochloride as off white solid. m/z [M+1]:268.1

Step 4: (1-(4-(4-(((S)-2,3-Dihydrobenzo[b][1,4]dioxin-2-yl)methyl)piperazin-1-yl)-1,2,5-thiadiazol-3-yl)-3-methylpyrrolidin-2-one (1-(4-(4-(((S)-2,3-dihydrobenzo[b][1,4]dioxin-2-yl)methyl)piperazin-1-yl)-1,2,5-thiadiazol-3-yl)-3-methylpyrrolidin-2-one was prepared according to the general procedure A2 using 3-methyl-1-(4-(piperazin-1-yl)-1,2,5-thiadiazol-3-yl)pyrrolidin-2-one hydrochloride (0.10 g, 0.33 mmol), Na$_2$CO$_3$ (0.080 g, 0.76 mmol), (2R)-2-(bromomethyl)-2,3-dihydro-1,4-benzodioxin (0.090 g, 0.40 mmol) and sulfolane (1 ml). The evaporation residue was purified by reverse phase column chromatography (NH$_{40}$H-acetonitrile) to afford 0.027 g of (1-(4-(4-(((S)-2,3-dihydrobenzo[b][1,4]dioxin-2-yl)methyl)piperazin-1-yl)-1,2,5-thiadiazol-3-yl)-3-methylpyrrolidin-2-one as oily solid.
$^1$H NMR (400 MHz, CDCl$_3$) δ ppm 1.30 (3H, s), 1.70-1.9 (1H, m), 2.39-2.49 (1H, m), 2.59-2.77 (7H, m), 3.31-3.42 (4H, m), 3.74-3.83 (2H, m), 4.00-4.05 (1H, m), 4.29-4.36 (2H, m), 6.81-6.91 (4H, m).

EXAMPLE 22: (S)-2-(4-((2,3-Dihydrobenzo[b][1,4]dioxin-2-yl)methyl)piperazin-1-yl)-1,3,4-thiadiazole Step 1: (S)-tert-Butyl 4-((2,3-dihydrobenzo[b][1,4]dioxin-2-yl)methyl)piperazine-1-carboxylate Prepared using general procedure A1 from tert-butyl piperazine-1-carboxylate (1.23 g, 6.59 mmol), (R)-2-(bromomethyl)-2,3-dihydrobenzo[b][1,4]dioxine (1.51 g, 6.59 mmol), and K$_2$CO$_3$ (1.37 g, 9.89 mmol) in ACN (14 ml). The crude product was purified by flash chromatography yielding 1.32 g of (S)-tert-butyl 4-((2,3-dihydrobenzo[b][1,4]dioxin-2-yl)methyl)piperazine-1-carboxylate. m/z=335.4 (M+1)$^+$.

Step 2: (S)-1-((2,3-Dihydrobenzo[b][1,4]dioxin-2-yl)methyl)piperazine dihydrochloride (S)-tert-Butyl 4-((2,3-dihydrobenzo[b][1,4]dioxin-2-yl)methyl)piperazine-1-carboxylate (1.32 g, 3.95 mmol) in MeOH (10 ml) was treated with 4 M HCl in 1,4-dioxane (5.92 ml, 23.7 mmol) for 3 h at RT. Solvents were evaporated off and the residue was triturated with Et$_2$O yielding 1.16 g (S)-1-((2,3-dihydrobenzo[b][1,4]dioxin-2-yl)methyl)piperazine dihydrochloride. m/z=235.3 (M+1)$^+$.

Step 3: (S)-2-(4-((2,3-Dihydrobenzo[b][1,4]dioxin-2-yl)methyl)piperazin-1-yl)-1,3,4-thiadiazole A Mixture of (S)-1-((2,3-dihydrobenzo[b][1,4]dioxin-2-yl)methyl)piperazine dihydrochloride (0.20 g, 0.65 mmol), 2-bromo-1,3,4-thiadiazole (0.16 g, 0.98 mmol), and DIPEA (0.45 ml, 0.34 g, 2.60 mmol) in NMP (4 ml) was heated MW reactor for 3 h at 150° C. The reaction mixture was diluted with water and extracted with EtOAc. Combined organic phases were washed with water and brine, dried and evaporated to dryness. The residue was purified by flash chromatography yielding 53 mg (S)-2-(4-((2,3-dihydrobenzo[b][1,4]dioxin-2-yl)methyl)piperazin-1-yl)-1,3,4-thiadiazole.
$^1$H NMR (400 MHz, CDCl$_3$): 2.62-2.82 (6H, m), 3.52-3.67 (4H, m), 4.00-4.08 (1H, m), 4.27-4.39 (2H, m), 6.79-6.93 (4H, m), 8.46 (1H, s).

EXAMPLE 23: (S)-3-(4-((2,3-Dihydrobenzo[b][1,4]dioxin-2-yl)methyl)piperazin-1-yl)-5-(methoxymethyl)-1,2,4-oxadiazole Step 1: tert-Butyl 4-(5-(methoxymethyl)-1,2,4-oxadiazol-3-yl)piperazine-1-carboxylate A solution of tert-Butyl 4-(5-(hydroxymethyl)-1,2,4-oxadiazol-3-yl)piperazine-1-carboxylate (1.20 g, 4.22 mmol, prepared according to WO 2004/006846) in THF (10 ml) was cooled to 0° C. and treated with 60% NaH dispersion (0.25 g, 6.33 mmol). After 30 min MeI (0.39 ml, 0.90 g, 6.33 mmol) was added and stirring at 0° C. continued for 15 min. The resulting mixture was stirred overnight at RT, diluted with water and extracted with EtOAc. The combined extracts were washed with water and brine, dried and evaporated to dryness yielding crude 1.17 g tert-butyl 4-(5-(methoxymethyl)-1,2,4-oxadiazol-3-yl)piperazine-1-carboxylate.
$^1$H NMR (400 MHz, CDCl$_3$): 1.48 (9H, s), 3.40-3.48 (4H, m), 3.49-3.55 (4H, m), 3.50 (3H, s), 4.55 (2H, s).

Step 2: 5-(Methoxymethyl)-3-(piperazin-1-yl)-1,2,4-oxadiazole hydrochloride

Crude tert-butyl 4-(5-(methoxymethyl)-1,2,4-oxadiazol-3-yl)piperazine-1-carboxylate (1.17 g, 3.92 mmol) in EtOAc (10 ml) was treated with 4 M HCl in 1,4-dioxane (4.90 ml, 19.6 mmol). The resulting mixture was stirred overnight at RT, evaporated to dryness. The residue was triturated with Et$_2$O yielding 0.86 g 5-(methoxymethyl)-3-(piperazin-1-yl)-1,2,4-oxadiazole hydrochloride. m/z=199.2 (M+1)$^+$.

Step 3: (S)-3-(4-((2,3-Dihydrobenzo[b][1,4]dioxin-2-yl)methyl)piperazin-1-yl)-5-(methoxymethyl)-1,2,4-oxadiazole Prepared using general procedure A1 from 5-(methoxymethyl)-3-(piperazin-1-yl)-1,2,4-oxadiazole hydrochloride (0.20 g, 0.85 mmol), (R)-2-(bromomethyl)-2,3-dihydrobenzo[b][1,4]dioxine (0.20 g, 0.85 mmol), K$_2$CO$_3$ (0.18 g, 1.28 mmol), and DIPEA (0.22 ml, 0.17 g, 1.28 mmol) in ACN (4 ml) yielding 0.10 g (S)-3-(4-((2,3-dihydrobenzo[b][1,4]dioxin-2-yl)methyl)piperazin-1-yl)-5-(methoxymethyl)-1,2,4-oxadiazole.
$^1$H NMR (400 MHz, CDCl$_3$): 2.56-2.78 (6H, m), 3.46-3.54 (7H, m), 3.99-4.06 (1H, m), 4.29-4.36 (2H, m), 4.54 (2H, s), 6.81-6.91 (4H, m).

EXAMPLE 24: (S)-1-(4-(4-((2,3-Dihydrobenzo[b][1,4]dioxin-2-yl)methyl)piperazin-1-yl)-1,2,5-thiadiazol-3-yl)pyrrolidin-2-one Step 1: tert-Butyl 4-(4-(2-oxopyrrolidin-1-yl)-1,2,5-thiadiazol-3-yl)piperazine-1-carboxylate 2-Pyrrolidinone (0.14 ml, 0.15 g, 1.80 mmol) in DMF (4 ml) was treated with 60% NaH dispersion (72 mg, 1.80 mmol). After 30 min, tert-butyl 4-(4-chloro-1,2,5-thiadiazol-3-yl)piperazine-1-carboxylate (0.50 g, 1.64 mmol, prepared according to WO 2004/083235) was added. After stirring overnight at RT, the mixture was heated to 60° C. for 4 h. The resulting mixture was diluted with water and extracted with EtOAc. The combined organic phases were washed with water and brine, dried and evaporated. The residue was purified by flash chromatography yielding 81 mg tert-butyl 4-(4-(2-oxopyrrolidin-1-yl)-1,2,5-thiadiazol-3-yl)piperazine-1-carboxylate. m/z=354.4 (M+1)$^+$.

Step 2: 1-(4-(Piperazin-1-yl)-1,2,5-thiadiazol-3-yl)pyrrolidin-2-one hydrochloride tert-Butyl 4-(4-(2-oxopyrrolidin-1-yl)-1,2,5-thiadiazol-3-yl)piperazine-1-carboxylate (81 mg, 0.23 mmol) in EtOAc (1 ml) was treated with 4 M HCl in 1,4-dioxane (0.43 ml, 1.72 mmol) at RT for 5 d. The resulting mixture was evaporated to dryness yielding 75 mg crude 1-(4-(piperazin-1-yl)-1,2,5-thiadiazol-3-yl)pyrrolidin-2-one hydrochloride. m/z=254.2 (M+1)$^+$.

Step 3: (S)-1-(4-(4-((2,3-Dihydrobenzo[b][1,4]dioxin-2-yl)methyl)piperazin-1-yl)-1,2,5-thiadiazol-3-yl)pyrrolidin-2-one Prepared using general procedure A1 from crude 1-(4-(piperazin-1-yl)-1,2,5-thiadiazol-3-yl)pyrrolidin-2-one hydrochloride (75 mg, 0.26 mmol), (R)-2-(bromomethyl)-2,3-dihydrobenzo[b][1,4]dioxine (59 mg, 0.26 mmol), and DIPEA (0.14 ml, 0.10 g, 0.78 mmol) in ACN (1 ml) yielding 10 mg (S)-1-(4-(4-((2,3-dihydrobenzo[b][1,4]dioxin-2-yl)methyl)piperazin-1-yl)-1,2,5-thiadiazol-3-yl)pyrrolidin-2-one.
$^1$H NMR (400 MHz, CDCl$_3$): 2.18-2.30 (2H, m), 2.57 (2H, t), 2.60-2.78 (6H, m), 3.32-3.43 (4H, m), 3.87 (2H, t), 3.98-4.07 (1H, m), 4.28-4.37 (2H, m), 6.81-6.91 (4H, m).

EXAMPLE 25: (S)-1-(5-(4-((2,3-Dihydrobenzo[b][1,4]dioxin-2-yl)methyl)piperazin-1-yl)-1,3,4-thiadiazol-2-yl)imidazolidin-2-one

Step 1: 1-(5-Bromo-1,3,4-thiadiazol-2-yl)imidazolidin-2-one

2-Amino-5-bromo-[1,3,4]thiadiazole (0.30 g, 1.67 mmol) in THF (10 ml) was treated with 2-chloroethyl isocyanate (0.14 ml, 0.18 g, 1.67 mmol). After 1 h LHMDS (0.47 g, 2.83 mmol) was added and stirring was continued for 3 d. MeOH was added and solvents were evaporated off. The residue was dissolved in EtOAc, washed with water and brine, dried and evaporated. The residue was triturated with DCM yielding 0.25 g 1-(5-bromo-1,3,4-thiadiazol-2-yl)imidazolidin-2-one. m/z=251.2 (M+1)$^+$.

Step 2: (S)-1-(5-(4-((2,3-Dihydrobenzo[b][1,4]dioxin-2-yl)methyl)piperazin-1-yl)-1,3,4-thiadiazol-2-yl)imidazolidin-2-one A mixture of 1-(5-bromo-1,3,4-thiadiazol-2-yl)imidazolidin-2-one (0.16 g, 0.64 mmol), (S)-1-((2,3-dihydrobenzo[b][1,4]dioxin-2-yl)methyl)piperazine dihydrochloride (0.20 g, 0.64 mmol), and DIPEA (0.56 ml, 0.42 g, 3.21 mmol) in 2-propanol (5 ml) was microwave heated for 21 h at 150° C. Solvent was evaporated off and the residue was dissolved in EtOAc, washed with water and brine, dried and evaporated. The residue was purified by flash chromatography yielding 31 mg (S)-1-(5-(4-((2,3-dihydrobenzo[b][1,4]dioxin-2-yl)methyl)piperazin-1-yl)-1,3,4-thiadiazol-2-yl)imidazolidin-2-one.
$^1$H NMR (400 MHz, CDCl$_3$): 2.61-2.79 (6H, m), 3.45-3.55 (4H, m), 3.69 (2H, t), 3.98-4.07 (1H, m), 4.15-4.22 (2H, m), 4.28-4.36 (2H, m), 5.11 (1H, br s), 6.80-6.92 (4H, m).

EXAMPLE 26: (S)-3-(4-(4-((2,3-Dihydrobenzo[b][1,4]dioxin-2-yl)methyl)piperazin-1-yl)-1,2,5-thiadiazol-3-yl)oxazolidin-2-one

Step 1: tert-Butyl 4-(4-(2-oxooxazolidin-3-yl)-1,2,5-thiadiazol-3-yl)piperazine-1-carboxylate In a sealed tube, to a solution of tert-butyl 4-(4-chloro-1,2,5-thiadiazol-3-yl)piperazine-1-carboxylate (4.00 g, 13.2 mmol) and oxazolidin-2-one (1.14 g, 13.2 mmol) in dioxane (40 ml) were added CuI (25 mg, 0.14 mmol), N$^1$,N$^2$-dimethylethylene-1,2-diamine (0.14 ml, 0.12 g, 1.32 mmol) and K$_3$PO$_4$ (5.58 g, 212.3 mmol) at RT. The reaction mixture was heated to 100° C. for 16 h. The mixture was filtered through a Celite pad and evaporated to dryness. The residue was purified by flash chromatography yielding 0.70 g tert-butyl 4-(4-(2-oxooxazolidin-3-yl)-1,2, 5-thiadiazol-3-yl)piperazine-1-carboxylate. m/z=356.2 (M+1)$^+$.

Step 2: 3-(4-(Piperazin-1-yl)-1,2,5-thiadiazol-3-yl)oxazolidin-2-one hydrochloride To an ice cold stirred solution of tert-butyl 4-(4-(2-oxooxazolidin-3-yl)-1,2,5-thiadiazol-3-yl)piperazine-1-carboxylate (0.70 g, 1.97 mmol) in 4 M HCl in dioxane (10 m, 40 mmol) was stirred at RT for 2 h. The solvent was evaporated off and the residue was triturated with pentane yielding 0.55 g 3-(4-(piperazin-1-yl)-1,2,5-thiadiazol-3-yl)oxazolidin-2-one hydrochloride. m/z=256.0 (M+1)$^+$.

Step 3: (S)-3-(4-(4-((2,3-Dihydrobenzo[b][1,4]dioxin-2-yl)methyl)piperazin-1-yl)-1,2,5-thiadiazol-3-yl)oxazolidin-2-one Prepared using general procedure A1 from 3-(4-(piperazin-1-yl)-1,2,5-thiadiazol-3-yl)oxazolidin-2-one hydrochloride (0.11 g, 0.39 mmol), (R)-2-(bromomethyl)-2,3-dihydrobenzo[b][1,4]dioxine (0.10 g, 0.43 mmol), and K$_2$CO$_3$ (0.11 g, 0.78 mmol) in ACN (2 ml) yielding 74 mg (S)-3-(4-(4-((2,3-dihydrobenzo[b][1,4]dioxin-2-yl)methyl)piperazin-1-yl)-1,2,5-thiadiazol-3-yl)oxazolidin-2-one. $^1$H NMR (400 MHz, CDCl$_3$): 2.60-2.79 (6H, m), 3.37-3.48 (4H, m), 3.98-4.06 (1H, m), 4.13 (2H, t), 4.27-4.38 (2H, m), 4.56 (2H, t), 6.81-6.92 (4H, m).

EXAMPLE 27: (S)-4-(4-((2,3-Dihydrobenzo[b][1,4]dioxin-2-yl)methyl)piperazin-1-yl)-1,2,5-thiadiazole-3-carboxamide

Step 1: Methyl 4-(4-(tert-butoxycarbonyl)piperazin-1-yl)-1,2,5-thiadiazole-3-carboxylate tert-Butyl 4-(4-chloro-1,2,5-thiadiazol-3-yl)piperazine-1-carboxylate (10.0 g, 32.8 mmol) in MeOH (150 ml) was treated with TEA (7.20 ml, 5.23 g, 49.3 mmol) and degassed with argon for 15 min. (BINAP)PdCl$_2$ was added to the reaction mixture and stirred in pressure vessel for 16 h at 100° C. under CO (100 psi). The reaction mixture was cooled to RT and filtered through Celite pad, washed with methanol. Filtrate was concentrated under reduced pressure to obtain crude compound which was purified by flash chromatography yielding 1.30 g methyl 4-(4-(tert-butoxycarbonyl)piperazin-1-yl)-1,2,5-thiadiazole-3-carboxylate. m/z=329.2 (M+1)$^+$.

Step 2: tert-Butyl 4-(4-carbamoyl-1,2,5-thiadiazol-3-yl)piperazine-1-carboxylate In sealed tube NH$_3$ gas was bubbled into MeOH (25 ml) for 20 min at −30° C. and methyl 4-(4-(tert-butoxycarbonyl)piperazin-1-yl)-1,2,5-thiadiazole-3-carboxylate (0.70 g, 2.13 mmol) was added. The reaction mixture was heated at 90° C. for 16 h, cooled and evaporated. The residue was purified by flash chromatography yielding 0.50 g tert-butyl 4-(4-carbamoyl-1,2,5-thiadiazol-3-yl)piperazine-1-carboxylate. m/z=314.2 (M+1)$^+$.

Step 3: 4-(Piperazin-1-yl)-1,2,5-thiadiazole-3-carboxamide hydrochloride

Ice cold stirred solution tert-butyl 4-(4-carbamoyl-1,2,5-thiadiazol-3-yl)piperazine-1-carboxylate of (0.55 g, 1.76 mmol) in 4 M HCl in 1,4-dioxane (10 ml, 40 mmol) was allowed to warm to RT and stirred for 16 h and evaporated to dryness. The residue was triturated with pentane yielding 0.55 g 4-(Piperazin-1-yl)-1,2,5-thiadiazole-3-carboxamide hydrochloride. m/z=214.1 (M+1)$^+$.

Step 4: (S)-4-(4-((2,3-Dihydrobenzo[b][1,4]dioxin-2-yl)methyl)piperazin-1-yl)-1,2,5-thiadiazole-3-carboxamide Prepared using general procedure A1 from 4-(piperazin-1-yl)-1,2,5-thiadiazole-3-carboxamide hydrochloride (0.15 g, 0.60 mmol), (R)-2-(bromomethyl)-2,3-dihydrobenzo[b][1,4]dioxine (0.17 g, 0.72 mmol), and K$_2$CO$_3$ (0.21 g, 1.50 mmol) in ACN (2 ml) yielding 88 mg (S)-4-(4-((2,3-dihydrobenzo[b][1,4]dioxin-2-yl)methyl)piperazin-1-yl)-1,2,5-thiadiazole-3-carboxamide.

$^1$H NMR (400 MHz, DMSO-d$_6$): 2.54-2.70 (6H, m), 3.37-3.47 (4H, m), 3.94-4.02 (1H, m), 4.28-4.42 (2H, m), 6.78-6.90 (4H, m), 7.84 (1H, br s), 8.18 (1H, br s).

EXAMPLE 28: (S)-1-(4-(4-((2,3-Dihydrobenzo[b][1,4]dioxin-2-yl)methyl)piperazin-1-yl)-1,2,5-thiadiazol-3-yl)-3-methylimidazolidin-2-one Step 1: tert-Butyl 4-(4-(3-methyl-2-oxoimidazolidin-1-yl)-1,2,5-thiadiazol-3-yl)piperazine-1-carboxylate To an ice cold stirred solution of tert-butyl 4-(4-(2-oxoimidazolidin-1-yl)-1,2,5-thiadiazol-3-yl)piperazine-1-carboxylate (0.20 g, 0.56 mmol) in THF (10 m0) was added 60% NaH dispersion and the resulting mixture was stirred at 0° C. for 30 min. MeI (40 µl, 0.68 mmol) was added to the reaction mixture and allowed to stir at RT for 6 h. The reaction mixture was quenched with water and extracted with EtOAc. The combine organic layers were washed with water and brine. The organic layer was dried and concentrated to obtain the crude compound which was purified by flash chromatography yielding 0.14 g tert-butyl 4-(4-(3-methyl-2-oxoimidazolidin-1-yl)-1,2,5-thiadiazol-3-yl)piperazine-1-carboxylate. m/z=369.2 (M+1)$^+$.

Step 2: 1-Methyl-3-(4-(piperazin-1-yl)-1,2,5-thiadiazol-3-yl)imidazolidin-2-one hydrochloride tert-Butyl 4-(4-(3-methyl-2-oxoimidazolidin-1-yl)-1,2,5-thiadiazol-3-yl)piperazine-1-carboxylate (0.2 g, 0.54 mmol) was added to ice cold 4 M HCl in 1,4-dioxane (10 ml, 40 mmol), allowed to warm to RT and stirred for 2 h. The solvent was evaporated off and the residue was triturated with pentane yielding 0.11 g 1-methyl-3-(4-(piperazin-1-yl)-1,2,5-thiadiazol-3-yl)imidazolidin-2-one hydrochloride. m/z=269.1 (M+1)$^+$.

Step 3: (S)-1-(4-(4-((2,3-Dihydrobenzo[b][1,4]dioxin-2-yl)methyl)piperazin-1-yl)-1,2,5-thiadiazol-3-yl)-3-methylimidazolidin-2-one Prepared using general procedure A1 from 1-methyl-3-(4-(piperazin-1-yl)-1,2,5-thiadiazol-3-yl)imidazolidin-2-one hydrochloride (60 mg, 0.20 mmol), (R)-2-(bromomethyl)-2,3-dihydrobenzo[b][1,4]dioxine (54 mg, 0.24 mmol), and K$_2$CO$_3$ (68 mg, 0.49 mmol) in ACN (2 ml) yielding 34 mg (S)-1-(4-(4-((2,3-dihydrobenzo[b][1,4]dioxin-2-yl)methyl)piperazin-1-yl)-1,2,5-thiadiazol-3-yl)-3-methylimidazolidin-2-one.

$^1$H NMR (400 MHz, CDCl$_3$): 2.60-2.78 (6H, m), 2.91 (3H, s), 3.41-3.49 (4H, m), 3.50-3.57 (2H, m), 3.83-3.90 (2H, m), 3.99-4.06 (1H, m), 4.29-4.37 (2H, m), 6.81-6.91 (4H, m).

EXAMPLE 29: (S)-4-(4-((2,3-Dihydrobenzo[b][1,4]dioxin-2-yl)methyl)piperazin-1-yl)-N-methyl-1,2,5-thiadiazole-3-carboxamide hydrochloride Step 1: tert-Butyl 4-(4-(methylcarbamoyl)-1,2,5-thiadiazol-3-yl)piperazine-1-carboxylate Methylamine gas was bubbled into THF (25 ml) for 20 min at −30° C., then methyl 4-(4-(tert-butoxycarbonyl) piperazin-1-yl)-1,2,5-thiadiazole-3-carboxylate (700 mg, 2.13 mmol) was added, and the reaction mixture was heated at 90° C. for 16 h in a sealed tube. The reaction mixture was concentrated and the residue was purified by flash chromatography yielding 0.60 g tert-butyl 4-(4-(methylcarbamoyl)-1,2,5-thiadiazol-3-yl)piperazine-1-carboxylate. m/z=328.2 (M+1)$^+$.

Step 2: N-methyl-4-(piperazin-1-yl)-1,2,5-thiadiazole-3-carboxamide hydrochloride tert-Butyl 4-(4-(methylcarbamoyl)-1,2,5-thiadiazol-3-yl) piperazine-1-carboxylate (0.65 g, 1.99 mmol) was added to ice cool 4 M HCl in 1,4-dioxane (15 ml, 60 mmol) and the resulting mixture was stirred at RT for 16 h. The solvent was evaporated off and the residue was triturated with pentane yielding 0.54 g N-methyl-4-(piperazin-1-yl)-1,2,5-thiadiazole-3-carboxamide hydrochloride. m/z=228.2 (M+1)$^+$.

Step 3: (S)-4-(4-((2,3-Dihydrobenzo[b][1,4]dioxin-2-yl)methyl)piperazin-1-yl)-N-methyl-1,2,5-thiadiazole-3-carboxamide hydrochloride Prepared using general procedure A1 from N-methyl-4-(piperazin-1-yl)-1,2,5-thiadiazole-3-carboxamide hydrochloride (0.15 g, 0.57 mmol), (R)-2-(bromomethyl)-2,3-dihydrobenzo[b][1,4]dioxine (0.16 g, 0.68 mmol), and K$_2$CO$_3$ (0.20 g, 1.42 mmol) in ACN (2 ml). The free base was converted to HCl salt with 1 M HCl in Et$_2$O yielding 31 mg N-methyl-4-(piperazin-1-yl)-1,2,5-thiadiazole-3-carboxamide hydrochloride.

$^1$H NMR (400 MHz, DMSO-d$_6$): 2.79 (3H, d), 3.22-3.66 (7H, m), 3.72-3.87 (1H, m), 3.99-4.13 (3H, m), 4.30-4.40 (1H, m), 4.91-5.02 (1H, m), 6.82-7.02 (4H, m), 8.70-8.83 (1H, m), 11.50 (1H, br s).

EXAMPLE 30: (S)-1-(4-(4-((2,3-Dihydrobenzo[b][1,4]dioxin-2-yl)methyl)piperazin-1-yl)-1,2,5-thiadiazol-3-yl)imidazolidin-2-one Step 1: tert-Butyl 4-(4-(2-oxoimidazolidin-1-yl)-1,2,5-thiadiazol-3-yl)piperazine-1-carboxylate To a solution of tert-butyl 4-(4-chloro-1,2,5-thiadiazol-3-yl)piperazine-1-carboxylate (3.18 g, 10.4 mmol) and imidazolidin-2-one (1.50 g, 17.4 mmol) in 1,4-dioxane (30 ml) were added CuI (3.32 g, 17.4 mmol), N$^1$,N$^2$-dimethylethane-1,2-diamine (0.54 ml, 0.44 g, 5.22 mmol) and K$_3$PO$_4$ (5.55 g, 26.2 mmol) at RT and heated the reaction mixture to 100° C. for 16 h. The reaction mixture was filtered through Celite pad, washed with EtOAc, filtrate was concentrated and the crude product was purified using flash chromatography yielding 0.30 g tert-butyl 4-(4-(2-oxoimidazolidin-1-yl)-1,2,5-thiadiazol-3-yl)piperazine-1-carboxylate. m/z=355.2 (M+1)$^+$.

Step 2: 1-(4-(Piperazin-1-yl)-1,2,5-thiadiazol-3-yl) imidazolidin-2-one hydrochloride tert-Butyl 4-(4-(2-oxoimidazolidin-1-yl)-1,2, 5-thiadiazol-3-yl)piperazine-1-carboxylate (0.6 g, 1.97 mmol) was added to ice cold 4 M HCl in 1,4-dioxane (10 ml, 40 mmol), allowed to warm to RT and stirred for 2 h. The solvent was evaporated off and the residue was triturated with pentane yielding 0.54 g 1-(4-(piperazin-1-yl)-1,2,5-thiadiazol-3-yl) imidazolidin-2-one hydrochloride. m/z=255.1 (M+1)$^+$.

Step 3: (S)-1-(4-(4-((2,3-Dihydrobenzo[b][1,4]di-oxin-2-yl)methyl)piperazin-1-yl)-1,2,5-thiadiazol-3-yl)imidazolidin-2-one Prepared using general procedure A1 from 1-(4-(piper-azin-1-yl)-1,2,5-thiadiazol-3-yl)imidazolidin-2-one hydrochloride (0.10 g, 0.34 mmol), (R)-2-(bromomethyl)-2,3-dihydrobenzo[b][1,4]dioxine (95 mg, 0.41 mmol), and $K_2CO_3$ (0.12 g, 0.86 mmol) in ACN (2 ml) yielding 13 mg (S)-1-(4-(4-((2,3-Dihydrobenzo[b][1,4]dioxin-2-yl)methyl) piperazin-1-yl)-1,2,5-thiadiazol-3-yl)imidazolidin-2-one.
$^1$H NMR (400 MHz, $CDCl_3$): 2.59-2.79 (6H, m), 3.41-3.51 (4H, m), 3.63 (2H, t), 3.96-4.07 (3H, m), 4.28-4.38 (2H, m), 5.16 (1H, br s), 6.80-6.91 (4H, m).

EXAMPLE 31: (S)-1-(5-(4-((2,3-Dihydrobenzo[b][1,4]dioxin-2-yl)methyl)piperazin-1-yl)-3-methylisothiazol-4-yl)pyrrolidin-2-one

Step 1: (S)-5-(4-((2,3-Dihydrobenzo[b][1,4]dioxin-2-yl)methyl)piperazin-1-yl)-3-methyl-4-nitroisothiazole A mixture of (S)-1-((2,3-dihydrobenzo[b][1,4]dioxin-2-yl)methyl)piperazine dihydrochloride (0.14 g, 0.45 mmol), 5-bromo-3-methyl-4-nitro-1,2-thiazole (0.10 g, 0.45 mmol), and DIPEA (0.25 ml, 0.19 g, 1.44 mmol) in DMF (3 ml) was stirred at RT for 45 min. The mixture was diluted with water and extracted with EtOAc. Combined organic phases were washed with water and brine, dried and evaporated yielding 0.17 g (S)-5-(4-((2,3-dihydrobenzo[b][1,4]dioxin-2-yl) methyl)piperazin-1-yl)-3-methyl-4-nitroisothiazole. m/z=377.2 $(M+1)^+$.

Step 2: (S)-5-(4-((2,3-Dihydrobenzo[b][1,4]dioxin-2-yl)methyl)piperazin-1-yl)-3-methylisothiazol-4-amine Prepared as described in Example 32, Step 3, from (S)-5-(4-((2,3-dihydrobenzo[b][1,4]dioxin-2-yl)methyl)piperazin-1-yl)-3-methyl-4-nitroisothiazole (0.16 g, 0.43 mmol), $NH_4Cl$ (0.23 g, 4.25 mmol), and Zn dust (0.28 g, 4.25 mmol) in THF (3 ml), MeOH (3 ml), and water (1 ml) yielding 0.15 g (S)-5-(4-((2,3-dihydrobenzo[b][1,4]dioxin-2-yl)methyl)piperazin-1-yl)-3-methylisothiazol-4-amine. m/z=347.6 $(M+1)^+$.

Step 3: (S)-1-(5-(4-((2,3-Dihydrobenzo[b][1,4]di-oxin-2-yl)methyl)piperazin-1-yl)-3-methylisothiazol-4-yl)pyrrolidin-2-one A solution of (S)-5-(4-((2,3-dihydrobenzo[b][1,4]dioxin-2-yl)methyl)piperazin-1-yl)-3-methylisothiazol-4-amine (0.15 g, 0.43 mmol) in DCM (4 ml) was treated with 4-chlorobutyryl chloride (53 μl, 67 mg, 0.48 mmol) and TEA (72 μl, 53 mg, 0.52 mmol). The resulting mixture was stirred at RT until the reaction was completed. The mixture was diluted with DCM and washed with 1 M HCl, sat. $NaHCO_3$ solution, water and brine, dried and evaporated. The residue was dissolved in THF (4 ml) and 60% NaH dispersion (52 mg, 1.30 mmol) was added. The resulting mixture was stirred until the intermediate was consumed. Water was added and the mixture was extracted with EtOAc. The combined extracts were washed with water and brine, dried and evaporated. The residue was purified by flash chromatography yielding 0.10 g (S)-1-(5-(4-((2,3-dihyd-robenzo[b][1,4]dioxin-2-yl)methyl)piperazin-1-yl)-3-meth-ylisothiazol-4-yl)pyrrolidin-2-one.
$^1$H NMR (400 MHz, $CDCl_3$): 2.10-2.31 (2H, m), 2.20 (3H, s), 2.41-2.78 (8H, m), 3.10-3.31 (4H, m), 3.40-3.53 (1H, m), 3.67-3.80 (1H, m), 3.97-4.05 (1H, m), 4.25-4.36 (2H, m), 6.80-6.91 (4H, m).

EXAMPLE 32: (S)-1-(4-(4-((2,3-Dihydrobenzo[b][1,4]dioxin-2-yl)methyl)piperazin-1-yl)-2-methylthi-azol-5-yl)-3,3-dimethylpyrrolidine-2,5-dione hydrochloride

Step 1: 4-Bromo-2-methyl-5-nitrothiazole

To a stirred solution of 4-bromo-2-methylthiazole (40.0 g, 168.8 mmol) in conc. $H_2SO_4$ (400 ml) was added conc. $HNO_3$ (100 ml) slowly at 0° C. and then stirred at RT for 3 h. The reaction mixture was poured in ice cold water and extracted with EtOAc. The organic layer was dried and evaporated and the residue purified by flash chromatography yielding 28 g 4-bromo-2-methyl-5-nitrothiazole. m/z=223.0 $(M+1)^+$.

Step 2: tert-Butyl 4-(2-methyl-5-nitrothiazol-4-yl) piperazine-1-carboxylate To a solution of 4-bromo-2-methyl-5-nitrothiazole (30.0 g, 135.1 mmol) in 2-propanol (300 ml) was added tert-butyl piperazine-1-carboxylate (27.7 g, 148.6 mmol) at RT and then stirred at 50° C. for 8 h. The solvent was evaporated and the residue purified by flash chromatography yielding 21.2 g tert-butyl 4-(2-methyl-5-nitrothiazol-4-yl)piperazine-1-carboxylate. m/z=229.1 $(M-Boc+1)^+$.

Step 3: tert-Butyl 4-(5-amino-2-methylthiazol-4-yl) piperazine-1-carboxylate A mixture of tert-butyl 4-(2-methyl-5-nitrothiazol-4-yl) piperazine-1-carboxylate (1.00 g, 3.04 mmol) and $NH_4Cl$ (1.63 g, 30.4 mmol) in THF (15 ml), MeOH (7 ml), and water (7 ml) at 0° C. was treated with Zn dust (1.99 g, 30.4 mmol) and stirred for 5 min 0° C., followed by stirring at RT for 1 h. The reaction mixture was diluted with EtOAc, filtered through a Celite pad, washed with brine, dried and evaporated yielding 0.60 g tert-butyl 4-(5-amino-2-methyl-thiazol-4-yl)piperazine-1-carboxylate. m/z=299.2 $(M+1)^+$.

Step 4: tert-Butyl 4-(5-(3,3-dimethyl-2,5-dioxopyr-rolidin-1-yl)-2-methylthiazol-4-yl)piperazine-1-car-boxylate To a solution of tert-butyl 4-(5-amino-2-methylthiazol-4-yl)piperazine-1-carboxylate (2.8 g, 9.39 mmol) in toluene (60 ml) was added $Et_3N$ (1.96 ml, 1.42 g, 14.1 mmol) and 3,3-dimethyldihydrofuran-2,5-dione (1.44 g, 11.3 mmol) at RT and heated to reflux at 110° C. for 18 h. The reaction mixture was concentrated. The residue was diluted with EtOAc and washed with water. The organic layer was dried evaporated and the residue purified by flash chromatography yielding 0.20 g tert-butyl 4-(5-(3,3-dimethyl-2,5-dioxopyr-rolidin-1-yl)-2-methylthiazol-4-yl)piperazine-1-carboxy-late. m/z=409.2 $(M+1)^+$.

Step 5: 3,3-Dimethyl-1-(2-methyl-4-(piperazin-1-yl) thiazol-5-yl)pyrrolidine-2,5-dione hydrochloride A solution of tert-butyl 4-(5-(3,3-dimethyl-2,5-dioxopyr-rolidin-1-yl)-2-methylthiazol-4-yl)piperazine-1-carboxylate (150 mg, 0.37 mmol) in 4 M HCl in 1,4-dioxane (10 ml, 40 mmol) at 0° C. was stirred at RT for 2 h, evaporated to dryness and the residue triturated with 1:5 pentane:Et$_2$O yielding 125 mg 3,3-dimethyl-1-(2-methyl-4-(piperazin-1-yl)thiazol-5-yl)pyrrolidine-2,5-dione hydrochloride. m/z=309.2 (M+1)$^+$.

Step 6: (S)-1-(4-(4-((2,3-Dihydrobenzo[b][1,4]dioxin-2-yl)methyl)piperazin-1-yl)-2-methylthiazol-5-yl)-3,3-dimethylpyrrolidine-2,5-dione hydrochloride Prepared using general procedure A1 from 3,3-dimethyl-1-(2-methyl-4-(piperazin-1-yl)thiazol-5-yl)pyrrolidine-2,5-dione hydrochloride (60 mg, 0.17 mmol), (R)-2-(bromomethyl)-2,3-dihydrobenzo[b][1,4]dioxine (48 mg, 0.21 mmol), and K$_2$CO$_3$ (60 mg, 0.44 mmol) in ACN (2 ml) yielding 29 mg (S)-1-(4-(4-((2,3-Dihydrobenzo[b][1,4]dioxin-2-yl)methyl)piperazin-1-yl)-2-methylthiazol-5-yl)-3,3-dimethylpyrrolidine-2,5-dione hydrochloride after conversion of free base to HCl salt.
$^1$H NMR (400 MHz, CDCl$_3$): 1.42 (6H, d), 2.61 (3H, s), 2.75 (2H, s), 3.02-3.23 (3H, m), 3.26-3.39 (2H, m), 3.40-3.54 (2H, t), 3.74-3.92 (3H, m), 4.11-4.20 (1H, m), 4.23-4.31 (1H, m), 5.28-5.36 (1H, m), 6.84-6.95 (4H, m), 13.38 (1H, br s).

EXAMPLE 33: (S)-1-(4-(4-((2,3-Dihydrobenzo[b][1,4]dioxin-2-yl)methyl)piperazin-1-yl)-1,2,5-thiadiazol-3-yl)ethanone Step 1: 4-(4-(tert-Butoxycarbonyl)piperazin-1-yl)-1,2,5-thiadiazole-3-carboxylic acid To a solution of methyl 4-(4-(tert-butoxycarbonyl)piperazin-1-yl)-1,2,5-thiadiazole-3-carboxylate (1.20 g, 3.65 mmol, Example 27, Step 1) in THF (25 ml) and water (5 ml) was added LiOH.H$_2$O (0.31 g, 7.32 mmol) portion wise at 0° C. The reaction mixture was allowed to stir at RT for 3 h. The mixture was diluted with water, acidified with citric acid and extracted with EtOAc. The organic layer was dried and evaporated to dryness yielding 1.00 g 4-(4-(tert-butoxycarbonyl)piperazin-1-yl)-1,2,5-thiadiazole-3-carboxylic acid. m/z=313.2 (M−1)$^−$.

Step 2: tert-Butyl 4-(4-(methoxy(methyl)carbamoyl)-1,2,5-thiadiazol-3-yl)piperazine-1-carboxylate To a solution of 4-(4-(tert-butoxycarbonyl)piperazin-1-yl)-1,2,5-thiadiazole-3-carboxylic acid (1.10 g, 3.50 mmol) in DCM (50 ml) was added N,O-dimethylhydroxylamine hydrochloride (0.51 g, 5.25 mmol), DMAP (0.86 g, 7.00 mmol) and EDC-HCl (1.00 g, 5.23 mmol) at 0° C. and the reaction mixture was allowed to stir at RT for 16 h. The mixture was diluted with DCM and washed with water, dried and evaporated to dryness. The residue was purified by flash chromatography yielding 0.80 g tert-butyl 4-(4-(methoxy(methyl)-carbamoyl)-1,2,5-thiadiazol-3-yl)piperazine-1-carboxylate. m/z=358.2 (M+1)$^+$.

Step 3: tert-Butyl 4-(4-acetyl-1,2,5-thiadiazol-3-yl)piperazine-1-carboxylate

To a solution of tert-butyl 4-(4-(methoxy(methyl)carbamoyl)-1,2,5-thiadiazol-3-yl)piperazine-1-carboxylate (0.30 g, 0.84 mmol) in THF (15 ml) was added 1.0 M CH$_3$MgBr in THF (1.2 ml, 1.2 mmol) at 0° C. and the reaction mixture was allowed to stirred at RT for 1 h. The reaction mixture was quenched with NH$_4$Cl solution and extracted with EtOAc. The organic layer was dried and evaporated to dryness. The residue was purified by flash chromatography yielding 0.15 g tert-butyl 4-(4-acetyl-1,2,5-thiadiazol-3-yl)piperazine-1-carboxylate. m/z=313.2 (M+1)$^+$.

Step 4: 1-(4-(Piperazin-1-yl)-1,2,5-thiadiazol-3-yl)ethanone hydrochloride

An ice cold stirred solution of tert-butyl 4-(4-acetyl-1,2,5-thiadiazol-3-yl)piperazine-1-carboxylate (0.15 g, 0.48 mmol) in 4 M HCl in dioxane (20 ml, 80 mmol) was allowed to warm to RT and stir for 3 h. The solvent was evaporated off and the residue was triturated with pentane yielding 0.15 g 1-(4-(piperazin-1-yl)-1,2,5-thiadiazol-3-yl)ethanone hydrochloride. m/z=213.1 (M+1)$^+$.

Step 5: (S)-1-(4-(4-((2,3-Dihydrobenzo[b][1,4]dioxin-2-yl)methyl)piperazin-1-yl)-1,2,5-thiadiazol-3-yl)ethanone hydrochloride Prepared using general procedure A1 from 1-(4-(piperazin-1-yl)-1,2,5-thiadiazol-3-yl)ethanone hydrochloride (80 mg, 0.32 mmol), (R)-2-(bromomethyl)-2,3-dihydrobenzo[b][1,4]dioxine (88 mg, 0.39 mmol), and K$_2$CO$_3$ (0.11 g, 0.80 mmol) in ACN (2 ml) yielding 23 mg (S)-1-(4-(4-((2,3-dihydrobenzo[b][1,4]dioxin-2-yl)methyl)piperazin-1-yl)-1,2,5-thiadiazol-3-yl)ethanone hydrochloride after conversion of free base to HCl salt.
$^1$H NMR (400 MHz, CDCl$_3$): 2.74 (3H, s), 3.20 (3H, m), 3.34-3.66 (2H, m), 3.74-4.40 (7H, m), 5.37 (1H, br s), 6.83-7.00 (4H, m), 13.65 (1H, br s).

EXAMPLE 34: (S)-4-(4-((2,3-Dihydrobenzo[b][1,4]dioxin-2-yl)methyl)piperazin-1-yl)-N,N-dimethyl-1,2,5-thiadiazole-3-carboxamide Step 1: tert-Butyl 4-(4-(dimethylcarbamoyl)-1,2,5-thiadiazol-3-yl)piperazine-1-carboxylate A solution of methyl 4-(4-(tert-butoxycarbonyl)piperazin-1-yl)-1,2,5-thiadiazole-3-carboxylate (0.70 g, 2.13 mmol) in 33% dimethylamine in EtOH (20 ml) was heated in a sealed tube at 90° C. for 16 h. The reaction mixture was concentrated and the residue was purified by flash chromatography yielding 0.35 g tert-butyl 4-(4-(dimethylcarbamoyl)-1,2,5-thiadiazol-3-yl)piperazine-1-carboxylate. m/z=342.2 (M+1)$^+$.

Step 2: N,N-Dimethyl-4-(piperazin-1-yl)-1,2,5-thiadiazole-3-carboxamide hydrochloride Prepared from tert-butyl 4-(4-(dimethylcarbamoyl)-1,2,5-thiadiazol-3-yl)piperazine-1-carboxylate (0.35 g, 1.03 mmol) and 4 M HCl in 1,4-dioxane (20 ml, 80 mmol) as described in Example 8, Step 2 yielding 0.28 g N,N-dimethyl-4-(piperazin-1-yl)-1,2,5-thiadiazole-3-carboxamide hydrochloride. m/z=242.2 (M+1)$^+$.

Step 3: (S)-4-(4-((2,3-Dihydrobenzo[b][1,4]dioxin-2-yl)methyl)piperazin-1-yl)-N,N-dimethyl-1,2,5-thiadiazole-3-carboxamide Prepared using general procedure A1 from N,N-dimethyl-4-(piperazin-1-yl)-1,2,5-thiadiazole-3-carboxamide hydrochloride (0.12 g, 0.43 mmol), (R)-2-(bromomethyl)-2,3-dihydrobenzo[b][1,4]dioxine (0.12 g, 0.52 mmol), and K₂CO₃ (0.15 g, 1.08 mmol) in ACN (2 ml) yielding crude product. After reverse phase preparative HPLC 10 mg (S)-4-(4-((2,3-dihydrobenzo[b][1,4]dioxin-2-yl)methyl)piperazin-1-yl)-N,N-dimethyl-1,2,5-thiadiazole-3-carboxamide was obtained.

$^1$H NMR (400 MHz, CDCl₃): 2.59-2.78 (6H, m), 2.97 (3H, s), 3.15 (3H, s), 3.41-3.54 (4H, m), 3.97-4.07 (1H, m), 4.27-4.38 (2H, m), 6.80-6.93 (4H, m).

EXAMPLE 35: (S)-4-(4-((2,3-Dihydrobenzo[b][1,4]dioxin-2-yl)methyl)piperazin-1-yl)-N-(pyridin-4-yl)-1,2,5-thiadiazol-3-amine dihydrochloride Step 1: tert-Butyl 4-(4-(pyridin-2-ylamino)-1,2,5-thiadiazol-3-yl)piperazine-1-carboxylate To a solution of tert-butyl 4-(4-chloro-1,2,5-thiadiazol-3-yl)piperazine-1-carboxylate (4.00 g, 13.1 mmol) in toluene (100 ml) was added 2-aminopyridine (1.01 g, 15.7 mmol) and NaOtBu (1.89 g, 19.7 mmol) at RT. The mixture was degassed with argon for 30 min and Pd₂(dba)₃ and RuPhos were added. The reaction mixture was heated at 100° C. for 16 h in a sealed tube. After cooling to RT, the mixture was filtered through a Celite pad with EtOAc and evaporated. The crude product was purified by flash chromatography yielding 0.70 g tert-butyl 4-(4-(pyridin-2-ylamino)-1,2,5-thiadiazol-3-yl)piperazine-1-carboxylate. m/z=363.2 (M+1)⁺.

Step 2: 4-(Piperazin-1-yl)-N-(pyridin-4-yl)-1,2,5-thiadiazol-3-amine hydrochloride Prepared from tert-butyl 4-(4-(pyridin-2-ylamino)-1,2,5-thiadiazol-3-yl)piperazine-1-carboxylate (0.40 g, 1.10 mmol) and 4 M HCl in 1,4-dioxane (20 ml, 80 mmol) for 3 h yielding 0.40 g 4-(piperazin-1-yl)-N-(pyridin-4-yl)-1,2,5-thiadiazol-3-amine hydrochloride. m/z=263.2 (M+1)⁺.

Step 3: (S)-4-(4-((2,3-Dihydrobenzo[b][1,4]dioxin-2-yl)methyl)piperazin-1-yl)-N-(pyridin-4-yl)-1,2,5-thiadiazol-3-amine Prepared using general procedure A1 from 4-(piperazin-1-yl)-N-(pyridin-4-yl)-1,2,5-thiadiazol-3-amine hydrochloride (0.12 g, 0.40 mmol), (R)-2-(bromomethyl)-2,3-dihydrobenzo[b][1,4]dioxine (0.11 g, 0.48 mmol), and K₂CO₃ (0.14 g, 1.00 mmol) in ACN (2 ml) yielding 42 mg (S)-4-(4-((2,3-dihydrobenzo[b][1,4]dioxin-2-yl)methyl)piperazin-1-yl)-N-(pyridin-4-yl)-1,2,5-thiadiazol-3-amine.

$^1$H NMR (400 MHz, CDCl₃): 2.64-2.90 (6H, m), 3.22-3.34 (4H, m), 4.00-4.08 (1H, m), 4.29-4.40 (2H, m), 6.80-6.93 (4H, m), 6.94-6.99 (1H, m), 7.51 (1H, br s), 7.69-7.76 (1H, m), 8.22-8.30 (2H, m).

EXAMPLE 36: (S)-3-(4-((2,3-Dihydrobenzo[b][1,4]dioxin-2-yl)methyl)piperazin-1-yl)isothiazolo[4,5-b]pyridine hydrochloride Step 1: 3-Bromoisothiazolo[4,5-b]pyridine To a stirred solution of 3-mercaptopicolinonitrile (1.20 g, 8.81 mmol) in EtOAc (30 ml) was added bromine (1.20 ml, 3.73 g, 20.7 mmol) drop wise at 0° C. Then the reaction mixture was allowed to warm to RT over 1 h and then refluxed for 6 h. The solvent was evaporated off and the residue was purified by flash chromatography yielding 0.30 g 3-bromoisothiazolo[4,5-b]pyridine. m/z=215.0 (M+1)⁺.

Step 2: tert-Butyl 4-(isothiazolo[4,5-b]pyridin-3-yl)piperazine-1-carboxylate

To a stirred solution of 3-bromoisothiazolo[4,5-b]pyridine (0.20 g, 0.93 mmol) in IPA (2 ml) was added tert-butyl piperazine-1-carboxylate (0.17 g, 0.93 mmol) and the resulting mixture was heated to 100° C. for 16 h. The solvent was evaporated off, the residue was dissolved in NaHCO₃ solution and extracted with EtOAc. The combined organic layers were dried and evaporated to dryness. The residue was purified by flash chromatography yielding 0.15 g tert-butyl 4-(isothiazolo[4,5-b]pyridin-3-yl)piperazine-1-carboxylate. m/z=321.1 (M+1)⁺.

Step 3: 3-(Piperazin-1-yl)isothiazolo[4,5-b]pyridine hydrochloride

To an ice cold stirred solution of tert-butyl 4-(isothiazolo[4,5-b]pyridin-3-yl)piperazine-1-carboxylate (0.53 g, 1.65 mmol) in dioxane (4 ml) was added 4 M HCl in dioxane (8 ml, 32 mmol) and the mixture was stirred at RT for 6 h. The solvent was evaporated off and the residue was triturated with 1:1 Et₂O/pentane yielding 0.42 g 3-(piperazin-1-yl)isothiazolo[4,5-b]pyridine hydrochloride. m/z=221.1 (M+1)⁺.

Step 4: (S)-3-(4-((2,3-Dihydrobenzo[b][1,4]dioxin-2-yl)methyl)piperazin-1-yl)isothiazolo[4,5-b]pyridine hydrochloride Prepared using general procedure A1 from 3-(piperazin-1-yl)isothiazolo[4,5-b]pyridine hydrochloride (0.10 g, 0.39 mmol), (R)-2-(bromomethyl)-2,3-dihydrobenzo[b][1,4]dioxine (0.13 g, 0.55 mmol), and K₂CO₃ (0.14 g, 1.00 mmol) in ACN (2 ml) yielding 45 mg (S)-3-(4-((2,3-dihydrobenzo[b][1,4]dioxin-2-yl)methyl)piperazin-1-yl)isothiazolo[4,5-b]pyridine hydrochloride after conversion of free base to HCl salt.

$^1$H NMR (400 MHz, CDCl₃): 2.99-3.27 (3H, m), 3.32-3.44 (1H, m), 3.47-3.63 (1H, m), 3.88-4.14 (3H, m), 4.14-4.23 (1H, m), 4.25-4.34 (1H, m), 5.04-5.32 (2H, m), 5.37 (1H, br s), 6.84-6.93 (4H, m), 7.37-7.42 (1H, m), 8.15-8.20 (1H, m), 8.63-8.68 (1H, m), 13.62 (1H. br s).

EXAMPLE 37: (S)—N-(2-(Benzyloxy)pyridin-3-yl)-4-(4-((2,3-dihydrobenzo[b][1,4]-dioxin-2-yl)methyl)piperazin-1-yl)-1,2,5-thiadiazol-3-amine hydrochloride Step 1: tert-Butyl 4-(4-((2-(benzyloxy)pyridin-3-yl)amino)-1,2,5-thiadiazol-3-yl)piperazine-1-carboxylate To a stirred solution of tert-butyl 4-(4-chloro-1,2,5-thiadiazol-3-yl)piperazine-1-carboxylate (1.00 g, 3.28 mmol) in toluene (20 ml) in a microwave vial was added 2-(benzyloxy)-pyridin-3-amine (0.72 g, 3.61 mmol) followed by NaOtBu (0.63 g, 6.56 mmol) at RT, then the mixture was degassed with Ar for 30 min. Then Pd₂(dba)₃ (0.15 g, 0.16 mmol) and RuPhos (0.15 g, 0.32 mmol) were added at RT and the reaction mixture was heated at 80° C. under microwave irradiation for 2 h. The mixture was filtered through a Celite pad and evaporated to dryness. The residue was purified by flash chromatography yielding 0.32 g tert-butyl 4-(4-((2-(benzyloxy)pyridin-3-yl)amino)-1,2,5-thiadiazol-3-yl)piperazine-1-carboxylate. m/z=469.2 (M+1)+.

Step 2: N-(2-(Benzyloxy)pyridin-3-yl)-4-(piperazin-1-yl)-1,2,5-thiadiazol-3-amine trifluoroacetate To a solution of tert-butyl 4-(4-((2-(benzyloxy)pyridin-3-yl)amino)-1,2,5-thiadiazol-3-yl)piperazine-1-carboxylate (0.70 g, 1.49 mmol) in DCM (10 ml) was added TFA (2 ml) drop wise at 0° C., and the resulting mixture was allowed to stir at RT for 18 h. The mixture was evaporated to dryness and the residue was triturate with pentane yielding 0.60 g N-(2-(benzyloxy)pyridin-3-yl)-4-(piperazin-1-yl)-1,2,5-thiadiazol-3-amine trifluoroacetate. m/z=369.2 (M+1)+.

Step 3: (S)—N-(2-(Benzyloxy)pyridin-3-yl)-4-(4-((2,3-dihydrobenzo[b][1,4]dioxin-2-yl)methyl)piperazin-1-yl)-1,2,5-thiadiazol-3-amine hydrochloride Prepared using general procedure A1 from N-(2-(benzyloxy)pyridin-3-yl)-4-(piperazin-1-yl)-1,2,5-thiadiazol-3-amine trifluoroacetate (0.10 g, 0.21 mmol), (R)-2-(bromomethyl)-2,3-dihydrobenzo[b][1,4]dioxine (75 mg, 0.33 mmol), and $K_2CO_3$ (83 mg, 0.60 mmol) in ACN (2 ml) yielding 61 mg (S)—N-(2-(benzyloxy)pyridin-3-yl)-4-(4-((2,3-dihydrobenzo[b][1,4]dioxin-2-yl)methyl)piperazin-1-yl)-1,2,5-thiadiazol-3-amine hydrochloride after conversion of free base to HCl salt.
$^1$H NMR (400 MHz, CDCl$_3$): 3.05-4.09 (10H, m), 4.10-4.23 (1H, m), 4.25-4.36 (1H, m), 5.22 (2H, s), 5.25-5.44 (1H, br s), 6.32 (1H, t), 6.86-6.94 (4H, m), 6.95-7.00 (1H, m), 7.27-7.40 (5H, m), 8.17 (1H, s), 8.26-8.33 (1H, m), 13.75 (1H, br s).

EXAMPLE 38: (S)-1-((2,3-Dihydrobenzo[b][1,4]dioxin-2-yl)methyl)-4-(3-methyl-1-(pyridin-2-yl)-1H-pyrazol-5-yl)piperazine

Step 1: 3-Methyl-1-(pyridin-2-yl)-1H-pyrazol-5-amine

A flask was charged with 2-hydrazinopyridine (2.0 g, 18.33 mmol) and EtOH (16 mL). Mixture was cooled to 0° C. and 3-aminocrotononitrile (1.505 g, 18.33 mmol) and AcOH (2.1 mL, 36.7 mmol) were added. Reaction was heated to reflux for 3 h. Mixture was cooled to RT and water (20 mL) was added. Mixture was basified using 5 M NaOH. Solids were filtered and washed with water. Product was dried in 30° C. vacuum oven to give 2.92 g of 3-methyl-1-(pyridin-2-yl)-1H-pyrazol-5-amine as yellowish solids. LC-MS (ES+) [M+1]: 175.4.

Step 2: 1-Benzyl-4-(3-methyl-1-(pyridin-2-yl)-1H-pyrazol-5-yl)piperazine

A flask was charged with 3-methyl-1-(pyridin-2-yl)-1H-pyrazol-5-amine (0.5 g, 2.87 mmol), N-benzyl-2-chloro-N-(2-chloroethyl)ethanamine (1.0 g, 4.31 mmol) and dry DMF (10 mL) under nitrogen. Mixture was cooled with cold water bath and 60% NaH in mineral oil (0.459 g, 11.48 mmol) was added, then allowed to warm to RT. Reaction was heated to 50° C. for 2 h, then heated to 60° C. for 2 h. Mixture was cooled to RT, then water (50 mL) and EtOAc (50 mL) were added. Phases were separated and aqueous phase was extracted with EtOAc (50 mL). Combined organic phases were dried with anhydrous $Na_2SO_4$ and evaporated to dry. Crude product was purified with silica gel chromatography using 0-3% MeOH/EtOAc to give 0.407 g of 1-benzyl-4-(3-methyl-1-(pyridin-2-yl)-1H-pyrazol-5-yl)piperazine as yellow oil. LC-MS (ES+) [M+1]: 334.6.

Step 3: 1-(3-Methyl-1-(pyridin-2-yl)-1H-pyrazol-5-yl)piperazine

A flask was charged with 1-benzyl-4-(3-methyl-1-(pyridin-2-yl)-1H-pyrazol-5-yl)piperazine (0.472 g, 1.42 mmol) and EtOH (10 mL) under nitrogen. Mixture was cooled with cold water bath and conc. HCl (0.349 ml, 4.25 mmol) was added. Air atmosphere was removed with nitrogen flow and 10% Pd/C (0.151 g, 0.142 mmol) was added followed by formic acid (0.534 ml, 14.16 mmol). Mixture was heated to 50° C. under nitrogen atmosphere for 1 h, then heated to 70° C. for 2 h. Another batch of 10% Pd/C (0.151 g, 0.142 mmol) followed by ammonium formate (0.893 g, 14.16 mmol) were added. Then mixture was heated at 70° C. under nitrogen for 3 h. Reaction mixture was cooled to RT and filtered through celite followed by EtOH washings. Filtrate was basified by addition of 50% NaOH until pH is 10-11 and then water (10 mL) was added to redissolved formed solids. Mixture was stirred for 1 h and most of the solvents were evaporated. Residual aqueous phase was extracted with 20% IPA/EtOAc (3×20 mL). Combined organic extracts were dried with anhydrous $Na_2SO_4$ and evaporated to dry to give 0.266 g of 1-(3-methyl-1-(pyridin-2-yl)-1H-pyrazol-5-yl)piperazine as solids. Product was used as such in the next step. LC-MS (ES+) [M+1]: 244.5.

Step 4: (S)-1-((2,3-Dihydrobenzo[b][1,4]dioxin-2-yl)methyl)-4-(3-methyl-1-(pyridin-2-yl)-1H-pyrazol-5-yl)piperazine A flask was charged with 1-(3-methyl-1-(pyridin-2-yl)-1H-pyrazol-5-yl)piperazine (0.250 g, 1.03 mmol), (R)-2-(bromomethyl)-2,3-dihydrobenzo[b][1,4]dioxine (0.259 g, 1.13 mmol), $Na_2CO_3$ (0.163 g, 1.54 mmol) and DMF (5 mL). Mixture was heated to 110-120° C. for 2 h. Reaction was cooled to RT, then EtOAc (20 mL) and water (20 mL) were added. Aqueous phase was extracted with EtOAc (20 mL). Combined organic phases were washed with brine (20 mL), dried with anhydrous $Na_2SO_4$ and evaporated to dry. Crude product was purified with reverse phase chromatography (C18) using 10-100% MeCN/0.5% $HCO_2H$ solution followed by another purification (C18) with 10-100% MeCN/0.1% $NH_4OH$ solution to give 0.194 g of (S)-1-((2,3-dihydrobenzo[b][1,4]dioxin-2-yl)methyl)-4-(3-methyl-1-(pyridin-2-yl)-1H-pyrazol-5-yl)piperazine as white powder.
$^1$H NMR (400 MHz, CDCl$_3$) δ ppm 2.29 (3H, s), 2.56-2.66 (3H, m), 2.66-2.79 (3H, m), 2.91-3.05 (4H, m), 4.00 (1H, dd), 4.23-4.36 (2H, m), 5.70 (1H, s), 6.77-6.93 (4H, m), 7.17 (1H, ddd), 7.76 (1H, ddd), 7.85 (1H, dt), 8.54 (1H, ddd).

EXAMPLE 39: (S)-1-((2,3-Dihydrobenzo[b][1,4]dioxin-2-yl)methyl)-4-(1-(6-methoxypyridin-2-yl)-3-methyl-1H-pyrazol-5-yl)piperazine

Step 1: 1-(6-Methoxypyridin-2-yl)-3-methyl-1H-pyrazol-5-amine

A flask was charged with 2-hydrazinyl-6-methoxypyridine (1.1 g, 7.90 mmol, prepared according to *Biorg. Med. Chem. Lett.* 2011, 21, 2316-2319), 3-aminocrotononitrile (0.649 g, 7.90 mmol) and MeOH (14 mL). To this was added AcOH (2 mL) and reaction was heated to reflux for 3 h.

Mixture was cooled to RT and evaporated to near dry. Residue was partitioned between sat. NaHCO$_3$ solution (20 mL) and EtOAc (20 mL). Aqueous phase was extracted with EtOAc (10 mL). Combined organic phases were washed with brine (20 mL), dried with anhydrous Na$_2$SO$_4$ end evaporated to dry to give 1.525 g of 1-(6-methoxypyridin-2-yl)-3-methyl-1H-pyrazol-5-amine as solids. Product was used as such in the next step. LC-MS (ES+) [M+1]: 205.5.

Step 2: 1-Benzyl-4-(1-(6-methoxypyridin-2-yl)-3-methyl-1H-pyrazol-5-yl)piperazine A flask was charged with 1-(6-methoxypyridin-2-yl)-3-methyl-1H-pyrazol-5-amine (0.486 g, 2.38 mmol), N-benzyl-2-chloro-N-(2-chloroethyl)ethanamine (0.884 g, 3.81 mmol) and dry DMF (10 mL) under nitrogen. Mixture was cooled with cold water bath and 60% NaH in mineral oil (0.381 g, 9.52 mmol) was added, then allowed to warm to RT. Reaction was heated to 60° C. for 2 h, then heated to 80° C. for 1.5 h. Mixture was cooled to RT, then water (30 mL) and EtOAc (30 mL) were added. Aqueous phase was extracted with EtOAc (50 mL). Combined organic phases were washed with brine (50 mL), dried with anhydrous Na$_2$SO$_4$ and evaporated to dry. Crude product was purified with silica gel chromatography using 10-100% EtOAc/heptanes to give 0.380 g of 1-benzyl-4-(1-(6-methoxypyridin-2-yl)-3-methyl-1H-pyrazol-5-yl)piperazine as yellow oil. LC-MS (ES+) [M+1]: 364.1.

Step 3: 1-(1-(6-Methoxypyridin-2-yl)-3-methyl-1H-pyrazol-5-yl)piperazine

A flask was charged with 1-benzyl-4-(1-(6-methoxypyridin-2-yl)-3-methyl-1H-pyrazol-5-yl)piperazine (0.370 g, 1.02 mmol), ammonium formate (0.642 g, 10.18 mmol), formic acid (0.384 ml, 10.18 mmol) and EtOH (8 mL) under nitrogen. To this was added 10% Pd/C (0.108 g, 0.102 mmol) and reaction was heated to 70° C. under nitrogen atmosphere for 1 h. Mixture was cooled to RT, flushed with nitrogen and filter through celite followed by EtOH (10 mL) washings. Filtrate was evaporated to dry. Residue was diluted with sat. aq. Na$_2$CO$_3$ solution (10 mL) and extract with EtOAc (2×20 mL). Combined organic phases were dried with anhydrous Na$_2$SO$_4$ and evaporated to dry to give 0.270 g of 1-(1-(6-methoxypyridin-2-yl)-3-methyl-1H-pyrazol-5-yl)piperazine as yellow oil. Product was used as such in the next step. LC-MS (ES+) [M+1]: 274.4.

Step 4: (S)-1-((2,3-Dihydrobenzo[b][1,4]dioxin-2-yl)methyl)-4-(1-(6-methoxypyridin-2-yl)-3-methyl-1H-pyrazol-5-yl)piperazine A flask was charged with 1-(1-(6-methoxypyridin-2-yl)-3-methyl-1H-pyrazol-5-yl)piperazine (0.244 g, 0.89 mmol), (R)-2-(bromomethyl)-2,3-dihydrobenzo[b][1,4]dioxine (0.259 g, 1.13 mmol), Na$_2$CO$_3$ (0.142 g, 1.34 mmol) and DMF (5 mL). Reaction was heated to 110-120° C. for 3 h. Mixture was cooled to RT and 1 M HCl (15 mL) was added. This mixture was washed with MTBE (2×10 mL). MTBE phase was backextrated with 1 M HCl (5 mL) and org. phase was discarded. Aq. phases were basified with Na$_2$CO$_3$ and the extracted with EtOAc (2×20 mL). Combined organic phases were washed with brine (20 mL), dried with anhydrous Na$_2$SO$_4$ and evaporated to dry. Crude product was purified with reverse phase chromatography (C18) using 10-100% MeCN/0.1% NH$_4$OH solution to give 0.234 g of (S)-1-((2,3-dihydrobenzo[b][1,4]dioxin-2-yl)methyl)-4-(1-(6-methoxypyridin-2-yl)-3-methyl-1H-pyrazol-5-yl)piperazine as white solids.

$^1$H NMR (400 MHz, CDCl$_3$) δ ppm 2.28 (3H, s), 2.51-2.77 (6H, m), 2.93-3.07 (4H, m), 3.94-4.06 (4H, m), 4.23-4.36 (2H, m), 5.67 (1H, s), 6.65 (1H, d), 6.77-6.93 (4H, m), 7.28 (1H, d), 7.64 (1H, t).

EXAMPLE 40: (S)-1-((2,3-Dihydrobenzo[b][1,4]dioxin-2-yl)methyl)-4-(3-methyl-1-(6-methylpyridin-2-yl)-1H-pyrazol-5-yl)piperazine Step 1: 2-Hydrazinyl-6-methylpyridine, hydrochloride A microwave vessel was charged with 6-chloro-2-picoline (1.71 mL, 15.68 mmol) and hydrazine hydrate (9.76 mL, 157 mmol). Mixture was heated to 160° C. for 3 h. Reaction was allowed to cool to RT and then cooled with ice bath. White crystals were filtered and dried in high vacuum to give 1.05 g of 2-hydrazinyl-6-methylpyridine, hydrochloride as white crystals. LC-MS (ES+) [M+1]: 124.2.

Step 2: 3-Methyl-1-(6-methylpyridin-2-yl)-1H-pyrazol-5-amine

A flask was charged with 2-hydrazinyl-6-methylpyridine, HCl (0.85 g, 5.33 mmol), 3-aminocrotononitrile (0.437 g, 5.33 mmol) and EtOH (6 mL). To this was added AcOH (0.61 mL) and reaction was heated to reflux for 5.5 h. Mixture was cooled to RT, some of the solvents were evaporated and then residue was diluted with water (40 mL). Mixture was basified by addition 5 M NaOH and mixed for a while. Solids were filtered and washed with water. Product was dried in 30° C. vacuum oven to give 0.90 g of 3-methyl-1-(6-methylpyridin-2-yl)-1H-pyrazol-5-amine as brownish solids. LC-MS (ES+) [M+1]: 189.3.

Step 3: 1-Benzyl-4-(3-methyl-1-(6-methylpyridin-2-yl)-1H-pyrazol-5-yl)piperazine A flask was charged with 3-methyl-1-(6-methylpyridin-2-yl)-1H-pyrazol-5-amine (0.875 g, 4.65 mmol), N-benzyl-2-chloro-N-(2-chloroethyl)ethanamine (1.619 g, 6.97 mmol) and dry DMF (15 mL) under nitrogen. Reaction was cooled with cold water bath and 60% NaH in mineral oil (0.744 g, 18.59 mmol) was added, then allowed to warm to RT. Reaction was heated to 60° C. for 3 h. Mixture was cooled to RT, then water (60 mL) and EtOAc (60 mL) were added. Aqueous phase was extracted with EtOAc (60 mL). Combined organic phases were washed with brine (60 mL), dried with anhydrous Na$_2$SO$_4$ and evaporated to dry. Crude product was purified with silica gel chromatography using 30-100% EtOAc/heptanes to give 0.795 g of 1-benzyl-4-(3-methyl-1-(6-methylpyridin-2-yl)-1H-pyrazol-5-yl)piperazine as yellow oil. LC-MS (ES+) [M+1]: 348.6.

Step 4: 1-(3-Methyl-1-(6-methylpyridin-2-yl)-1H-pyrazol-5-yl)piperazine

A flask was charged with 1-benzyl-4-(3-methyl-1-(6-methylpyridin-2-yl)-1H-pyrazol-5-yl)piperazine (0.685 g, 1.971 mmol), ammonium formate (1.243 g, 19.71 mmol), formic acid (0.74 ml, 19.71 mmol) and EtOH (10 mL) under nitrogen. To this was added 10% Pd/C (0.210 g, 0.197 mmol) and reaction was heated to 70° C. under nitrogen atmosphere for 1 h. Mixture was cooled to RT, flushed with nitrogen and filter through celite followed by EtOH (2×10 mL) washings. Filtrate was evaporated to dry. Residue was diluted with sat. aq. Na$_2$CO$_3$ solution (10 mL) and extract with EtOAc (2×20 mL). Combined organic phases were dried with anhydrous Na$_2$SO$_4$ and evaporated to dry to give 0.524 g of 1-(3-methyl-1-(6-methylpyridin-2-yl)-1H-pyrazol-5-yl)piperazine as yellow oil. Product was used as such in the next step. LC-MS (ES+) [M+1]: 258.5.

Step 5: (S)-1-((2,3-Dihydrobenzo[b][1,4]dioxin-2-yl)methyl)-4-(3-methyl-1-(6-methylpyridin-2-yl)-1H-pyrazol-5-yl)piperazine A flask was charged 1-(3-methyl-1-(6-methylpyridin-2-yl)-1H-pyrazol-5-yl)piperazine (0.514 g, 1.997 mmol), (R)-2-(bromomethyl)-2,3-dihydrobenzo[b][1,4]dioxine (0.503 g, 2.00 mmol), Na$_2$CO$_3$ (0.318 g, 3.00 mmol) and DMF (10 mL). Reaction was heated to 110-120° C. for 4 h. Mixture was cooled to RT and 1 M HCl (30 mL) was added. Mixture was washed with MTBE (2×15 mL). MTBE phase was back extracted with 1 M HCl (10 mL) and org. phase was discarded. Aq. phases were basified with Na$_2$CO$_3$ and the extracted with EtOAc (2×30 mL). Combined organic phases were washed with brine (20 mL), dried with anhydrous Na$_2$SO$_4$ and evaporated to dry. Crude product was purified with reverse phase chromatography (C18) using 10-100% MeCN/0.1% NH$_4$OH solution to give 0.234 g of (S)-1-((2,3-dihydrobenzo[b][1,4]dioxin-2-yl)methyl)-4-(3-methyl-1-(6-methylpyridin-2-yl)-1H-pyrazol-5-yl)piperazine as semi-solid.

$^1$H NMR (400 MHz, CDCl$_3$) δ ppm 2.28 (3H, s), 2.60 (3H, s), 2.57-2.77 (6H, m), 2.93-3.03 (4H, m), 4.00 (1H, dd), 4.25-4.34 (2H, m), 5.29 (1H, s), 5.68 (1H, s), 6.78-6.91 (4H, m), 7.00-7.06 (1H, m), 7.58-7.69 (2H, m).

As already mentioned hereinbefore, the compounds of formula I show interesting pharmacological properties, namely they exhibit an improved selectivity for the alpha2C adrenoceptor subtype and/or an enhanced potency. Said properties are demonstrated with the pharmacological test presented below.

EXPERIMENT 1: Determination of alpha2A and alpha2C Antagonistic Activity In Vitro Chinese hamster ovary (CHO) cells stably transfected with human alpha2A or alpha2C receptors (University of Turku, Finland) were cotransfected with the expression vector pCEP-Gα16 (Molecular Devices, CA, USA) were used in this experiment. The cells were maintained at 37° C. in a 5% CO$_2$/95% air atmosphere. The cells were cultured in HAM F-12 medium supplemented with 10% FCS, 25 mM HEPES, 100 IU/ml penicillin, 100 g/ml streptomycin, 500 µg/ml geneticin and 240 µg/ml hygromycin B. The cells were subcultured twice weekly with 0.25% trypsin and 1 mM EDTA. The subculture ratio was 1:5-1:20. The growth medium was changed every 2 or 3 days. All cell culture reagents were from Gibco. The day before the experiment the cells were plated into black-walled, clear bottom 384-well plates at a density of 10,000 cells/well.

The growth medium was removed and the cells were incubated with the test compounds and the FLIPR Calcium 6 Assay reagent (Molecular Devices, CA, USA) for 2 h at 37° C. in dark. The test compounds (concentrations in cells 100 pM-10 µM) were dissolved in Probenecid-Ringer consisting of 150 mM NaCl, 3 mM KCl, 1.2 mM MgCl$_2$, 1 mM CaCl$_2$, 5 mM glucose, 20 mM HEPES and 2.5 mM probenecid (pH 7.4 adjusted with 1.0 M NaOH). The osmolarity was adjusted to 322 milliosmoles with Osmostat® OM-6020 osmometer (DIC Kyoto Daiichi Kagagu Co. Ltd, Japan). The changes in intracellular calcium were monitored using FLIPR Tetra high throughput cellular screening system (Molecular Devices, CA, USA) and displayed using ScreenWorks version 4.0 software. All experiments were performed at 37° C. For agonism measurements the test compounds dissolved in Probenecid-Ringer were applied by FLIPR Tetra at 15 s time point. In order to determine antagonism, the cells were stimulated either with 100 nM adrenaline or noradrenaline and the test compounds were added to the cells 2 h before the experiment with the FLIPR Calcium 6 Assay reagent. The IC$_{50}$ value for a given test compound was determined from dose-response curves, which ranged from 0.01 nM to 10 µM. Typically, there were four replicates at each concentration and six different dose levels. For example, if the number of plates from which results were obtained was three, 72 (4*6*3) wells were thus measured to construct dose-response relationship. The samples were excited at 485 nm and emission was detected at 525 nm with a 515 nm cut-off filter. The minimum fluorescence value subtracted from the maximum value for each well was used in the calculations. ScreenWorks version 4.0 software was used for analyzing the results. Fitting of the antagonist dose-response results was performed with the free Hill equation and the IC$_{50}$ values were fitted with IDBS XE software using model 200: y=(A+(B/(1+((x/C)^D)))), where A is the curve maximum, B the curve minimum and C equals the EC50 value. D is slope factor (Hill). Kb was calculated with the Cheng-Prusoff equation Kb=A/((B/C)+1), where A is the IC$_{50}$ of antagonist, B the concentration of agonist and C the EC$_{50}$ of the agonist. The results are shown in Table 1.

TABLE 1

Alpha2A and alpha2C antagonistic activity in vitro.

| Compound | Alpha 2A Adrenaline | | Alpha 2C Adrenaline | |
| --- | --- | --- | --- | --- |
| | IC50 (nM) | Kb (nM) | IC50 (nM) | Kb (nM) |
| Compound of example 1 | 4.670 | 0.210 | <0.010 | <0.100 |
| Compound of example 2 | <0.1 | <0.004 | <0.010 | <0.100 |
| Compound of example 3 | >10000 | >449 | 91.880 | 912.280 |
| Compound of example 4 | 10 | 217 | 0.010 | 0.130 |
| Compound of example 5 | 4594 | 206 | 0.100 | 1.000 |
| Compound of example 6 | 14.055 | 0.630 | <0.010 | <0.100 |
| Compound of example 7 | 10.835 | 0.485 | <0.010 | <0.100 |
| Compound of example 8 | 1966 | 88 | <0.010 | <0.100 |
| Compound of example 9 | >10000 | >449 | 0.060 | 0.550 |
| Compound of example 10 | 7806 | 350 | 0.113 | 1.137 |
| Compound of example 11 | 6808 | 306 | 0.165 | 1.620 |

TABLE 1-continued

Alpha2A and alpha2C antagonistic activity in vitro.

| Compound | Alpha 2A Adrenaline | | Alpha 2C Adrenaline | |
|---|---|---|---|---|
| | IC50 (nM) | Kb (nM) | IC50 (nM) | Kb (nM) |
| Compound of example 12 | 2678 | 120 | 0.210 | 2.130 |
| Compound of example 13 | 960 | 43 | 0.300 | 2.930 |
| Compound of example 14 | 8521 | 382 | 0.030 | 0.290 |
| Compound of example 15 | >10000 | >449 | 0.170 | 1.640 |
| Compound of example 16 | >10000 | >449 | 424.010 | 4209.860 |
| Compound of example 17 | >10000 | >449 | <0.010 | <0.100 |
| Compound of example 18 | 5192 | 233 | 3.030 | 30.070 |
| Compound of example 19 | 10224 | 459 | <0.010 | <0.100 |
| Compound of example 20 | 9024 | 405 | 0.040 | 0.394 |
| Compound of example 21 | >10000 | >449 | 0.040 | 0.380 |
| Compound of example 22 | >10000 | >449 | 158.240 | 1571.100 |
| Compound of example 23 | >10000 | >449 | 136.150 | 1351.740 |
| Compound of example 24 | 8573 | 385 | 0.055 | 0.546 |
| Compound of example 25 | 11454 | 514 | 2.860 | 28.410 |
| Compound of example 26 | >10000 | >449 | 18.470 | 183.380 |
| Compound of example 27 | >10000 | >449 | 165.690 | 1645.090 |
| Compound of example 28 | >10000 | >449 | 108.090 | 1073.170 |
| Compound of example 29 | >10000 | >449 | 423.860 | 4208.300 |
| Compound of example 30 | >10000 | >449 | 0.054 | 0.527 |
| Compound of example 31 | >10000 | >449 | 0.170 | 1.660 |
| Compound of example 32 | 0.520 | 0.020 | <0.010 | <0.100 |
| Compound of example 33 | >10000 | >449 | 40.380 | 400.940 |
| Compound of example 34 | >10000 | >449 | 0.090 | 0.920 |
| Compound of example 35 | 6128 | 275 | 10.045 | 99.710 |
| Compound of example 36 | 6647 | 298 | 13.554 | 134.554 |
| Compound of example 37 | >10000 | >449 | 7.360 | 73.120 |
| Compound of example 38 | 3323 | 149 | 0.230 | 2.280 |
| Compound of example 39 | 1830 | 82 | 0.030 | 0.290 |
| Compound of example 40 | 2232 | 100 | 0.260 | 2.570 |

In vivo effects of the compounds of formula I can be demonstrated with the pharmacological tests as described in WO 03/082866.

The compounds of formula I exhibit alpha2C antagonistic activity. The present disclosure thus provides compounds for use as a medicament. Compounds for use in the treatment of disorder, condition, or disease where an alpha2C antagonist is indicated to be useful are also provided. Furthermore, a method for the treatment of disorder, condition, or disease where an alpha2C antagonist is indicated to be useful is provided. In said method an effective amount of at least one compound of formula I is administered to a mammal, such as human, in need of such treatment. The use of the compounds of formula I for the manufacture of a medicament for the treatment of disorder, condition, or disease where an alpha2C antagonist is indicated to be useful is also provided.

In one embodiment of the invention the aforementioned disorder, condition or disease where an alpha2C antagonist is indicated to be useful is a mental disorder propagated by stress, Parkinson's disease, depression, schizophrenia, attention deficit hyperactivity disorder, post-traumatic stress disorder, obsessive compulsive disorder, Tourette's syndrome, blepharospasm or other focal dystonias, temporal lobe epilepsy with psychosis, a drug-induced psychosis, Huntington's disease, a disorder caused by fluctuation of the levels of sex hormones, panic disorder, Alzheimer's disease or mild cognitive impairment; for example, a mental disorder propagated by stress, Parkinson's disease, depression, schizophrenia, attention deficit hyperactivity disorder, obsessive compulsive disorder or Alzheimer's disease; such as a mental disorder propagated by stress, depression or schizophrenia.

Representative examples of drug-induced psychoses include, but are not limited to, psychosis caused by chronic use of dopaminergic agents.

Representative examples of disorders caused by fluctuation of the levels of sex hormones include, but are not limited to, premenstrual syndrome and hot flashes.

The compounds of the present disclosure can be administered, for example, enterally, topically or parenterally by means of any pharmaceutical formulation useful for said administration and comprising at least one active compound of formula I in pharmaceutically acceptable and effective amounts together with pharmaceutically acceptable diluents, carriers and/or excipients known in the art. The manufacture of such pharmaceutical formulations is known in the art.

The therapeutic dose to be given to a subject in need of the treatment will vary depending on the compound being administered, the species, the age and the sex of the subject being treated, the particular condition being treated, as well as the route and method of administration, and is easily determined by a person skilled in the art. Accordingly, the typical dosage for oral administration is from 10 ng/kg to 100 mg/kg per day and for parenteral administration from 1 ng/kg to 10 mg/kg for an adult mammal.

The compounds of the present disclosure are given to the subject as such or in combination with one or more other active ingredients, each in its own composition or some or all of the active ingredients combined in a single composition, and/or suitable pharmaceutical excipients. Suitable pharmaceutical excipients include conventionally used excipients and formulation aids, such as fillers, binders, disintegrating agents, lubricants, solvents, gel forming agents, emulsifiers, stabilizers, colorants and/or preservatives.

The compounds of the present disclosure are formulated into dosage forms using commonly known pharmaceutical manufacturing methods. The dosage forms can be, for example, tablets, capsules, granules, suppositories, emulsions, suspensions or solutions. Depending on the route of administration and the galenic form, the amount of the active ingredient in a formulation can typically vary between 0.01% and 100% by weight.

A person skilled in the art will appreciate that the embodiments described herein can be modified without departing from the inventive concept. A person skilled in the art also understands that the present disclosure is not limited to the particular embodiments disclosed but is intended to also cover modifications of the embodiments that are within the scope of the present disclosure.

The invention claimed is:

1. A compound of formula I,

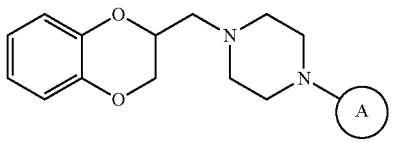

I wherein
ring A is a five membered unsaturated heterocyclic ring containing 1, 2, or 3 ring heteroatom(s) each independently selected from N, O, and S, wherein said heterocyclic ring is unsubstituted, or said heterocyclic ring is substituted with 1 substituent $R_1$, or said heterocyclic ring is substituted with 2 substituents $R_1$ and $R_2$, or said heterocyclic ring is substituted with 3 substituents $R_1$, $R_2$, and $R_3$, or said heterocyclic ring is substituted with 4 substituents $R_1$, $R_2$, $R_3$, and $R_4$;
$R_1$ is $(C_1-C_6)$alkyl, $(C_1-C_6)$alkoxy, hydroxy$(C_1-C_6)$alkyl, $(C_1-C_6)$alkoxy$(C_1-C_6)$alkyl, $(C_1-C_6)$alkoxy-$(C=O)$—, CN, $(C_1-C_6)$alkyl-$(C=O)$—, $R_5R_6N$—, $R_5R_6N$—$(C=O)$—, $R_6(C=O)$—$R_5N$—, heterocyclyl, or heterocyclyl-NH—, wherein said heterocyclyl is optionally substituted with 1, 2, 3, or 4 substituent(s) each independently being $(C_1-C_6)$alkyl, $(C_1-C_6)$alkoxy, oxo, or phenyl$(C_1-C_6)$alkoxy;
$R_2$ is $(C_1-C_6)$alkyl, $(C_1-C_6)$alkoxy, or $(C_1-C_6)$alkoxy$(C_1-C_6)$alkyl;
$R_3$ is $(C_1-C_6)$alkyl, $(C_1-C_6)$alkoxy, or $(C_1-C_6)$alkoxy$(C_1-C_6)$alkyl;
$R_4$ is $(C_1-C_6)$alkyl;
$R_5$ is H, or $(C_1-C_6)$alkyl; and
$R_6$ is H, or $(C_1-C_6)$alkyl;
or $R_1$ and $R_2$ form, together with the ring atoms to which they are attached, a condensed 6 membered unsaturated heterocyclic ring, containing 1 or 2 heteroatom(s) being N;
or a pharmaceutically acceptable salt or ester thereof;
with the proviso that A is not an unsubstituted 1,2,3-oxadiazol-3-ium-3-yl or a 1,2,3-oxadiazol-3-ium-3-yl substituted with 1 substituent $R_1$, 2 substituents $R_1$ and $R_2$, 3 substituents $R_1$, $R_2$, and $R_3$, or 4 substituents $R_1$, $R_2$, $R_3$, and $R_4$.

2. The compound according to claim 1, wherein the compound is a compound of formula Ia,

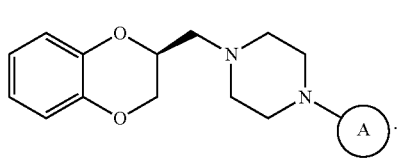

Iª

3. The compound according to claim 1, wherein ring A is selected from the following groups wherein an asterisk denotes the point of attachment to the parent molecular moiety

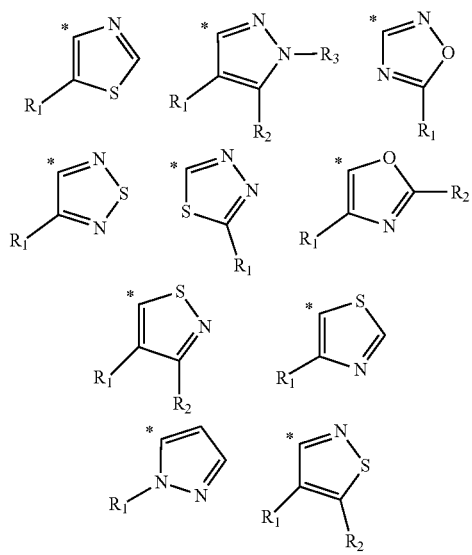

$R_1$ is hydroxy$(C_1-C_6)$alkyl, $(C_1-C_6)$alkoxy$(C_1-C_6)$alkyl, $(C_1-C_6)$alkoxy-$(C=O)$—, CN, $(C_1-C_6)$alkyl-$(C=O)$—, $R_5R_6N$—$(C=O)$—, $R_6(C=O)$—$R_5N$—, or selected from the following groups wherein an asterisk denotes the point of attachment to the parent molecular moiety (1')

(2')

(3')

(4')

(5')

-continued (6')
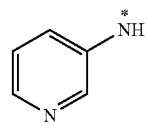

(7')
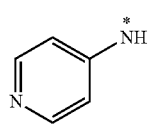

(8')
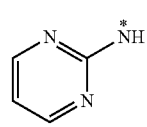

(9')
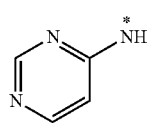

(10')
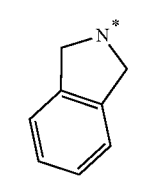

wherein group (1'), (2'), (3'), (4'), (5'), (6'), (7'), (8'), (9'), or (10'), is optionally substituted with 1, 2, 3, or 4 substituent(s) each independently being $(C_1-C_6)$alkyl, $(C_1-C_6)$alkoxy, oxo, or phenyl$(C_1-C_6)$alkoxy;

$R_2$ is $(C_1-C_6)$alkyl;

$R_3$ is $(C_1-C_6)$alkyl;

$R_5$ is H, or $(C_1-C_6)$alkyl; and $R_6$ is H, or $(C_1-C_6)$alkyl;

or $R_1$ and $R_2$ form, together with the ring atoms to which they are attached, a condensed 6 membered unsaturated heterocyclic ring, containing 1 heteroatom being N.

4. The compound according to claim 1, wherein $R_1$ is $(C_1-C_6)$alkyl, $(C_1-C_6)$alkoxy, hydroxy$(C_1-C_6)$alkyl, $(C_1-C_6)$alkoxy$(C_1-C_6)$alkyl, $(C_1-C_6)$alkoxy-(C=O)—, CN, $(C_1-C_6)$alkyl-(C=O)—, $R_5R_6N$—, $R_5R_6N$—(C=O)—, $R_6$(C=O)—$R_5N$—, or selected from the following groups wherein an asterisk denotes the point of attachment to the parent molecular moiety (1')

(2')

(3')
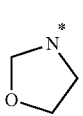

-continued (4')
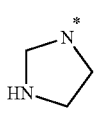

(5')
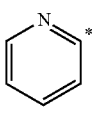

(6')
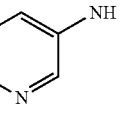

(7')
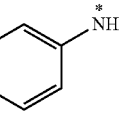

(8')
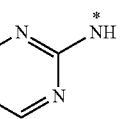

(9')
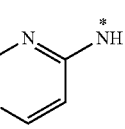

(10')
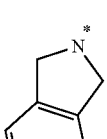

(11')
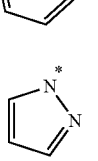

wherein group (1'), (2'), (3'), (4'), (5'), (6'), (7'), (8'), (9'), (10'), or (11') is optionally substituted with 1, 2, 3, or 4 substituent(s) each independently being $(C_1-C_6)$alkyl, $(C_1-C_6)$alkoxy, oxo, or phenyl$(C_1-C_6)$alkoxy.

5. The compound according to claim 1, wherein ring A is selected from the following groups wherein an asterisk denotes the point of attachment to the parent molecular moiety (1)
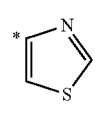

(3)

-continued

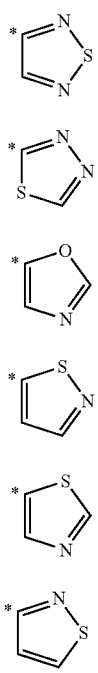

(4)

(5)

(6)

(7)

(8)

(10)

wherein group (1), (3), (4), (5), (6), (7), (8), or (10) is unsubstituted, or group (1), (3), (4), (5), (6), (7), (8), or (10) is substituted with 1 substituent $R_1$, or group (1), (3), (4), (5), (6), (7), (8), or (10) is substituted with 2 substituents $R_1$ and $R_2$, or group (1), (3), (4), (5), (6), (7), (8), or (10) is substituted with 3 substituents $R_1$, $R_2$, and $R_3$;

$R_1$ is hydroxy($C_1$-$C_6$)alkyl, ($C_1$-$C_6$)alkoxy($C_1$-$C_6$)alkyl, ($C_1$-$C_6$)alkoxy-(C=O)—, CN, ($C_1$-$C_6$)alkyl-(C=O)—, $R_5R_6$N—(C=O)—, $R_6$(C=O)—$R_5$N—, or selected from the following groups wherein an asterisk denotes the point of attachment to the parent molecular moiety

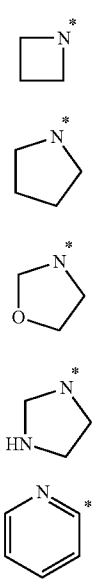

(1')

(2')

(3')

(4')

(5')

-continued

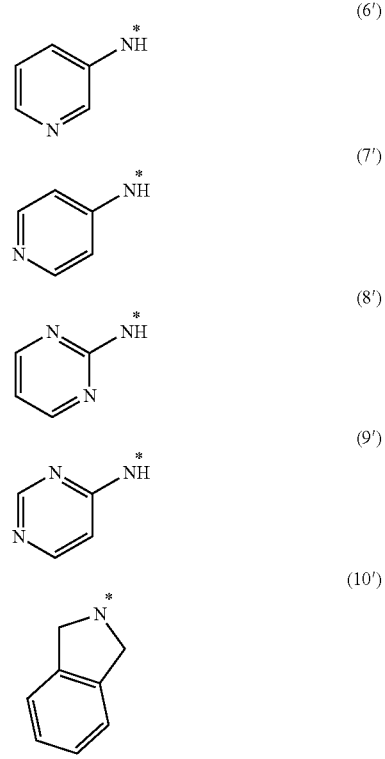

(6')

(7')

(8')

(9')

(10')

wherein group (1'), (2'), (3'), (4'), (5'), (6'), (7'), (8'), (9'), or (10'), is optionally substituted with 1, 2, 3, or 4 substituent(s) each independently being ($C_1$-$C_6$)alkyl, ($C_1$-$C_6$)alkoxy, oxo, or phenyl($C_1$-$C_6$)alkoxy;

$R_2$ is ($C_1$-$C_6$)alkyl;
$R_3$ is ($C_1$-$C_6$)alkyl;
$R_5$ is H, or ($C_1$-$C_6$)alkyl; and
$R_6$ is H, or ($C_1$-$C_6$)alkyl;
or $R_1$ and $R_2$ form, together with the ring atoms to which they are attached, a condensed 6 membered unsaturated heterocyclic ring, containing 1 heteroatom being N.

6. The compound according to claim 1, wherein ring A is selected from the following groups wherein an asterisk denotes the point of attachment to the parent molecular moiety

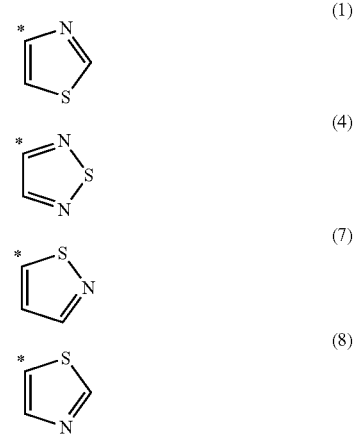

(1)

(4)

(7)

(8)

-continued

(10) 

wherein group (1), (4), (7), (8), or (10) is substituted with 1 substituent R$_1$, or group (1), (4), (7), (8), or (10) is substituted with 2 substituents R$_1$ and R$_2$, or group (1), (4), (7), (8), or (10) is substituted with 3 substituents R$_1$, R$_2$, and R$_3$;

R$_1$ is (C$_1$-C$_6$)alkoxy(C$_1$-C$_6$)alkyl, R$_5$R$_6$N—(C═O)—, or selected from the following groups wherein an asterisk denotes the point of attachment to the parent molecular moiety (2') 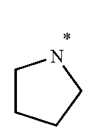

(4') 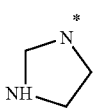

(5') 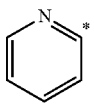

(9') 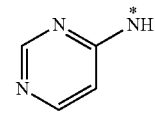

wherein group (2'), (4'), (5'), or (9') is optionally substituted with 1, 2, 3, or 4 substituent(s) each independently being (C$_1$-C$_6$)alkyl or oxo;

R$_2$ is (C$_1$-C$_6$)alkyl;
R$_3$ is (C$_1$-C$_6$)alkyl;
R$_5$ is (C$_1$-C$_6$)alkyl; and
R$_6$ is (C$_1$-C$_6$)alkyl.

7. The compound according to claim 1, wherein ring A is selected from the following groups wherein an asterisk denotes the point of attachment to the parent molecular moiety

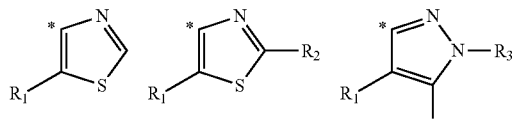

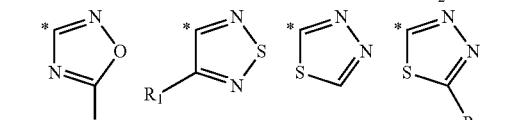

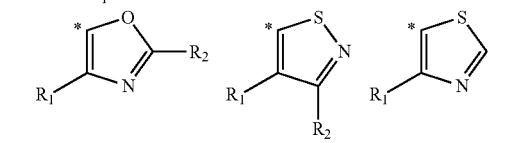

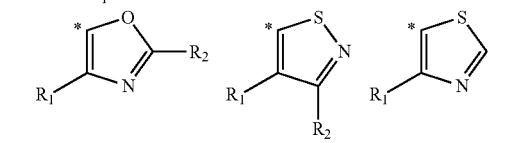

-continued

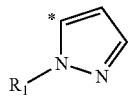 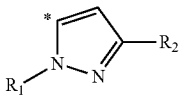 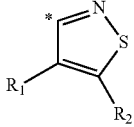

R$_1$ is hydroxy(C$_1$-C$_6$)alkyl, (C$_1$-C$_6$)alkoxy(C$_1$-C$_6$)alkyl, (C$_1$-C$_6$)alkoxy-(C═O)—, CN, (C$_1$-C$_6$)alkyl-(C═O)—, R$_5$R$_6$N—(C═O)—, R$_6$(C═O)—R$_5$N—, or selected from the following groups wherein an asterisk denotes the point of attachment to the parent molecular moiety (1') 

(2') 

(3') 

(4') 

(5') 

(6') 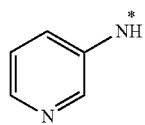

(7') 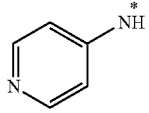

(8') 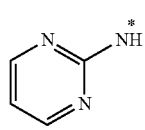

(9') 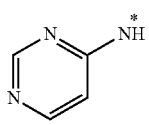

-continued

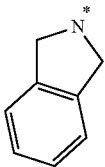
(10')

wherein group (1'), (2'), (3'), (4'), (5'), (6'), (7'), (8'), (9'), or (10'), is optionally substituted with 1,2, 3, or 4 substituent(s) each independently being $(C_1-C_6)$alkyl, $(C_1-C_6)$alkoxy, oxo, or phenyl$(C_1-C_6)$alkoxy;
$R_2$ is $(C_1-C_6)$alkyl;
$R_3$ is $(C_1-C_6)$alkyl;
$R_5$ is H, or $(C_1-C_6)$alkyl; and
$R_6$ is H, or $(C_1-C_6)$alkyl;
or $R_1$ and $R_2$ form, together with the ring atoms to which they are attached, a condensed 6 membered unsaturated heterocyclic ring, containing 1 heteroatom being N.

8. The compound according to claim 7, wherein ring A is selected from the following groups wherein an asterisk denotes the point of attachment to the parent molecular moiety

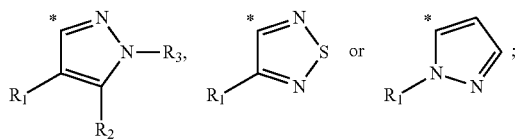

$R_1$ is $R_5R_6N$—(C=O)— or selected from the following groups wherein an asterisk denotes the point of attachment to the parent molecular moiety

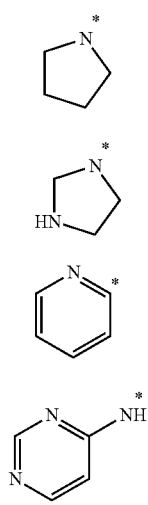

wherein group (2'), (4'), (5'), or (9') is optionally substituted with 1, 2, or 3 substituent(s) each independently being $(C_1-C_3)$alkyl or oxo;
$R_2$ is $(C_1-C_3)$alkyl;
$R_3$ is $(C_1-C_3)$alkyl;
$R_5$ is $(C_1-C_3)$alkyl; and
$R_6$ is $(C_1-C_3)$alkyl.

9. The compound according to claim 1, wherein the compound is chosen from:
(S)-1-(3-(4-((2,3-dihydrobenzo[b][1,4]dioxin-2-yl)methyl)piperazin-1-yl)-1,5-dimethyl-1H-pyrazol-4-yl)-3, 3-dimethylpyrrolidine-2,5-dione,
(S)-2-(3-(4-((2,3-dihydrobenzo[b][1,4]dioxin-2-yl)methyl)piperazin-1-yl)-1,5-dimethyl-1H-pyrazol-4-yl)isoindoline-1,3-dione,
(S)-5-(4-((2,3-dihydrobenzo[b][1,4]dioxin-2-yl)methyl)piperazin-1-yl)-2-methyloxazole-4-carbonitrile,
(S)-1-(3-(4-((2,3-dihydrobenzo[b][1,4]dioxin-2-yl)methyl)piperazin-1-yl)-1,5-dimethyl-1H-pyrazol-4-yl)azetidin-2-one,
(S)-3-(3-(4-((2,3-dihydrobenzo[b][1,4]dioxin-2-yl)methyl)piperazin-1-yl)-1,5-dimethyl-1H-pyrazol-4-yl)oxazolidin-2-one,
(S)-1-(3-(4-((2,3-dihydrobenzo[b][1,4]dioxin-2-yl)methyl)piperazin-1-yl)-1,5-dimethyl-1H-pyrazol-4-yl)-4,4-dimethylimidazolidin-2-one,
(S)-1-(3-(4-((2,3-dihydrobenzo[b][1,4]dioxin-2-yl)methyl)piperazin-1-yl)-1,5-dimethyl-1H-pyrazol-4-yl)-3,4,4-trimethylimidazolidin-2-one,
(S)-4-(4-((2,3-dihydrobenzo[b][1,4]dioxin-2-yl)methyl)piperazin-1-yl)-5-(methoxymethyl)thiazole,
(S)-1-(3-(4-((2,3-dihydrobenzo[b][1,4]dioxin-2-yl)methyl)piperazin-1-yl)-1,5-dimethyl-1H-pyrazol-4-yl)imidazolidin-2-one,
(S)-1-((2,3-dihydrobenzo[b][1,4]dioxin-2-yl)methyl)-4-(1-(pyridin-2-yl)-1H-pyrazol-5-yl)piperazine,
(S)-1-((2,3-dihydrobenzo[b][1,4]dioxin-2-yl)methyl)-4-(4-(methoxymethyl)-1,5-dimethyl-1H-pyrazol-3-yl)piperazine,
(S)-ethyl 3-(4-((2,3-dihydrobenzo[b][1,4]dioxin-2-yl)methyl)piperazin-1-yl)-1,5-dimethyl-1H-pyrazole-4-carboxylate,
(S)-2-(3-(4-((2,3-dihydrobenzo[b][1,4]dioxin-2-yl)methyl)piperazin-1-yl)-1,5-dimethyl-1H-pyrazol-4-yl)propan-2-ol,
(S)-1-(3-(4-((2,3-dihydrobenzo[b][1,4]dioxin-2-yl)methyl)piperazin-1-yl)-1,5-dimethyl-1H-pyrazol-4-yl)pyrrolidin-2-one,
(S)-1-(3-(4-((2,3-dihydrobenzo[b][1,4]dioxin-2-yl)methyl)piperazin-1-yl)-1,5-dimethyl-1H-pyrazol-4-yl)-3-methylimidazolidin-2-one,
(S)—N-(4-(4-((2,3-dihydrobenzo[b][1,4]dioxin-2-yl)methyl)piperazin-1-yl)-1,2,5-thiadiazol-3-yl)acetamide,
(S)-1-(4-(4-((2,3-dihydrobenzo[b][1,4]dioxin-2-yl)methyl)piperazin-1-yl)-1,2,5-thiadiazol-3-yl)-3,3-dimethylpyrrolidin-2-one,
(S)-4-(4-((2,3-dihydrobenzo[b][1,4]dioxin-2-yl)methyl)piperazin-1-yl)-N-(pyrimidin-2-yl)-1,2,5-thiadiazol-3-amine,
(S)-4-(4-((2,3-dihydrobenzo[b][1,4]dioxin-2-yl)methyl)piperazin-1-yl)-N-(pyrimidin-4-yl)-1,2,5-thiadiazol-3-amine,
(S)-1-(5-(4-((2,3-dihydrobenzo[b][1,4]dioxin-2-yl)methyl)piperazin-1-yl)thiazol-4-yl)pyrrolidin-2-one,
1-(4-(4-(((S)-2,3-dihydrobenzo[b][1,4]dioxin-2-yl)methyl)piperazin-1-yl)-1,2,5-thiadiazol-3-yl)-3-methylpyrrolidin-2-one,
(S)-2-(4-((2,3-dihydrobenzo[b][1,4]dioxin-2-yl)methyl)piperazin-1-yl)-1,3,4-thiadiazole,
(S)-3-(4-((2,3-dihydrobenzo[b][1,4]dioxin-2-yl)methyl)piperazin-1-yl)-5-(methoxymethyl)-1,2,4-oxadiazole, (S)-1-(4-(4-((2,3-dihydrobenzo[b][1,4]dioxin-2-yl)methyl)piperazin-1-yl)-1,2,5-thiadiazol-3-yl)pyrrolidin-2-one, (S)-1-(5-(4-((2,3-dihydrobenzo[b][1,4]dioxin-2-yl)methyl)piperazin-1-yl)-, 3,4-thiadiazol-2-yl)imidazolidin-2-one, (S)-3-(4-(4-((2,3-dihydrobenzo[b][1,4]dioxin-2-yl)methyl)piperazin-1-yl)-1,2,5-thiadiazol-3-yl)oxazolidin-2-one, (S)-4-(4-((2,3-dihydrobenzo[b][1,4]dioxin-2-yl)methyl)piperazin-1-yl)-1,2,5-thiadiazole-3-carboxamide, (S)-1-(4-(4-((2,3-dihydrobenzo[b][1,4]dioxin-2-yl)methyl)piperazin-1-yl)-1,2,5-thiadiazol-3-yl)-3-methylimidazolidin-2-one, (S)-4-(4-((2,3-dihydrobenzo[b][1,4]dioxin-2-yl)methyl)piperazin-1-yl)-N-methyl-1,2,5-thiadiazole-3-carboxamide hydrochloride, (S)-1-(4-(4-((2,3-dihydrobenzo[b][1,4]dioxin-2-yl)methyl)piperazin-1-yl)-1,2,5-thiadiazol-3-yl)imidazolidin-2-one, (S)-1-(5-(4-((2,3-dihydrobenzo[b][1,4]dioxin-2-yl)methyl)piperazin-1-yl)-3-methylisothiazol-4-yl)pyrrolidin-2-one, (S)-1-(4-(4-((2,3-dihydrobenzo[b][1,4]dioxin-2-yl)methyl)piperazin-1-yl)-2-methylthiazol-5-yl)-3,3-dimethylpyrrolidine-2,5-dione hydrochloride, (S)-1-(4-(4-((2,3-dihydrobenzo[b][1,4]dioxin-2-yl)methyl)piperazin-1-yl)-1,2,5-thiadiazol-3-yl)ethanone, (S)-4-(4-((2,3-dihydrobenzo[b][1,4]dioxin-2-yl)methyl)piperazin-1-yl)-N,N-dimethyl-1,2,5-thiadiazole-3-carboxamide, (S)-4-(4-((2,3-dihydrobenzo[b][1,4]dioxin-2-yl)methyl)piperazin-1-yl)-N-(pyridin-4-yl)-1,2,5-thiadiazol-3-amine dihydrochloride, (S)-3-(4-((2,3-dihydrobenzo[b][1,4]dioxin-2-yl)methyl)piperazin-1-yl)isothiazolo[4,5-b]pyridine hydrochloride, (S)—N-(2-(benzyloxy)pyridin-3-yl)-4-(4-((2,3-dihydrobenzo[b][1,4]-dioxin-2-yl)methyl)piperazin-1-yl)-1,2,5-thiadiazol-3-amine hydrochloride, (S)-1-((2,3-dihydrobenzo[b][1,4]dioxin-2-yl)methyl)-4-(3-methyl-1-(pyridin-2-yl)-1H-pyrazol-5-yl)piperazine, (S)-1-((2,3-dihydrobenzo[b][1,4]dioxin-2-yl)methyl)-4-(1-(6-methoxypyridin-2-yl)-3-methyl-1H-pyrazol-5-yl)piperazine, or (S)-1-((2,3-dihydrobenzo[b][1,4]dioxin-2-yl)methyl)-4-(3-methyl-1-(6-methylpyridin-2-yl)-1H-pyrazol-5-yl)piperazine.

10. The compound according to claim 1, wherein the compound is

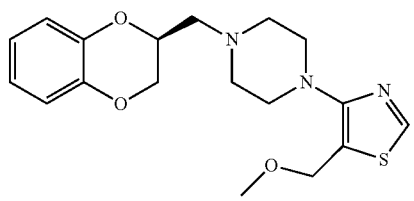 [SMILES: COCc1scnc1N1CCN(C[C@H]2COc3ccccc3O2)CC1]

or a pharmaceutically acceptable salt thereof.

11. The compound according to claim 1, wherein the compound is

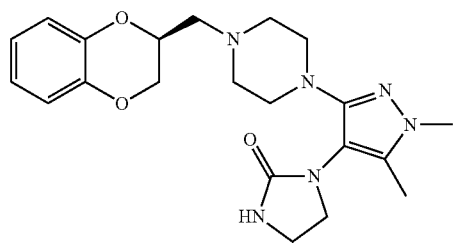 [SMILES: Cc1c(N2CCNC2=O)c(N2CCN(C[C@H]3COc4ccccc4O3)CC2)nn1C]

or a pharmaceutically acceptable salt thereof.

12. The compound according to claim 1, wherein the compound is

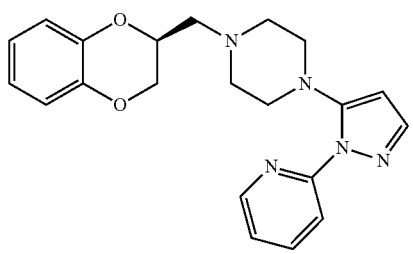 [SMILES: c1ccc(-n2nccc2N2CCN(C[C@H]3COc4ccccc4O3)CC2)nc1]

or a pharmaceutically acceptable salt thereof.

13. The compound according to claim 1, wherein the compound is

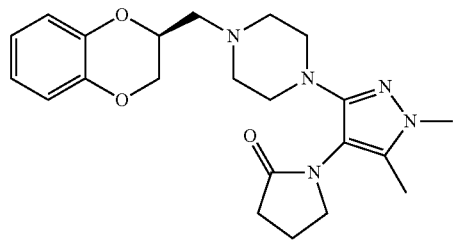 [SMILES: Cc1c(N2CCCC2=O)c(N2CCN(C[C@H]3COc4ccccc4O3)CC2)nn1C]

or a pharmaceutically acceptable salt thereof.

14. The compound according to claim 1, wherein the compound is

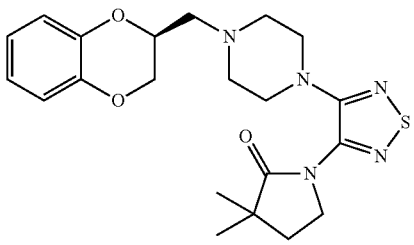 [SMILES: CC1(C)CCN(c2nsnc2N2CCN(C[C@H]3COc4ccccc4O3)CC2)C1=O]

or a pharmaceutically acceptable salt thereof.

15. The compound according to claim 1, wherein the compound is

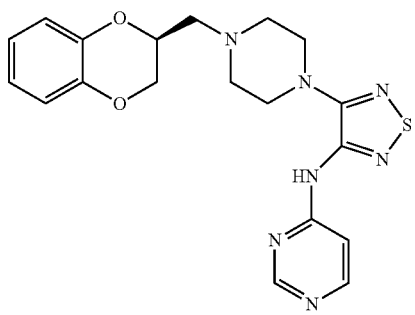 [SMILES: c1ccc2c(c1)OC[C@H](CN1CCN(c3nsnc3Nc3ccncn3)CC1)O2]

or a pharmaceutically acceptable salt thereof.

16. The compound according to claim 1, wherein the compound is

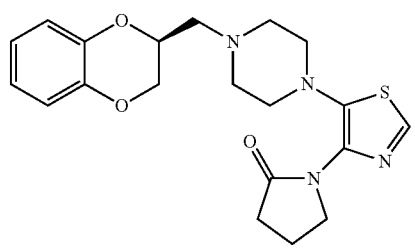 [SMILES: O=C1CCCN1c1ncsc1N1CCN(C[C@H]2COc3ccccc3O2)CC1]

or a pharmaceutically acceptable salt thereof.

17. The compound according to claim 1, wherein the compound is

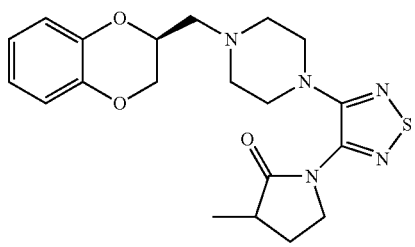 [SMILES: CC1CCN(c2nsnc2N2CCN(C[C@H]3COc4ccccc4O3)CC2)C1=O]

or a pharmaceutically acceptable salt thereof.

18. The compound according to claim 1, wherein the compound is

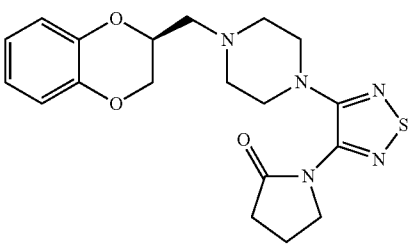 [SMILES: O=C1CCCN1c1nsnc1N1CCN(C[C@H]2COc3ccccc3O2)CC1]

or a pharmaceutically acceptable salt thereof.

19. The compound according to claim 1, wherein the compound is

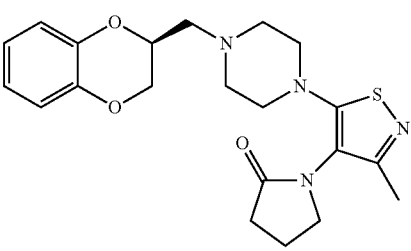 [SMILES: Cc1nsc(N2CCN(C[C@H]3COc4ccccc4O3)CC2)c1N1CCCC1=O]

or a pharmaceutically acceptable salt thereof.

20. The compound according to claim 1, wherein the compound is

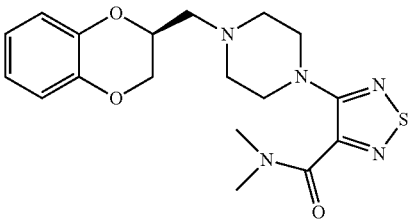

or a pharmaceutically acceptable salt thereof.

21. A pharmaceutical composition comprising at least one compound according to claim 1 and at least one pharmaceutically acceptable carrier, diluent, or excipient.

* * * * *

UNITED STATES PATENT AND TRADEMARK OFFICE
CERTIFICATE OF CORRECTION

PATENT NO. : 10,774,074 B2
APPLICATION NO. : 15/579372
DATED : September 15, 2020
INVENTOR(S) : Shouming Wang et al.

Page 1 of 1

It is certified that error appears in the above-identified patent and that said Letters Patent is hereby corrected as shown below:

In the Claims

In Claim 2, Column 64, Line 2, to the upper right of the chemical structure for formula Ia, "I$^a$" should read as --Ia--.

In Claim 9, Column 73, Lines 4-6, "(S)-1-(5-(4-((2,3-dihydrobenzo[b][1,4]dioxin-2-yl)methyl)piperazin-1-yl)-, 3,4-thiadiazol-2-yl)imidazolidin-2-one," should read as --(S)-1-(5-(4-((2,3-dihydrobenzo[b][1,4]dioxin-2-yl)methyl)piperazin-1-yl)-1,3,4-thiadiazol-2-yl)imidazolidin-2-one,--.

Signed and Sealed this
Tenth Day of November, 2020

Andrei Iancu
*Director of the United States Patent and Trademark Office*